(12) United States Patent
Gnauer et al.

(10) Patent No.: US 10,738,107 B2
(45) Date of Patent: Aug. 11, 2020

(54) METHODS TO PRODUCE A HUMAN PLASMA-DERIVED IGG PREPARATION ENRICHED IN BRAIN DISEASE-RELATED NATURAL IGGS

(71) Applicants: Baxalta Incorporated, Bannockburn, IL (US); Baxalta GmbH, Glattpark (Opfikon) (CH)

(72) Inventors: Lucia Gnauer, Eggenburg (AT); Harald Arno Butterweck, Vienna (AT); Theresa Bauer, Vienna (AT); Alfred Weber, Vienna (AT); Wolfgang Teschner, Vienna (AT); Hans-Peter Schwarz, Vienna (AT)

(73) Assignees: Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 270 days.

(21) Appl. No.: 15/385,721

(22) Filed: Dec. 20, 2016

(65) Prior Publication Data

US 2017/0218051 A1    Aug. 3, 2017

Related U.S. Application Data

(62) Division of application No. 14/213,585, filed on Mar. 14, 2014, now Pat. No. 9,556,261.

(60) Provisional application No. 61/794,378, filed on Mar. 15, 2013.

(51) Int. Cl.
| | | |
|---|---|---|
| *A61K 39/00* | (2006.01) | |
| *C07K 14/47* | (2006.01) | |
| *B01D 15/36* | (2006.01) | |
| *C07K 16/18* | (2006.01) | |
| *B01D 15/16* | (2006.01) | |
| *C07K 16/28* | (2006.01) | |
| *B01D 15/42* | (2006.01) | |
| *C07K 16/06* | (2006.01) | |
| *B01D 61/02* | (2006.01) | |

(52) U.S. Cl.
CPC .............. *C07K 16/18* (2013.01); *B01D 15/16* (2013.01); *B01D 15/362* (2013.01); *B01D 15/363* (2013.01); *B01D 15/426* (2013.01); *B01D 61/027* (2013.01); *C07K 16/065* (2013.01); *C07K 16/2803* (2013.01); *A61K 2039/507* (2013.01); *B01D 2311/2623* (2013.01); *C07K 14/4717* (2013.01); *C07K 2317/732* (2013.01)

(58) Field of Classification Search
None
See application file for complete search history.

(56) References Cited

U.S. PATENT DOCUMENTS

| | | |
|---|---|---|
| 4,296,027 A | 10/1981 | Condie |
| 4,434,093 A | 2/1984 | Zolton et al. |
| 5,258,503 A | 11/1993 | Yokohari et al. |
| 5,593,675 A | 1/1997 | Hodler et al. |
| 5,608,038 A | 3/1997 | Eibl et al. |
| 5,644,036 A | 7/1997 | Ramage et al. |
| 6,414,125 B1 | 7/2002 | Siekmann et al. |
| 6,835,379 B2 | 12/2004 | Andersson et al. |
| 7,138,120 B2 | 11/2006 | Laursen et al. |
| 7,993,580 B2 | 8/2011 | Anderle et al. |
| 8,114,633 B2 | 2/2012 | Weber et al. |
| 8,546,548 B2 | 10/2013 | Teschner et al. |
| 2001/0051708 A1 | 12/2001 | Laursen et al. |
| 2002/0009445 A1 | 1/2002 | Du et al. |
| 2006/0099211 A1 | 5/2006 | Monthe et al. |
| 2007/0037170 A1 | 2/2007 | Nur et al. |
| 2010/0040601 A1 | 2/2010 | Cantin et al. |
| 2010/0330071 A1 | 12/2010 | Teschner et al. |
| 2011/0213126 A1 | 9/2011 | Gonzalez et al. |
| 2012/0039886 A1 | 2/2012 | Elzaabi |

(Continued)

FOREIGN PATENT DOCUMENTS

| | | |
|---|---|---|
| EP | 2 272 870 A1 | 1/2011 |
| WO | WO 95/18155 A1 | 7/1995 |

(Continued)

OTHER PUBLICATIONS

Weber et al., Abstract P3-248 "Intravenous immunoglobulin (IVIG) gammagard liquid contains anti-RAGE IgG and SLRP" J of the Alzheimer's Association, 5(4), p. 416 (Year: 2009).*

(Continued)

*Primary Examiner* — Daniel E Kolker
*Assistant Examiner* — James L Rogers
(74) *Attorney, Agent, or Firm* — Morgan, Lewis & Bockius LLP

(57) ABSTRACT

The present invention provides, among other aspects, methods for the manufacture of plasma-derived immunoglobulin G compositions highly enriched for anti-brain disease related protein antibodies (e.g., anti-Aβ, anti-RAGE, and anti-α-synuclein antibodies). Advantageously, the methods provided do not affect the manufacturing processes or capabilities for producing plasma-derived IgG therapeutics. Plasma-derived IgG compositions that are highly enriched for anti-brain disease related protein antibodies (e.g., anti-Aβ, anti-RAGE, and anti-α-synuclein antibodies), as also provided here. Methods for the treatment of brain diseases and disorders by administration of plasma-derived IgG compositions highly enriched for anti-brain disease related protein antibodies (e.g., anti-Aβ, anti-RAGE, and anti-α-synuclein antibodies), are also provided.

11 Claims, 23 Drawing Sheets
(22 of 23 Drawing Sheet(s) Filed in Color)

(56) References Cited

U.S. PATENT DOCUMENTS

| | | | |
|---|---|---|---|
| 2012/0183527 A1* | 7/2012 | Relkin | C07K 16/18 424/130.1 |
| 2012/0251524 A1 | 10/2012 | Relkin et al. | |
| 2012/0294847 A1 | 11/2012 | Mintz et al. | |
| 2013/0052200 A1* | 2/2013 | Dodel | C07K 16/28 424/139.1 |
| 2013/0101579 A1 | 4/2013 | Bruckschwaiger et al. | |
| 2013/0149700 A1 | 7/2013 | Weber et al. | |
| 2013/0224183 A1 | 8/2013 | Bruckschwaiger et al. | |
| 2013/0224184 A1 | 8/2013 | Bruckschwaiger et al. | |
| 2014/0030252 A1 | 1/2014 | Teschner et al. | |
| 2014/0232029 A1 | 8/2014 | Varadi et al. | |
| 2014/0271669 A1 | 9/2014 | Hofbauer et al. | |
| 2014/0271679 A1 | 9/2014 | Hofbauer et al. | |

FOREIGN PATENT DOCUMENTS

| | | |
|---|---|---|
| WO | WO 2004/024866 A2 | 3/2004 |
| WO | WO 2008/084402 A2 | 7/2008 |
| WO | WO 2008/084402 A3 | 7/2008 |
| WO | WO 2008/087184 A2 | 7/2008 |
| WO | WO 2009/005870 A2 | 1/2009 |
| WO | WO 2009/005870 A3 | 1/2009 |
| WO | WO 2009/043103 A1 | 4/2009 |
| WO | WO 2010/138736 A2 | 12/2010 |
| WO | WO 2010/138736 A3 | 12/2010 |
| WO | WO 2011/149472 A1 | 12/2011 |
| WO | WO 2011/150284 A2 | 12/2011 |
| WO | WO 2011/150284 A3 | 12/2011 |
| WO | WO 2012/049245 A1 | 4/2012 |
| WO | WO 2013/019652 A1 | 2/2013 |
| WO | WO 2013/033042 A1 | 3/2013 |

OTHER PUBLICATIONS

Welzel et al. "Human anti-AB IgGs target conformation epitopes on synthetic dimer assemblies and the AD brain-derived peptide" PLOS, 7(11), pp. 1-12, Nov. 2012 (Year: 2012).*
Adekar, S.P. et al., "Inherent Anti-amyloidogenic Activity of Human Immunoglobulin γ Heavy Chains," *The Journal of Biological Chemistry*, Jan. 8, 2010, vol. 285, No. 2, pp. 1066-1074.
Anthony, R.M. et al., "A Recombinant IgC Fc That Recapitulates the Anti-Inflammatory Activity of IVIG," *Science*, Apr. 18, 2008, vol. 320, No. 5874, pp. 373-376.
Bayry, J. et al., "DC-SIGN and α2,6-sialylated IgG Fc interaction is dispensable for the anti-inflammatory activity of IVIg on human dendritic cells," *PNAS*, Mar. 3, 2009, vol. 106, No. 9, p. E24.
Cohn, E.J. et al., "Preparation and Properties of Serum and Plasma Proteins, IV. A System for the Separation into Fractions of the Protein and Lipoprotein Components of Biological Tissues and Fluids," *J Am Chem Soc*, 1946, vol. 68, pp. 459-475.
Dodel, R.C. et al., "Intravenous immunoglobulins containing antibodies against β-amyloid for the treatment of Alzheimer's disease," *J Neurol Neurosurg Psychiatry*, 2004, vol. 75, pp. 1472-1474.
Edson De Souza Lucena, A. et al., "A new methodology for polyvalent intravenous immunoglobulin solution production with a two-stage process of viral inactivation," *BJPS*, 2010, vol. 46, No. 4, pp. 777-783.
Epstein, J.S. et al., "Current Safety of Clotting Factor Concentrates," *Arch Pathol Lab Med*, Mar. 1990, vol. 114, pp. 335-339.
Fisher, A. et al., eds. *New Trends in Alzheimer and Parkinson Related Disorders: ADPD 2009, Collection of Selected Free Papers from the 9th International Conference on Alzheimer's and Parkinson's Disease AD/PD*, Prague, Czech Republic, Mar. 11-15, 2009, Index only, 9 pages.
Hamamoto, Y. et al., "A Novel Method for Removal of Human Immunodeficiency Virus: Filtration with Porous Polymeric Membranes," *Vox Sang.*, 1989, vol. 56, pp. 230-236.
Horowitz, B. et al., "Viral safety of solvent/detergent-treated blood products," *Blood Coagulation and Fibrinolysis*, 1994, vol. 5, Suppl 3, pp. S21-S28.

Hyman, B.T. et al., "Autoantibodies to Amyloid-β and Alzheimer's Disease," *Ann Neurol*, 2001, vol. 49, pp. 808-810.
International Search Report for International Patent Application No. PCT/US2014/028953, dated Aug. 21, 2014, 8 pages.
Kaneko, Y. et al., "Anti-Inflammatory Activity of Immunoglobulin G Resulting from Fc Sialylation," *Science*, Aug. 4, 2006, vol. 313, pp. 670-673.
Kempf, C. et al., "Virus inactivation during production of intravenous immunoglobulin," *Transfusion*, 1991, vol. 31, pp. 423-427.
Kistler, P. et al., "Large Scale Production of Human Plasma Fractions," *Vox Sang.*, 1962, vol. 7, pp. 414-424.
Kreil, T.R. et al., "West Nile virus and the safety of plasma derivatives: verification of high safety margins, and the validity of predictions based on model virus data," *Transfusion*, Aug. 2003, vol. 43, pp. 1023-1028.
Louie, R.E. et al., "Inactivation of Hepatitis C Virus in Low pH Intravenous Immunoglobulin," *Biologicals*, 1994, vol. 22, pp. 13-19.
Magga, J. et al., "Human intravenous immunoglobulin provides protection against Aβ toxicity by multiple mechanisms in a mouse model of Alzheimer's disease," *Journal of Neuroinflammation*, 2010, vol. 7, No. 90, 15 pages.
Mruthinti, S. et al., "Autoimmunity in Alzheimer's disease: increased levels of circulating IgGs binding Aβ and RAGE peptides," *Neurobiology of Aging*, 2004, vol. 25, pp. 1023-1032.
Nath, A. et al., "Autoantibodies to Amyloid β-Peptide (Aβ) are Increased in Alzheimer's Disease Patients and Aβ Antibodies Can Enhance Aβ Neurotoxicity," *NeuroMolecular Medicine*, 2003, vol. 3, pp. 29-39.
Nimmmerjahn, F., et al., "The antiinflammatory activity of IgG: the intravenous IgG paradox," *JEM*, Jan. 22, 2007, vol. 204, pp. 11-15.
O'Nuallain, B. et al., "Human Plasma Contains Cross-Reactive Aβ Conformer-Specific IgG Antibodies," *Biochemistry*, 2008, vol. 47, pp. 12254-12256.
Oncley, J.L. et al., "The Separation of the Antibodies, Isoagglutinins, Prothrombin, Plasminogen and $_{\beta 1}$-Lipoprotein into Subfractions of Human Plasma," *J Am Chem Soc.*, 1949, vol. 71, pp. 541-550.
Parkkinen, J. et al., "A modified caprylic acid method for manufacturing immunoglobulin G from human plasma with high yield and efficient virus clearance," *Vox Sanguinis*, 2006, vol. 90, pp. 97-104.
Pelletier, J.P.R. et al., "Pathogen inactivation techniques," *Best Practice & Research Clinical Haematology*, 2006, vol. 19, No. 1, pp. 205-242.
Piszkiewicz, D. et al., "Heat Inactivation of Human Immunodeficiency Virus in Lyophilized Factor VIII and Factor IX Concentrates," *Thrombosis Research*, 1987, vol. 47, pp. 235-241.
Piszkiewicz, D. et al., "Virus Inactivation by Heat Treatment of Lyophilized Coagulation Factor Concentrates," *Cuff Stud Hematol Blood Transfus.*, 1989, vol. 56, pp. 44-54.
Puli, L. et al., "Effects of human intravenous immunoglobulin on amyloid pathology and neuroinflammation in a mouse model of Alzheimer's disease," *Journal of Neuroinflammation*, 2012, vol. 9, No. 105, 19 pages.
Relkin, N.R. et al., "18-Month study of intravenous immunoglobulin for treatment of mild Alzheimer disease," *Neurobiology of Aging*, 2009, vol. 30, pp. 1728-1736.
Sohn, J-H. et al., "Dentification of autoantibody against beta-amyloid peptide in the serum of elderly," *Frontiers in Bioscience*, Jan. 1, 2009, vol. 14, pp. 3879-3883.
Szabo, P. et al., "Measurement of anti-beta amyloid antibodies in human blood," *Journal of Neuroimmunology*, 2010, vol. 227, pp. 167-174.
Teschner, W. et al., "A new liquid, intravenous immunoglobulin product (IVIG 10%) highly purified by a state-of-the-art process," *Vox Sanguinis*, 2007, vol. 27, pp. 42-55.
Weksler, M.E. et al., "Patients with Alzheimer disease have lower levels of serum anti-amyloid peptide antibodies than healthy elderly individuals," *Experimental Gerontology*, 2002, vol. 37, pp. 943-948.
Yuasa, T. et al., "The particle size of hepatitis C virus estimated by filtration through microporous regenerated cellulose fibre," *Journal of General Virology*, 1991, vol. 72, pp. 2021-2024.

(56) References Cited

OTHER PUBLICATIONS

Zhou, J.X. et al., "pH-conductivity hybrid gradient cation-exchange chromatography for process-scale monoclonal antibody purification," *Journal of Chromatography A*, 2007, vol. 1175, pp. 69-80.
Dantal (2013) "Intravenous immunoglobulins: in-depth review of excipients and acute kidney injury risk," American journal of nephrology. 38(4):275-284.
O'Nuallain et al. (2008) "Human plasma contains cross-reactive Aβ conformer-specific IgG antibodies," Biochemistry. 47(1):12254-12256.
Porath et al. (1987) "'Thiophilic' interaction and the selective adsorption of proteins," Trends in Biotechnology. 5(8):225-229.
O'Nuallain et al. (2010) "Anti-amyloidogenic activity of IgGs contained in normal plasma," Journal of clinical immunology. 30(1):37-42.
Schauer et al. (2003) "IgG subclass concentrations in certified reference material 470 and reference values for children and adults determined with the binding site reagents," Clinical chemistry. 49(11):1924-1929.

\* cited by examiner

Anti-Aβ40 fibril IgG measured using PBS

| Lot No. | Eluate fraction (E) | | | | 2M wash fraction (2M) | | | | Ratio 2M/E |
|---|---|---|---|---|---|---|---|---|---|
| | Fibrils | Blank | Blank/Aβ | OD/mg | Fibrils | Blank | Blank/Aβ | OD/mg | |
| LE12H252Z | 0.473 | 0.078 | 0.16 | 0.453 | 1.922 | 0.591 | 0.31 | 1.843 | 4.1 |
| LE12H253Z | 0.601 | 0.087 | 0.17 | 0.498 | 2.039 | 0.875 | 0.43 | 1.874 | 3.8 |
| LE12H254Z | 0.934 | 0.171 | 0.18 | 0.919 | 1.906 | 1.266 | 0.66 | 1.309 | 1.4 |
| LE12H255Z | 0.743 | 0.103 | 0.16 | 0.706 | 1.106 | 0.227 | 0.20 | 1.530 | 2.2 |
| LE12H256Z | 0.868 | 0.148 | 0.17 | 0.914 | 2.078 | 1.287 | 0.62 | 1.289 | 1.4 |
| LE12H302Z | 0.669 | 0.147 | 0.22 | 0.323 | 1.704 | 0.914 | 0.54 | 1.363 | 4.2 |
| LE12H303Z | 0.576 | 0.167 | 0.29 | 0.482 | 1.212 | 0.387 | 0.32 | 0.981 | 2.0 |
| LE12H304Z | 0.357 | 0.151 | 0.42 | 0.243 | 1.148 | 0.379 | 0.33 | 1.022 | 4.2 |
| Mean | 0.652 | 0.131 | 0.22 | 0.567 | 1.639 | 0.741 | 0.43 | 1.401 | 2.5 |

Figure 2A

Anti-Aβ40 fibril IgG measured using the low ionic strength buffer

| Lot No. | Eluate fraction (E) | | | | 2M wash fraction (2M) | | | | Ratio 2M/E |
|---|---|---|---|---|---|---|---|---|---|
| | Fibrils | Blank | Blank/Aβ | OD/mg | Fibrils | Blank | Blank/Aβ | OD/mg | |
| LE12H252Z | 0.296 | 0.007 | 0.02 | 0.844 | 1.794 | 0.023 | 0.01 | 4.226 | 5.0 |
| LE12H253Z | 0.233 | 0.010 | 0.04 | 0.545 | 1.787 | 0.029 | 0.02 | 4.331 | 8.0 |
| LE12H254Z | 0.335 | 0.007 | 0.02 | 1.060 | 1.717 | 0.019 | 0.01 | 4.031 | 3.8 |
| LE12H255Z | 0.269 | 0.007 | 0.03 | 0.881 | 1.717 | 0.022 | 0.01 | 4.268 | 4.8 |
| LE12H256Z | 0.401 | 0.004 | 0.01 | 1.202 | 1.673 | 0.017 | 0.01 | 4.003 | 3.3 |
| LE12H302Z | 0.323 | 0.012 | 0.04 | 1.003 | 1.532 | 0.029 | 0.02 | 3.428 | 3.4 |
| LE12H303Z | 0.351 | 0.014 | 0.04 | 0.817 | 1.566 | 0.030 | 0.02 | 4.154 | 5.1 |
| LE12H304Z | 0.252 | 0.013 | 0.05 | 0.579 | 1.817 | 0.048 | 0.03 | 3.386 | 5.9 |
| Mean | 0.308 | 0.009 | 0.03 | 0.866 | 1.700 | 0.027 | 0.02 | 3.978 | 4.6 |

Figure 2B

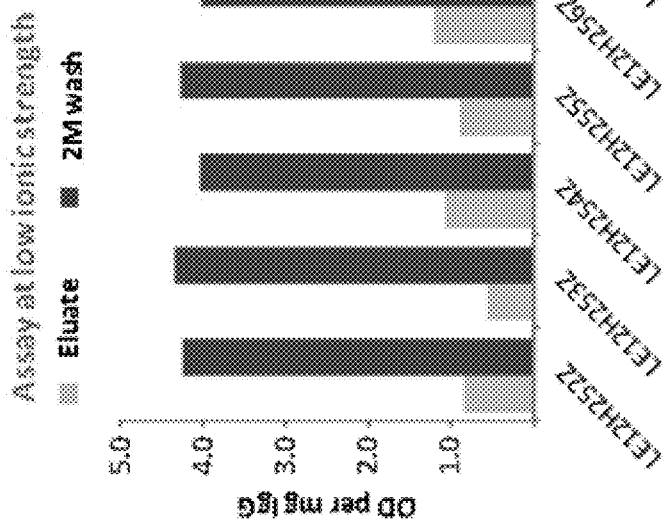
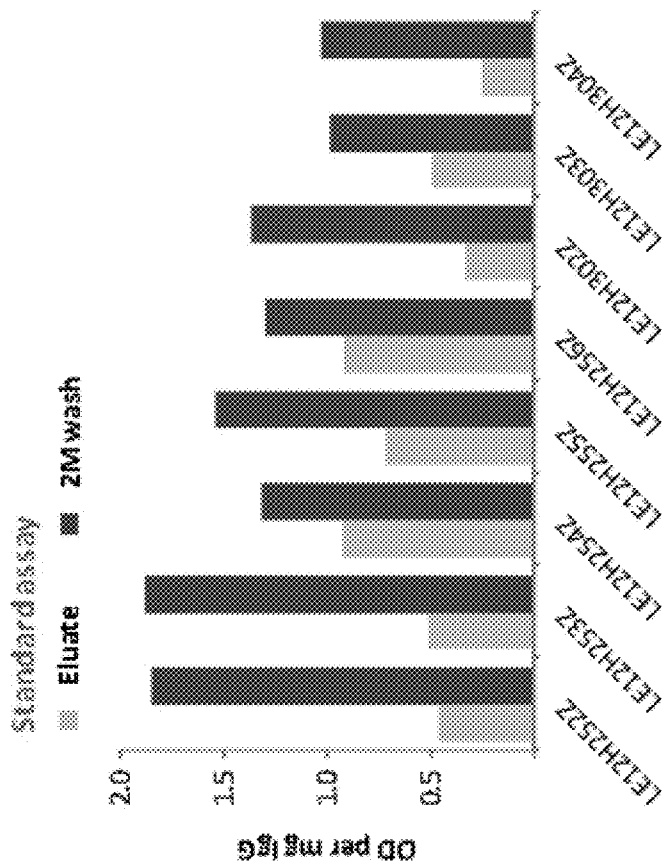
Figure 3A
Figure 3B

Anti-Aβ40 CAPS IgG measured using PBS

| Lot No. | Eluate fraction (E) | | | | 2M wash fraction (2M) | | | | Ratio 2M / E |
|---|---|---|---|---|---|---|---|---|---|
| | CAPS | Blank | Blank/Aβ | OD/mg | CAPS | Blank | Blank/Aβ | OD/mg | |
| LE12H252Z | 1.107 | 0.075 | 0.07 | 0.632 | 2.000 | 1.192 | 0.60 | 1.378 | 2.2 |
| LE12H253Z | 1.086 | 0.095 | 0.09 | 1.132 | 1.901 | 1.478 | 0.78 | 2.309 | 2.0 |
| LE12H254Z | 1.418 | 0.189 | 0.13 | 0.683 | 2.117 | 1.271 | 0.60 | 1.565 | 2.3 |
| LE12H255Z | 1.324 | 0.112 | 0.08 | 0.800 | 1.537 | 0.267 | 0.17 | 1.596 | 2.0 |
| LE12H256Z | 1.133 | 0.100 | 0.09 | 0.670 | 1.825 | 0.508 | 0.28 | 1.907 | 2.9 |
| LE12H302Z | 0.917 | 0.160 | 0.17 | 0.928 | 2.078 | 0.943 | 0.45 | 1.888 | 2.0 |
| LE12H303Z | 1.061 | 0.174 | 0.16 | 0.870 | 1.680 | 0.361 | 0.21 | 1.720 | 2.0 |
| LE12H304Z | 0.802 | 0.133 | 0.17 | 0.850 | 1.425 | 0.337 | 0.24 | 1.524 | 1.8 |
| Mean | 1.106 | 0.130 | 0.12 | 0.821 | 1.820 | 0.795 | 0.42 | 1.736 | 2.1 |

Figure 4A

Anti-Aβ40 CAPS IgG measured using the low ionic strength buffer

| Lot No. | Eluate fraction (E) | | | | 2M wash fraction (2M) | | | | Ratio 2M / E |
|---|---|---|---|---|---|---|---|---|---|
| | Aβ40 | Blank | Blank/Aβ | OD/mg | Aβ40 | Blank | Blank/Aβ | OD/mg | |
| LE12H252Z | 0.489 | 0.009 | 0.02 | 1.252 | 1.848 | 0.022 | 0.01 | 3.996 | 3.2 |
| LE12H253Z | 0.424 | 0.014 | 0.03 | 1.450 | 1.816 | 0.027 | 0.02 | 4.587 | 3.2 |
| LE12H254Z | 0.601 | 0.005 | 0.01 | 1.876 | 1.752 | 0.019 | 0.01 | 3.343 | 1.8 |
| LE12H255Z | 0.437 | 0.009 | 0.02 | 1.408 | 1.739 | 0.026 | 0.02 | 4.506 | 3.2 |
| LE12H256Z | 0.529 | 0.004 | 0.01 | 1.389 | 1.800 | 0.029 | 0.02 | 3.437 | 2.5 |
| LE12H302Z | 0.596 | 0.012 | 0.02 | 1.588 | 2.169 | 0.024 | 0.01 | 6.159 | 3.9 |
| LE12H303Z | 0.579 | 0.021 | 0.04 | 1.579 | 2.049 | 0.022 | 0.01 | 6.886 | 4.4 |
| LE12H304Z | 0.471 | 0.011 | 0.02 | 1.492 | 2.270 | 0.034 | 0.02 | 4.114 | 2.8 |
| Mean | 0.516 | 0.011 | 0.02 | 1.504 | 1.930 | 0.025 | 0.02 | 4.629 | 3.1 |

Figure 4B

Anti-Aβ42 monomer IgG measured using PBS

| Lot No. | Eluate fraction (E) | | | | 2M wash fraction (2M) | | | | Ratio 2M / E |
|---|---|---|---|---|---|---|---|---|---|
| | Aβ42 | Blank | Blank/Aβ | OD/mg | Aβ42 | Blank | Blank/Aβ | OD/mg | |
| LE12H252Z | 0.525 | 0.055 | 0.10 | 0.548 | 1.853 | 0.719 | 0.39 | 1.619 | 3.0 |
| LE12H253Z | 0.907 | 0.073 | 0.08 | 1.002 | 1.972 | 0.923 | 0.47 | 2.164 | 2.2 |
| LE12H254Z | 1.069 | 0.127 | 0.12 | 0.967 | 1.828 | 1.007 | 0.55 | 1.275 | 1.3 |
| LE12H255Z | 1.020 | 0.078 | 0.08 | 1.069 | 0.825 | 0.148 | 0.18 | 2.466 | 2.3 |
| LE12H256Z | 1.289 | 0.105 | 0.08 | 1.565 | 1.887 | 0.878 | 0.47 | 1.403 | 0.9 |
| LE12H302Z | 0.782 | 0.156 | 0.20 | 0.782 | 1.634 | 0.582 | 0.36 | 1.530 | 2.0 |
| LE12H303Z | 1.030 | 0.149 | 0.14 | 1.069 | 1.197 | 0.327 | 0.27 | 1.210 | 1.1 |
| LE12H304Z | 0.695 | 0.151 | 0.22 | 0.673 | 1.200 | 0.415 | 0.35 | 1.333 | 2.0 |
| Mean | 0.914 | 0.112 | 0.13 | 0.959 | 1.549 | 0.625 | 0.38 | 1.625 | 1.7 |

Figure 6A

Anti-Aβ42 monomer IgG measured using the low ionic strength buffer

| Lot No. | Eluate fraction (E) | | | | 2M wash fraction (2M) | | | | Ratio 2M / E |
|---|---|---|---|---|---|---|---|---|---|
| | Aβ42 | Blank | Blank/Aβ | OD/mg | Aβ42 | Blank | Blank/Aβ | OD/mg | |
| LE12H252Z | 0.359 | 0.033 | 0.09 | 1.043 | 1.385 | 0.014 | 0.01 | 3.890 | 3.7 |
| LE12H253Z | 0.388 | 0.013 | 0.05 | 0.658 | 1.450 | 0.023 | 0.02 | 3.699 | 5.6 |
| LE12H254Z | 0.334 | 0.004 | 0.01 | 0.809 | 1.604 | 0.020 | 0.01 | 3.891 | 4.8 |
| LE12H255Z | 0.237 | 0.010 | 0.04 | 0.530 | 1.602 | 0.021 | 0.01 | 4.123 | 7.8 |
| LE12H256Z | 0.291 | 0.004 | 0.01 | 0.776 | 1.746 | 0.029 | 0.02 | 4.057 | 5.2 |
| LE12H302Z | 0.398 | 0.012 | 0.03 | 1.177 | 1.453 | 0.030 | 0.02 | 3.301 | 2.8 |
| LE12H303Z | 0.460 | 0.020 | 0.04 | 1.611 | 1.474 | 0.030 | 0.02 | 3.755 | 2.3 |
| LE12H304Z | 0.566 | 0.009 | 0.02 | 1.867 | 1.973 | 0.098 | 0.05 | 4.203 | 2.3 |
| Mean | 0.367 | 0.013 | 0.04 | 1.059 | 1.586 | 0.033 | 0.02 | 3.865 | 3.7 |

Figure 6B

Relative distribution of IgG subclasses

| Lot No | Eluat | | | | 2M wash fraction | | | |
|---|---|---|---|---|---|---|---|---|
| | IgG1 | IgG2 | IgG3 | IgG4 | IgG1 | IgG2 | IgG3 | IgG4 |
| LE12H252Z | 58.1 | 34.7 | 3.9 | 3.3 | 59.8 | 19.1 | 20.7 | 0.41 |
| LE12H253Z | 56.7 | 36.3 | 3.7 | 3.2 | 57.8 | 18.4 | 23.4 | 0.42 |
| LE12H254Z | 60.9 | 30.2 | 5.4 | 3.5 | 51.1 | 15.0 | 34.2 | 0.37 |
| LE12H255Z | 55.2 | 35.2 | 5.0 | 4.6 | 51.0 | 19.1 | 29.3 | 0.58 |
| LE12H256Z | 61.6 | 28.8 | 5.4 | 4.1 | 53.3 | 14.1 | 32.1 | 0.41 |
| LE12H302Z | 62.2 | 28.1 | 5.5 | 4.2 | 54.3 | 17.5 | 27.6 | 0.64 |
| LE12H303Z | 63.3 | 27.3 | 5.3 | 4.1 | 55.5 | 15.4 | 28.6 | 0.54 |
| LE12H304Z | 62.1 | 28.8 | 5.0 | 4.1 | 55.5 | 16.3 | 27.6 | 0.60 |
| Mean | 60.0 | 31.2 | 4.9 | 3.9 | 54.8 | 16.9 | 28.0 | 0.5 |

IgA and IgM concentrations

| Lot No. | Eluate ||||| 2M wash fraction |||||
|---|---|---|---|---|---|---|---|---|---|---|
| | IgG mg/mL | IgA µg/mL | µg IgA/ mg IgG | IgM µg/mL | µg IgM/ mg IgG | IgG mg/mL | IgA µg/mL | µg IgA/ mg IgG | IgM µg/mL | µg IgM/ mg IgG |
| LE12H252Z | 6.54 | 640 | 98 | 116 | 18 | 4.27 | 136 | 32 | 152 | 36 |
| LE12H253Z | 8.41 | 709 | 84 | 150 | 18 | 5.19 | 167 | 32 | 283 | 55 |
| LE12H254Z | 2.38 | 259 | 109 | 41 | 17 | 3.90 | 196 | 50 | 224 | 57 |
| LE12H255Z | 9.86 | 1060 | 108 | 156 | 16 | 2.00 | 80 | 40 | 75 | 37 |
| LE12H256Z | 9.12 | 970 | 106 | 174 | 19 | 4.44 | 185 | 42 | 165 | 37 |
| LE12H302Z | 9.74 | 1720 | 177 | 218 | 22 | 2.14 | 140 | 65 | 159 | 74 |
| LE12H303Z | 7.95 | 1320 | 166 | 172 | 22 | 3.77 | 222 | 59 | 233 | 62 |
| LE12H304Z | 10.3 | 1370 | 133 | 199 | 19 | 2.94 | 210 | 71 | 231 | 78 |
| Mean | 8.04 | 1006 | 123 | 153 | 19 | 3.58 | 167 | 49 | 190 | 55 |

HP-SEC analysis

| Lot No. | Eluate | | | | 2M wash fraction | | | |
|---|---|---|---|---|---|---|---|---|
| | Peak 1 | Peak 2 | Peak 3 | Peak 4 | Peak 1 | Peak 2 | Peak 3 | Peak 4 |
| LE12H252Z | 3.15 | 9.65 | 87.20 | <0.1 | 4.94 | 16.37 | 77.18 | 1.51 |
| LE12H253Z | 4.08 | 12.98 | 82.94 | <0.1 | 7.77 | 15.06 | 74.82 | 2.34 |
| LE12H254Z | 3.57 | 12.21 | 84.21 | <0.1 | 8.88 | 21.99 | 66.90 | 2.23 |
| LE12H255Z | 4.03 | 13.19 | 82.78 | <0.1 | 4.11 | 18.58 | 73.80 | 3.52 |
| LE12H256Z | 8.41 | 12.10 | 79.48 | <0.1 | 5.17 | 20.50 | 70.93 | 3.40 |
| LE12H302Z | 4.49 | 14.60 | 80.92 | <0.1 | 18.47 | 18.25 | 61.98 | 1.30 |
| LE12H303Z | 5.16 | 15.22 | 79.63 | <0.1 | 11.85 | 20.22 | 66.71 | 1.20 |
| LE12H304Z | 4.49 | 14.62 | 80.90 | <0.1 | 12.80 | 19.06 | 67.57 | 0.57 |
| Mean | 4.67 | 13.07 | 82.26 | <0.1 | 9.24 | 18.75 | 69.99 | 2.01 |

IgG SNA binding

| Lot No. | Eluate | | | | | 2M wash fraction | | | | |
|---|---|---|---|---|---|---|---|---|---|---|
| | [1] | [2] | [3] | Mean | RSD | [1] | [2] | [3] | Mean | RSD |
| LE12H252Z | 64.3 | 64.1 | 67.2 | 65.2 | 2.7 | 93.2 | 98.2 | 96.0 | 95.8 | 2.6 |
| LE12H253Z | 63.2 | 67.1 | 69.1 | 66.5 | 4.5 | 89.1 | 89.4 | 93.4 | 90.6 | 2.6 |
| LE12H254Z | 70.2 | 76.8 | 82.0 | 76.3 | 7.7 | 125.4 | 127.2 | 121.5 | 124.7 | 2.3 |
| LE12H255Z | 77.5 | 71.5 | 83.3 | 77.4 | 7.6 | 89.3 | 89.6 | 88.9 | 89.3 | 0.4 |
| LE12H256Z | 94.4 | 81.0 | 93.5 | 89.6 | 8.4 | 107.5 | 105.8 | 104.6 | 106.0 | 1.4 |
| LE12H302Z | 91.7 | n.a. | n.a. | n.a. | n.a. | 176.7 | n.a. | n.a. | n.a. | n.a. |
| LE12H303Z | 86.1 | n.a. | n.a. | n.a. | n.a. | 176.5 | n.a. | n.a. | n.a. | n.a. |
| LE12H304Z | 62.2 | n.a. | n.a. | n.a. | n.a. | 180.2 | n.a. | n.a. | n.a. | n.a. |

Results of the total N-glycan analysis

| N-glycan structure | | LE12H252Z | | LE12H254Z | | LE12H255Z | |
|---|---|---|---|---|---|---|---|
| | | Eluate | 2M wash | Eluate | 2M wash | Eluate | 2M wash |
| GnMF | | 3.1 | 4.0 | 3.5 | 2.5 | 4.7 | 3.1 |
| AMF | | 3.3 | 3.8 | 3.6 | 3.5 | 4.0 | 3.6 |
| GnGnF | | 11.3 | 9.0 | 10.8 | 7.4 | 10.4 | 7.6 |
| AGn | | 1.8 | 2.0 | 1.5 | 1.9 | 2.0 | 1.2 |
| AGnF | | 25.8 | 23.5 | 26.5 | 22.3 | 27.5 | 20.7 |
| GnGnFbi | | 3.8 | 3.9 | 3.3 | 2.9 | 4.5 | 3.8 |
| AAF | | 14.9 | 20.4 | 19.4 | 18.5 | 17.2 | 19.8 |
| AGnFbi | | 9.0 | 8.6 | 7.3 | 5.8 | 6.7 | 8.3 |
| NaGnF | | 4.6 | 2.3 | 2.4 | 3.9 | 2.6 | 2.2 |
| NaA | | 1.4 | 2.5 | 1.7 | 2.6 | 1.6 | 2.3 |
| AAFbi | | 2.2 | 1.5 | 1.9 | 2.4 | 2.0 | 2.0 |
| NaAF | | 14.5 | 14.9 | 11.9 | 18.3 | 12.0 | 19.2 |
| NaGnFbi | | 1.0 | 1.2 | 1.6 | 1.8 | 1.5 | 2.2 |
| NaNa | | 0.7 | 2.0 | 1.2 | 4.0 | 0.9 | 2.1 |
| NaAFbi | | 0.9 | 0.0 | 0.7 | 0.4 | 0.6 | 0.4 |
| NaNaF | | 2.8 | 0.6 | 3.3 | 2.5 | 2.4 | 1.9 |
| Neutral N-glycans | | 76.4 | 79.1 | 79.6 | 69.6 | 80.6 | 72.4 |
| Monosialylated N-glycans | | 20.1 | 18.3 | 15.9 | 23.9 | 16.0 | 23.6 |
| Disialylated N-glycans | | 3.5 | 2.6 | 4.5 | 6.5 | 3.4 | 4.0 |
| Sialylated N-glycans | | 23.6 | 20.9 | 20.4 | 30.4 | 19.4 | 27.6 |

GcNAc ■  Gal ○  Neu5Ac ◆
Man ●  Fuc ▲

IgG1 Fc N-glycan analysis

| N-Glycan structure | | M/z | LE12H252Z | | LE12H254Z | | LE12H255Z | |
|---|---|---|---|---|---|---|---|---|
| | | | Eluate | 2M wash | Eluate | 2M wash | Eluate | 2M wash |
| MGnF | | 2431.4 | 6.3 | 6.0 | 6.5 | 5.8 | 5.6 | 5.0 |
| MAF | | 2593.5 | 4.4 | 5.0 | 5.0 | 4.4 | 4.7 | 4.7 |
| GnGnF | | 2634.7 | 15.7 | 12.4 | 14.0 | 10.8 | 13.5 | 11.3 |
| AGn | | 2650.7 | 3.0 | 3.2 | 2.8 | 3.2 | 3.0 | 3.6 |
| AGnF | | 2796.8 | 26.0 | 22.6 | 26.5 | 23.2 | 29.5 | 25.3 |
| GnGnFbi | | 2837.8 | 4.4 | 4.0 | 3.5 | 3.5 | 3.7 | 3.6 |
| AAF | | 2958.8 | 18.0 | 20.8 | 19.7 | 21.7 | 19.1 | 20.9 |
| AGnFbi | | 2999.9 | 8.0 | 7.9 | 7.0 | 7.7 | 7.1 | 7.6 |
| GnNaF | | 3087.9 | 1.9 | 1.9 | 1.8 | 1.8 | 1.9 | 2.0 |
| AAFbi | | 3161.9 | 2.3 | 2.8 | 2.0 | 2.6 | 2.0 | 2.6 |
| ANaF | | 3249.9 | 10.0 | 13.4 | 11.2 | 15.1 | 9.9 | 13.3 |
| Sialylated Fc IgG1 N-glycans | | | 11.8 | 15.3 | 13.0 | 17.0 | 11.9 | 15.3 |

GcNAc ■  Gal ○  NeuSAc ◆
Man ●  Fuc ▲

Figure 14

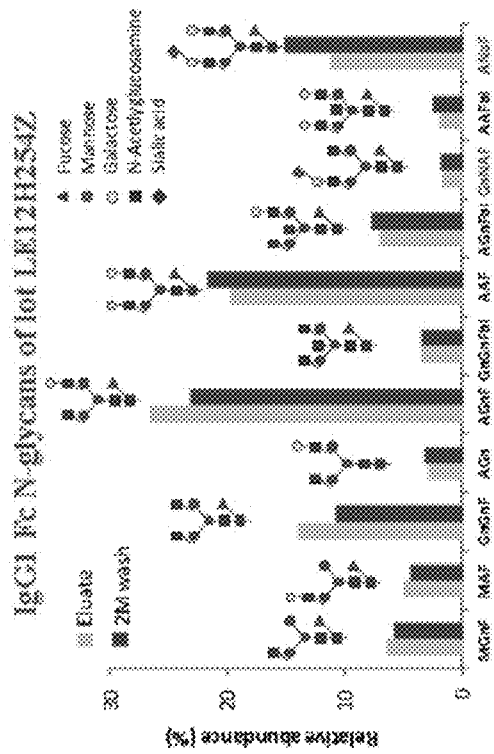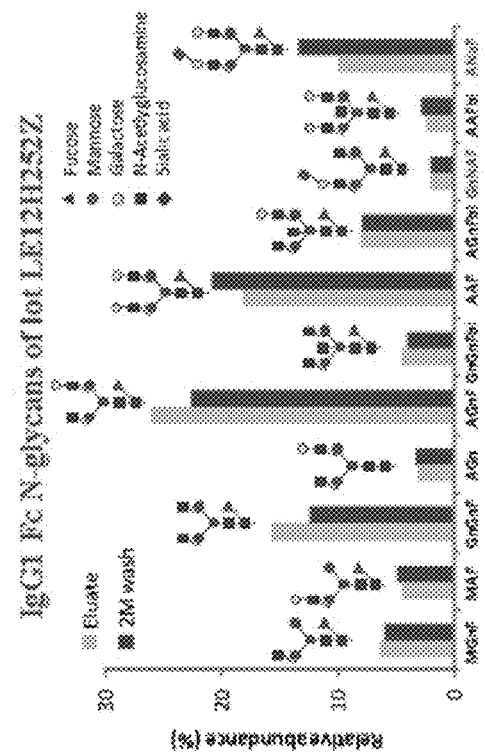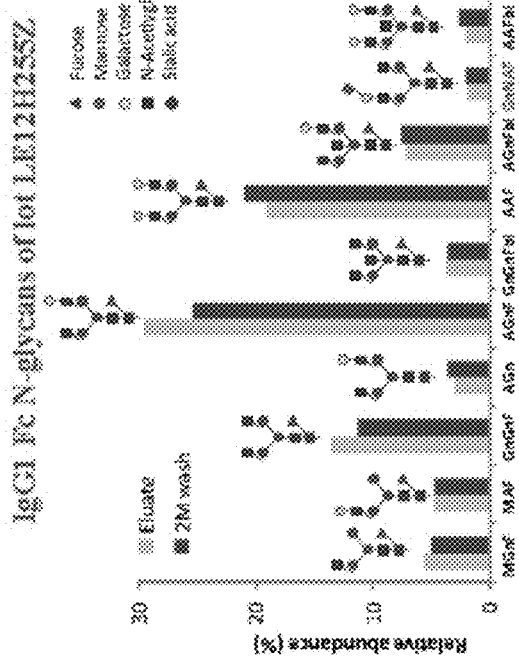
Figure 15A
Figure 15B
Figure 15C 10,738,107 B2

METHODS TO PRODUCE A HUMAN PLASMA-DERIVED IGG PREPARATION ENRICHED IN BRAIN DISEASE-RELATED NATURAL IGGS

CROSS-REFERENCES TO RELATED APPLICATIONS

This application is a Divisional of U.S. patent application Ser. No. 14/213,585, filed Mar. 14, 2014, which claims priority to U.S. Provisional Patent Application Ser. No. 61/794,378, filed Mar. 15, 2013, the disclosure of which is hereby incorporated herein by reference in its entirety for all purposes.

BACKGROUND OF THE INVENTION

Alzheimer's disease is a common form of age-related dementia that causes gradual loss of cognitive function, including memory and critical thinking abilities. Alzheimer's disease is diagnosed clinically by through a finding of progressive memory loss and decrease in cognitive abilities. However, confirmation of Alzheimer's disease does not occur until after death.

Alzheimer's disease is becoming more prevalent in developed nations, where an increase in the population of elder persons has occurred due in part to improved healthcare. While less than 1% of the population under the age of 60 is affected by Alzheimer's, it is estimated that 25% to 33% of persons develop some form of Alzheimer's by the age of 85. As of 2012, 5.4 million Americans were diagnosed with Alzheimer's. As life expectancy continues to increase worldwide, the prevalence of Alzheimer's and other age-related dementia will likely continue to grow as well.

Histopathologically, this neurodegenerative disease is characterized by the formation of amyloid plaques, neurofibrillary tangles, amyloid angiopathy, and granolovacuolar degeneration in the cerebral cortex (Mirra et al., *Arch Pathol Lab Med.*, 117:132-144 (1993); Perl D P, *Neurol Clin.*, 18:847-864 (2000)). The characteristic amyloid plaques, used to confirm Alzheimer's disease post-mortem, are formed largely by deposition of a small amyloid-beta (Aβ) peptide derived from the amyloid precursor protein (APP).

To date, the U.S. Food and Drug Administration (FDA) has approved two types of medications for the management of Alzheimer's disease: cholinesterase inhibitors, including Aricept® (donepezil), Exelon (rivastigmine), Razadyne (galantamine), and Cognex (tacrine); and the NMDA-type glutamate receptor inhibitor memantine (marketed under a number of different brands). Although a cure for Alzheimer's disease has not been identified, these therapies serve to alleviate cognitive symptoms such as memory loss, confusion, and loss of critical thinking abilities in subjects diagnosed with age-related dementia (e.g., Alzheimer's disease). In all, it is estimated that healthcare spending on Alzheimer's disease and related age-related dementias in 2012 will be $200 billion in the United States alone (*Factsheet*, Alzheimer's Association, March 2012).

In addition to these approved therapies, several studies have suggested that pooled intravenous immunoglobulin (IVIG) is effective in slowing the progression of symptoms in Alzheimer's patients (Dodel R C et al., *J Neurol Neurosurg Psychiatry*, October; 75(10):1472-4 (2004); Magga J. et al., *J Neuroinflammation*, December 7; 7:90 (1997); Relkin N R et al., *Neurobiol Aging*, 30(11):1728-36 (2008); Puli L. et al., *J Neuroinflammation* May 29; 9:105 (2012)).

It has long been recognized that human plasma contains anti-amyloid beta (anti-Aβ) antibodies. For example, anti-Aβ antibody activity has been detected in the blood of normal adults of various ages and patients with Alzheimer's disease (Weksler et al., Exp Gerontol., 37:943-948 (2002); Hyman et al., Ann Neurol., 49:808-810.5 (2001); Mruthinti et al., Neurobiol Aging., 25:1023-1032 (2004); Nath et al., Neuromolecular Med., 3:29-39 (2003); and Sohn et al., Frontiers in Bioscience., 14:3879-3883 (2009)). Because misfolding and aggregation of Aβ polypeptides is central to the pathogenesis of Alzheimer's disease, it is thought that anti-Aβ antibodies present in commercial IVIG preparations may be largely responsible for the positive results shown in preliminary studies on IVIG treatment of symptoms in Alzheimer's patients. Thus, a plasma-derived IgG preparation enriched in anti-Aβ antibodies is desirable.

US Patent Application Publication No. 2002/0009445, by Du and Dodel, suggests that Aβ-affinity chromatography can be used to isolate anti-Aβ antibodies from human plasma. However, human plasma is already a limiting resource in the manufacture of important therapeutic compositions, such as immunoglobulin G (e.g., IVIG or IgG for subcutaneous administration), because it is provided through donations. Thus, significant portions of available human plasma cannot be allocated for use solely in the manufacture of new plasma-derived therapeutics with lesser established commercial markets, such as polyclonal anti-Aβ immunoglobulin G. Furthermore, integration of a new affinity purification step into existing manufacturing processes for plasma-derived therapeutics (e.g., IgG) may have unforeseen consequences for the final therapeutic product or manufacturing yield. In addition to requiring a complete revalidation and possible redesign of key IgG manufacturing processes, regulatory re-approval of the manufacturing procedures from key regulatory agencies would be required.

Thus, a need remains for methods of preparing plasma-derived immunoglobulin G compositions enriched in anti-brain disease-related protein antibodies, such as anti-Aβ, anti-RAGE, and/or anti-α-synuclein antibodies from the existing supply of plasma donations. Advantageously, the present disclosure fulfills these and other needs by providing methods for manufacturing IgG compositions enriched in anti-brain disease-related protein antibodies from fractions produced during the manufacture of commercial IgG therapeutics, without disrupting and/or modifying the underlying manufacturing process.

BRIEF SUMMARY OF INVENTION

Among other aspects, the present disclosure provides methods for the manufacture of plasma-derived immunoglobulin G compositions highly enriched for anti-brain disease related protein antibodies (e.g., anti-Aβ, anti-RAGE, and anti-α-synuclein antibodies). Advantageously, the methods provided do not affect the manufacturing processes or capabilities for producing plasma-derived IgG therapeutics.

The methods and compositions provided herein are based in part on the surprising discovery that anti-brain disease-related protein IgG antibodies present in human plasma (e.g., anti-Aβ, anti-RAGE, and anti-α-synuclein antibodies) bind to cation exchange materials with higher affinity than do most IgG antibodies present in human plasma. In some aspects, this discovery is exploited to provide methods for isolating anti-brain disease-related protein antibodies that include steps of binding total IgG from a plasma fraction to a cation exchange material, eluting the bulk of the IgG from the cation exchange material in a first eluate using a first elution buffer, and subsequently eluting IgG remaining bound to the cation exchange material in a second eluate using a second elution buffer, where the second eluate is enriched in anti-brain disease-related protein antibodies (e.g., anti-Aβ, anti-RAGE, and anti-α-synuclein antibodies).

In other aspects, plasma-derived IgG compositions enriched in anti-brain disease-related protein antibodies (e.g., anti-Aβ, anti-RAGE, and anti-α-synuclein antibodies), obtainable by the methods described herein, are provided. In yet other aspects, the plasma-derived IgG compositions enriched in anti-brain disease-related protein antibodies (e.g., anti-Aβ, anti-RAGE, and anti-α-synuclein antibodies) are used for the treatment of a brain disease and/or disorder (e.g., Alzheimer's or Parkinson's disease).

In some aspects, the disclosure provides a first method, the first method for preparing an immunoglobulin preparation enriched in brain disease-related immunoglobulins, the method includes (A) providing a plasma-derived immunoglobulin composition comprising IgG immunoglobulins, the IgG immunoglobulins including an anti-amyloid beta (anti-Aβ) immunoglobulin, an anti-RAGE immunoglobulin, an anti-α-synuclein immunoglobulin, or another immunoglobulin specific to a brain disease-related protein. The method further includes (B) binding the IgG immunoglobulins to a cation exchange material. The method further includes (C) eluting a majority of the bound IgG immunoglobulins from the cation exchange material, in a first cation exchange elution step, using a first cation exchange elution buffer having a pH of 4.0 to 10.0 and a conductivity of 3.0 mS/cm to 16.0 mS/cm. The method further includes (D) eluting IgG immunoglobulins remaining bound to the cation exchange material, in a second cation exchange elution step, using a second cation exchange elution buffer having a pH of 4.0 to 10.0 and a conductivity of 10.0 mS/cm to 300.0 mS/cm. The method further includes (E) recovering an eluate enriched in anti-amyloid beta (anti-Aβ) immunoglobulins, anti-RAGE immunoglobulins, anti-α-synuclein immunoglobulins, other immunoglobulins specific to a brain disease-related protein, or a combination thereof.

In some aspects, the disclosure provides a second method, the second method for preparing an immunoglobulin preparation enriched in brain disease-related immunoglobulins, the method includes (A) providing a plasma-derived immunoglobulin composition comprising IgG immunoglobulins, the IgG immunoglobulins including an anti-amyloid beta (anti-Aβ) immunoglobulin, an anti-RAGE immunoglobulin, an anti-α-synuclein immunoglobulin, or another immunoglobulin specific to a brain disease-related protein. The method further includes (B) binding the IgG immunoglobulins to a weak cation exchange material. The method further includes (C) eluting a majority of the bound IgG immunoglobulins from the cation exchange material, in a first cation exchange elution step, using a first cation exchange elution buffer having a pH of 4.0 to 10.0 and a conductivity of 3.0 mS/cm to 16.0 mS/cm. The method further includes (D) eluting IgG immunoglobulins remaining bound to the cation exchange material, in a second cation exchange elution step, using a second cation exchange elution buffer having a pH of 4.0 to 10.0 and a conductivity of 80.0 mS/cm to 120.0 mS/cm. The method further includes (E) recovering an eluate enriched in anti-amyloid beta (anti-Aβ) immunoglobulins, anti-RAGE immunoglobulins, anti-α-synuclein immunoglobulins, other immunoglobulins specific to a brain disease-related protein, or a combination thereof.

In some embodiments of the methods described above, the plasma-derived immunoglobulin composition provided in (A) includes an anti-amyloid beta (anti-Aβ) immunoglobulin.

In some embodiments of the methods described above, the plasma-derived immunoglobulin composition provided in (A) includes an anti-RAGE immunoglobulin.

In some embodiments of the methods described above, the plasma-derived immunoglobulin composition provided in (A) includes an anti-α-synuclein immunoglobulin.

In some embodiments of the methods described above, the plasma-derived immunoglobulin composition provided in (A) includes an immunoglobulin specific to a brain disease-related protein selected from major prion protein (PrP), huntingtin (HD), prolactin (PRL), beta 2 microglobulin (β2M), microtubule-associated protein tau (tau), ubiquitin (UBB; UBC), and cystatin C (CST3).

In some embodiments of the methods described above, the brain disease is a neurodegenerative brain disorder.

In some embodiments of the methods described above, the plasma-derived immunoglobulin composition provided in (A) has a higher titer of an anti-amyloid beta (anti-Aβ) immunoglobulin, an anti-RAGE immunoglobulin, an anti-α-synuclein immunoglobulin, or another immunoglobulin specific to a brain disease-related protein, as compared to the titer of a plasma-derived immunoglobulin composition prepared from a plasma pool containing plasma from 1,000 random donors.

In some embodiments of the methods described above, the cation exchange material is a weak cation exchange material.

In some embodiments of the methods described above, the cation exchange material is a carboxymethyl cation exchange resin.

In some embodiments of the methods described above, the first cation exchange elution buffer has a pH of 7.0 to 9.5.

In some embodiments of the methods described above, the first cation exchange elution buffer has a pH of 8.0 to 9.0.

In some embodiments of the methods described above, the first cation exchange elution buffer has a conductivity of 4.0 mS/cm to 15.0 mS/cm.

In some embodiments of the methods described above, the first cation exchange elution buffer has a conductivity of 5.0 mS/cm to 8.0 mS/cm.

In some embodiments of the methods described above, the first cation exchange elution buffer has a pH of 8.5±0.2 and a conductivity of 5.0±1 mS/cm.

In some embodiments of the methods described above, the second cation exchange elution buffer has a pH of 7.0 to 9.5.

In some embodiments of the methods described above, the second cation exchange elution buffer has a pH of 8.0 to 9.0.

In some embodiments of the methods described above, the second cation exchange elution buffer has a conductivity of 80 mS/cm to 150 mS/cm.

In some embodiments of the methods described above, the second cation exchange elution buffer has a conductivity of 80 mS/cm to 120 mS/cm.

In some embodiments of the methods described above, the plasma-derived immunoglobulin composition is prepared by a method that includes an alcohol precipitation step.

In some embodiments of the methods described above, the alcohol precipitation step includes formation of precipitate selected from the group consisting of a Fraction I precipitate, a Cohn Fraction II precipitate, a Cohn Fraction II+III precipitate, a Cohn Fraction I+II+III precipitate, a precipitate G, a Kistler-Nitschmann precipitate A, and a Kistler-Nitschmann gamma-globulin precipitate.

In some embodiments of the methods described above, the plasma-derived immunoglobulin composition provided in step (A) is a suspended precipitate G.

In some embodiments of the methods described above, the plasma-derived immunoglobulin composition provided in step (A) is a Fraction I supernatant.

In some embodiments of the methods described above, the plasma-derived immunoglobulin composition provided in step (A) is a plasma fraction that has been enriched by at least one prior chromatographic step.

In some embodiments of the methods described above, the at least one prior chromatographic step is an anion exchange chromatographic step.

In some embodiments of the methods described above, the methods further include enrichment of immunoglobulin G in the second cation exchange eluate.

In some embodiments of the methods described above, the enrichment of immunoglobulin G in the second cation exchange eluate includes (F) reducing the conductivity of the eluate recovered in step (E) to a final conductivity of no more than 15 mS/cm, thereby forming a reduced conductivity IgG composition.

In some embodiments of the methods described above, the enrichment of immunoglobulin G in the second cation exchange eluate includes cation exchange chromatography.

In some embodiments of the methods described above, the enrichment of immunoglobulin G in the second cation exchange eluate includes (G) binding immunoglobulin G from the second cation exchange eluate to a second cation exchange material under solution conditions comprising a pH of 4.0 to 10.0 and a conductivity of 1 to 15 mS/cm, (H) eluting bound immunoglobulin G from the cation exchange material, in a third cation exchange elution step, using a third cation exchange elution buffer having a pH of 4.0 to 10.0 and a conductivity of 15.0 mS/cm to 300 mS/cm, and (I) recovering a third cation exchange eluate, the third cation exchange eluate enriched in anti-amyloid beta (anti-Aβ) immunoglobulins, anti-RAGE immunoglobulins, anti-α-synuclein immunoglobulins, other immunoglobulins specific to a brain disease-related protein, or a combination thereof.

In some embodiments of the methods described above, the second cation exchange material is a weak cation exchange resin.

In some embodiments of the methods described above, the second cation exchange material is a carboxymethyl cation exchange resin.

In some embodiments of the methods described above, the enrichment of immunoglobulin G in the second cation exchange eluate includes anion exchange chromatography.

In some embodiments of the methods described above, the enrichment of immunoglobulin G in the second cation exchange eluate includes (J) applying immunoglobulin G to an anion exchange column, in an anion exchange flow through step, under solution conditions comprising a pH of 5.0 to 8.0 and a conductivity of 0.5 mS/cm to 5.0 mS/cm, and (K) recovering a flow-through fraction from anion exchange flow-through step (J), the flow-through fraction enriched in anti-amyloid beta (anti-Aβ) immunoglobulins, anti-RAGE immunoglobulins, anti-α-synuclein immunoglobulins, other immunoglobulins specific to a brain disease-related protein, or a combination thereof.

In some embodiments of the methods described above, the solution conditions used in step (J) include a pH of 6.0 to 7.0.

In some embodiments of the methods described above, the solution conditions used in step (J) include a pH of 6.2 to 6.6.

In some embodiments of the methods described above, the solution conditions used in step (J) include a conductivity of 1 mS/cm to 4.5 mS/cm.

In some embodiments of the methods described above, the methods also include (L) reducing the viral load of the composition by nanofiltration.

In some aspects, the disclosure provides a third method, the third method for preparing an immunoglobulin preparation enriched in brain disease-related immunoglobulins, the third method including (A) providing a plasma-derived immunoglobulin composition comprising IgG immunoglobulins, the IgG immunoglobulins including an anti-amyloid beta (anti-Aβ) immunoglobulin, an anti-RAGE immunoglobulin, an anti-α-synuclein immunoglobulin, or another immunoglobulin specific to a brain disease-related protein. The method further includes (B) applying the plasma-derived immunoglobulin composition to an anion exchange column under solution conditions that promote binding of a majority of IgG immunoglobulins in the plasma-derived immunoglobulin composition to anion exchange material in the anion exchange column. The method further includes (C) collecting a flow-through fraction from the applying in step (B), the flow through fraction enriched in anti-amyloid beta (anti-Aβ) immunoglobulins, anti-RAGE immunoglobulins, anti-α-synuclein immunoglobulins, other immunoglobulins specific to a brain disease-related protein, or a combination thereof.

In some embodiments of the third method described above, the plasma-derived immunoglobulin composition provided in (A) includes an anti-amyloid beta (anti-Aβ) immunoglobulin.

In some embodiments of the third method described above, the plasma-derived immunoglobulin composition provided in (A) includes an anti-RAGE immunoglobulin.

In some embodiments of the third method described above, the plasma-derived immunoglobulin composition provided in (A) includes an anti-α-synuclein immunoglobulin.

In some embodiments of the third method described above, the plasma-derived immunoglobulin composition provided in (A) includes an immunoglobulin specific to a brain disease-related protein selected from the group consisting of major prion protein (PrP), huntingtin (HD), prolactin (PRL), beta 2 microglobulin (β2M), microtubule-associated protein tau (tau), ubiquitin (UBB; UBC), and cystatin C (CST3).

In some embodiments of the third method described above, the plasma-derived immunoglobulin composition provided in (A) has a higher titer of an anti-amyloid beta (anti-Aβ) immunoglobulin, an anti-RAGE immunoglobulin, an anti-α-synuclein immunoglobulin, or another immunoglobulin specific to a brain disease-related protein, as compared to the titer of a plasma-derived immunoglobulin composition prepared from a plasma pool containing plasma from 1,000 random donors.

In some embodiments of the third method described above, the plasma-derived immunoglobulin composition provided in (A) is prepared by a method that includes an alcohol precipitation step.

In some embodiments of the third method described above, the alcohol precipitation step includes formation of precipitate selected from the group consisting of a Fraction I precipitate, a Cohn Fraction II precipitate, a Cohn Fraction II+III precipitate, a Cohn Fraction I+II+III precipitate, a precipitate G, a Kistler-Nitschmann precipitate A, and a Kistler-Nitschmann gamma-globulin precipitate.

In some embodiments of the third method described above, the plasma-derived immunoglobulin composition provided in step (A) is a suspended precipitate G.

In some embodiments of the third method described above, the plasma-derived immunoglobulin composition provided in step (A) is a Fraction I supernatant.

In some embodiments of the third method described above, the plasma-derived immunoglobulin composition provided in step (A) is a plasma fraction that has been enriched by at least one prior chromatographic step.

In some embodiments of the third method described above, the at least one prior chromatographic step is a cation exchange chromatographic step.

In some embodiments of the third method described above, the methods further include enrichment of immunoglobulin G in the anion exchange flow through fraction.

In some embodiments of the third method described above, the enrichment of immunoglobulin G in the anion exchange flow through fraction includes (D) reducing the conductivity of the eluate recovered in step (C) to a final conductivity of no more than 15 mS/cm, thereby forming a reduced conductivity IgG composition.

In some embodiments of the third method described above, the enrichment of immunoglobulin G in the anion exchange flow through fraction includes cation exchange chromatography.

In some embodiments of the third method described above, the enrichment of immunoglobulin G in the anion exchange flow through fraction includes (E) binding immunoglobulin G from the anion exchange flow through fraction to a cation exchange material under solution conditions including a pH of 4.0 to 10.0 and a conductivity of 1 to 15 mS/cm, (F) eluting bound immunoglobulin G from the cation exchange material, in a cation exchange elution step, using a cation exchange elution buffer having a pH of 4.0 to 10.0 and a conductivity of 15.0 mS/cm to 300 mS/cm, and (G) recovering a cation exchange eluate, the cation exchange eluate enriched in anti-amyloid beta (anti-Aβ) immunoglobulins, anti-RAGE immunoglobulins, anti-α-synuclein immunoglobulins, other immunoglobulins specific to a brain disease-related protein, or a combination thereof.

In some embodiments of the third method described above, the cation exchange material is a weak cation exchange resin.

In some embodiments of the third method described above, the cation exchange material is a carboxymethyl cation exchange resin.

In some embodiments of the third method described above, the enrichment of immunoglobulin G in the cation exchange eluate includes anion exchange chromatography.

In some embodiments of the third method described above, the enrichment of immunoglobulin G in the cation exchange eluate includes (H) applying immunoglobulin G to a second anion exchange column, in a second anion exchange flow through step, under solution conditions including a pH of 5.0 to 8.0 and a conductivity of 0.5 mS/cm to 5.0 mS/cm, and (I) recovering a flow-through fraction from the second anion exchange flow-through step (H), the flow-through fraction enriched in anti-amyloid beta (anti-Aβ) immunoglobulins, anti-RAGE immunoglobulins, anti-α-synuclein immunoglobulins, other immunoglobulins specific to a brain disease-related protein, or a combination thereof.

In some embodiments of the third method described above, the solution conditions used in step (H) include a pH of 6.0 to 7.0.

In some embodiments of the third method described above, the solution conditions used in step (H) include a pH of 6.2 to 6.6.

In some embodiments of the third method described above, the solution conditions used in step (H) include a conductivity of 1 mS/cm to 4.5 mS/cm.

In some embodiments of the third method described above, the method also includes (K) reducing the viral load of the composition by nanofiltration.

In some aspects, the disclosure provides a fourth method, the fourth method for preparing an immunoglobulin preparation enriched in brain disease-related immunoglobulins, the method including admixing a first immunoglobulin composition prepared according to any one of the preceding embodiments with a second immunoglobulin preparation that is not enriched in brain disease-related immunoglobulin.

In some embodiments of the fourth method described above, the first immunoglobulin composition is admixed with the second immunoglobulin preparation at a ratio from 4:1 to 1:100.

In some embodiments of the fourth method described above, the first immunoglobulin composition is admixed with the second immunoglobulin preparation at a ratio of 4:1 to 1:1.

In some embodiments of the fourth method described above, the first immunoglobulin composition is admixed with the second immunoglobulin preparation at a ratio of 1:1 to 1:100.

In some embodiments of the fourth method described above, the first immunoglobulin composition is admixed with the second immunoglobulin preparation at a ratio of 1:1 to 1:10.

In some aspects, the disclosure provides an immunoglobulin composition enriched in brain disease-related immunoglobulins prepared according to any of the methods described above.

In some embodiments of the IgG compositions described above, the composition in enriched in anti-amyloid beta (anti-Aβ) immunoglobulins. In some embodiments of the IgG compositions described above, the composition in enriched in $IgG_3$ subclass anti-amyloid beta (anti-Aβ) immunoglobulins.

In some embodiments of the IgG compositions described above, the composition in enriched in anti-RAGE immunoglobulins. In some embodiments of the IgG compositions described above, the composition in enriched in $IgG_1$ and/or $IgG_4$ subclass anti-RAGE immunoglobulins.

In some embodiments of the IgG compositions described above, the composition in enriched in anti-α-synuclein immunoglobulins.

In some embodiments of the IgG compositions described above, the composition in enriched in other immunoglobulins specific to a brain disease-related protein, or a combination thereof. In some embodiments of the IgG compositions described above, the other immunoglobulin specific to a brain disease-related protein is an immunoglobulin IgG that specifically binds to a protein selected from major prion protein (PrP), huntingtin (HD), prolactin (PRL), beta 2 microglobulin (β2M), microtubule-associated protein tau (tau), ubiquitin (UBB; UBC), and cystatin C (CST3).

In some embodiments of the IgG compositions described above, the composition is enriched in immunoglobulins of the $IgG_3$ subclass.

In some embodiments of the IgG compositions described above, the composition is enriched in immunoglobulins having mono-sialylated biantennary ANaF N-glycans. In some embodiments of the IgG compositions described above, the composition is enriched in $IgG_1$ subclass immunoglobulins having mono-sialylated biantennary ANaF N-glycans.

In some embodiments of the IgG compositions described above, the composition is enriched in immunoglobulins having bi-galactosylated biantennary AFF N-glycans. In some embodiments of the IgG compositions described above, the composition is enriched in $IgG_1$ subclass immunoglobulins having bi-galactosylated biantennary AFF N-glycans.

In some aspects, the disclosure provides a fifth method, the fifth method for treating a brain disease or disorder including administering a therapeutically effective amount of a brain disease-related immunoglobulin composition enriched in anti-amyloid beta (anti-Aβ) immunoglobulins, anti-RAGE immunoglobulins, anti-α-synuclein immunoglobulins, other immunoglobulins specific to a brain disease-related protein, or a combination thereof to a subject in need thereof.

In some embodiments of the fifth method described above, the brain disease related immunoglobulin composition is prepared by any of the methods described above.

In some embodiments of the fifth method described above, the brain disease or disorder treated is selected from the group consisting of Alzheimer's disease, Parkinson's disease, transmissible spongiform encephalopathy, Huntington's disease, a prolactinoma, dialysis related amyloidosis, cerebral amyloid angiopathy, Pick's disease, and Icelandic-type Cerebral amyloid angiopathy.

In some embodiments of the fifth method described above, the disease is Alzheimer's disease.

In some embodiments of the fifth method described above, the disease is Parkinson's disease.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 2A-2B report data obtained from anti-Aβ40 fibril ELISAs performed under isotonic (FIG. 2A) or low ionic strength (FIG. 2B) conditions with matching samples of the cation exchange eluate and corresponding 2 M wash fraction generated during preparation of a plasma-derived IgG composition.

FIG. 3A-3B illustrate the relative concentrations of anti-Aβ40 fibril IgG antibodies in matching samples of the cation exchange eluate and corresponding 2 M wash fraction generated during preparation of a plasma-derived IgG composition, as determined under isotonic (FIG. 3A) or low ionic strength (FIG. 3B) conditions.

FIG. 4A-4B report data obtained from anti-Aβ40 CAPS ELISAs performed under isotonic (FIG. 4A) or low ionic strength (FIG. 4B) conditions with matching samples of the cation exchange eluate and corresponding 2 M wash fraction generated during preparation of a plasma-derived IgG composition.

FIG. 6A-6B report data obtained from anti-Aβ42 monomer ELISAs performed under isotonic (FIG. 6A) or low ionic strength (FIG. 6B) conditions with matching samples of the cation exchange eluate and corresponding 2 M wash fraction generated during preparation of a plasma-derived IgG composition.

FIG. 9A reports the subclass distribution for each of the matching samples. FIG. 9B illustrates the average subclass distribution in all of the matching samples.

FIG. 10A reports the IgA and IgM content of each of the matching samples. FIG. 10B illustrates the relative IgA concentration in each of the matching samples. FIG. 10C illustrates the relative IgM concentration in each of the matching samples.

FIG. 11A illustrates the average size distribution in all of the matching samples. FIG. 11B reports the size distribution of protein in each of the matching samples.

FIG. 14 reports the results of $IgG_1$ Fc-specific N-glycan analysis on matching samples of the cation exchange eluate and corresponding 2 M wash fraction generated during preparation of a plasma-derived IgG composition.

FIG. 15A-15C illustrate the relative concentration of $IgG_1$ Fc-specific N-glycans present in matching samples LE12H252Z (FIG. 15A), LE12H254Z (FIG. 15B), and LE12H255Z (FIG. 15C) of the cation exchange eluate and corresponding 2 M wash fraction generated during preparation of a plasma-derived IgG composition.

DETAILED DESCRIPTION OF INVENTION

I. Introduction

The preparation of plasma-derived IgG compositions enriched in anti-brain disease-related protein antibodies, such as anti-Aβ, anti-RAGE, and anti-α-synuclein antibodies, is highly desirable due to its therapeutic potential for treating diseases such as Alzheimer's and Parkinson's disease. Unfortunately, efforts to prepare such enriched plasma-derived IgG preparations have failed to date. For example, to the knowledge of the inventors, no natural IgG preparations with highly enriched anti-Aβ antibody titer are available. Furthermore, no methods are known that could be used to enrich plasma-derived anti-Aβ IgGs in large-scale, without impacting commercial processes used to manufacture plasma-derived IgG therapeutics, such as IVIG and IgG for subcutaneous administration.

In one aspect, the present disclosure provides methods for enriching such antibodies from chromatographic fractions prepared, but not used, during the manufacture of immunoglobulin G products, such as intravenous immunoglobulin G (IVIG). Advantageously, it was found that anti-brain disease-related protein IgG antibodies (e.g., anti-Aβ, anti-RAGE, and anti-α-synuclein antibodies) bind to cation exchange materials with higher affinity than other IgG antibodies present in plasma.

For example, cation exchange chromatography is used to enrich IgGs recovered from a Fraction II+III ethanol precipitate (Teschner W. et al., Vox Sanguinis 92, 42-55 (2006), the disclosure of which is hereby expressly incorporated by reference in its entirety for all purposes, and in particular for all teachings related to the use of alcohol fractionation and chromatographic enrichment for the preparation of plasma-derived IgG compositions). In this step, IgGs are bound to a weak cation exchange material (e.g., a carboxymethyl cation exchange resin), the bound resin is washed, and the bulk of the bound IgG content is eluted off of the column by increasing the ionic strength and pH of the solution conditions (e.g., by applying an elution buffer to the bound resin). After elution of the bulk of the bound IgG, the cation exchange resin is regenerated by stripping any molecules remaining bound under extreme ionic strength conditions (e.g., with a solution containing 2 M sodium chloride), allowing the resin to be reused in subsequent manufacturing processes.

Figure 8A:
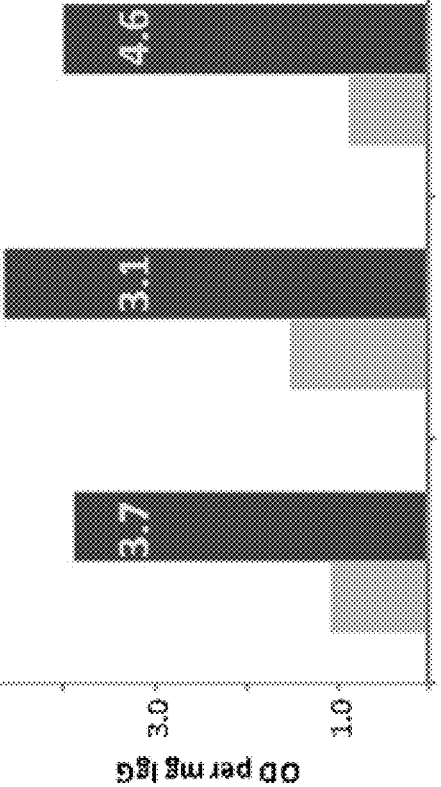
FIG. 8A-8B illustrate the average relative concentrations of anti-Aβ40 fibril, anti-Aβ40 CAPS, and anti-Aβ42 monomer IgG antibodies in matching samples of the cation exchange eluate and corresponding 2 M wash fraction generated during preparation of a plasma-derived IgG composition, as determined under isotonic (FIG. 8A) or low ionic strength (FIG. 8B) conditions.
Figure 8B:
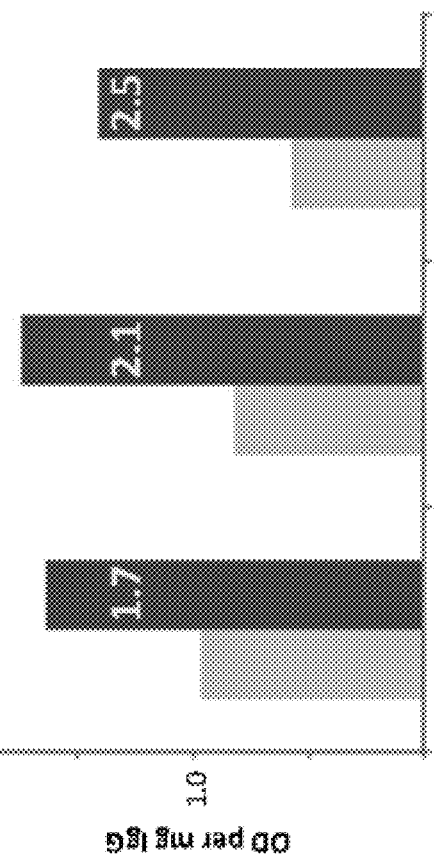

Surprisingly, it was discovered that the high salt fraction formed during this regeneration process (e.g., the "2 M wash fraction"), which contains small amounts of IgG (e.g., less than 5% of the IgG content in the starting materials), is highly enriched for anti-brain disease-related protein antibodies, such as anti-Aβ, anti-RAGE, and anti-α-synuclein antibodies. As shown in Example 2, binding activity against all tested Aβ conformers is enriched at least 2- to 4.5-fold in the 2 M wash fraction, as compared to the corresponding cation exchange eluate fraction (FIGS. 8A-8B). Further purification of these 2 M wash fractions, as described in Example 9, results in the production of highly pure plasma-derived IgG compositions (e.g., greater than 99% IgG), containing 65- to 95-fold higher binding to all tested Aβ conformers, as compared to average Aβ conformer binding in large scale plasma-derived IgG compositions prepared according to the method outlined in FIG. 1 (Table 6). Further analysis, reported in Example 9, revealed that other anti-brain disease-related protein antibodies are also highly enriched in these compositions. For example, anti-RAGE and anti-α-synuclein binding activities are 20-fold and 50-fold higher, respectively, in these compositions than in average lots of large scale plasma-derived IgG compositions prepared according to the method outlined in FIG. 1.

As will be appreciated by one of skill in the art, immunoglobulin molecules that bind strongly to a cation exchange material (e.g., the anti-brain disease-related protein IgG antibodies described herein) will bind weakly to an anion exchange material. Accordingly, in some embodiments, anti-brain disease-related protein IgG antibodies (e.g., anti-Aβ, anti-RAGE, and anti-α-synuclein antibodies) can be isolated by applying a plasma-derived IgG immunoglobulin composition to an anion exchange material (e.g., anion exchange resin) under solution conditions that promote binding of the majority of the IgG immunoglobulins to the anion exchange material, and then recovering the fraction of IgG immunoglobulins that do not bind to the anion exchange material (e.g., a flow-through fraction of an anion exchange column), which are enriched in anti-brain disease-related protein immunoglobulins.

Also provided here are methods for producing plasma-derived IgG compositions with specific titers of anti-brain disease-related immunoglobulins, by supplementing a plasma-derived total IgG composition (e.g., a commercially manufactured plasma-derived IgG compositions such as IVIG and IgG for subcutaneous administration) with an IgG composition enriched in anti-brain disease-related protein immunoglobulins described herein. In this fashion, the titer of a specific anti-brain disease-related protein immunoglobulin (e.g., an anti-Aβ immunoglobulin) can be tailored for use as a medicament for a particular indication (e.g., Alzheimer's disease).

Thus, methods for the manufacture of plasma-derived immunoglobulin G compositions highly enriched for anti-brain disease related protein antibodies (e.g., anti-Aβ, anti-RAGE, and anti-α-synuclein antibodies) are described here. These methods do not affect the manufacturing processes or capabilities for commercially produced plasma-derived IgG therapeutics.

Also provided herein are plasma-derived IgG compositions that are highly enriched for anti-brain disease related protein antibodies (e.g., anti-Aβ, anti-RAGE, and anti-α-synuclein antibodies), obtainable by the methods provided here.

In yet other aspects, methods for the treatment of brain diseases and disorders are also provided here. These methods include the administration of plasma-derived IgG compositions highly enriched for anti-brain disease related protein antibodies (e.g., anti-Aβ, anti-RAGE, and anti-α-synuclein antibodies), obtainable by the methods provided here.

II. Definitions

As used herein, the term "enriched composition" refers to a protein composition isolated from a plasma sample, in which the purity of a protein of interest (e.g., an anti-brain disease-related protein antibody, such as anti-Aβ, anti-RAGE, and/or anti-α-synuclein antibody) is higher than the purity of the protein of interest in the starting sample (e.g., pooled plasma). In some embodiments, the purity of the protein of interest in the enriched composition is at least 25% greater than the purity of the protein of interest in the starting sample. In some embodiments, the purity of the protein of interest in the enriched composition is at least 50%, 75%, 100%, 2-fold, 3-fold, 4-fold, 5-fold, 6-fold, 7-fold, 8-fold, 9-fold, 10-fold, or more greater than the purity of the protein of interest in the starting sample. For example, an enriched anti-brain disease-related protein antibody, such as anti-Aβ, anti-RAGE, and/or anti-α-synuclein antibody, composition in which 7% of the total protein is an anti-brain disease-related protein antibody, such as anti-Aβ, anti-RAGE, and/or anti-α-synuclein antibody, is 7-fold enriched as compared to a starting sample in which 1% of the total protein is an anti-brain disease-related protein antibody, such as anti-Aβ, anti-RAGE, and/or anti-α-synuclein antibody.

As used herein, the term "brain disease-related protein" refers to protein associated with a disease or disorder of the brain. For example, in some embodiments, a brain disease-related protein is a protein linked to a disease or disorder of the brain that is mis-expressed (e.g., over- or under-expressed) in the brain, mutated in a disease or disorder of the brain, abnormally located (e.g., mis-located or over-located as in the deposition of protein plaques on the cerebral cortex). Non-limiting examples of brain-disease related proteins include amyloid beta (Aβ), alpha-synuclein (SNCA), Major Prion Protein (PrP), Huntingtin (HD), Prolactin (PRL), Cystatin C (CST3), Microtubule-associated protein tau (tau), Ubiquitin (UBB; UBC), and advanced glycosylation end product-specific receptor (RAGE). Table 1 provides non-limiting examples of brain disease-related proteins and their corresponding brain disease.

TABLE 1

Exemplary brain disease-related proteins and their corresponding brain disease.

| Disease | Related Protein | GenBank Accession | UniProt Accession |
| --- | --- | --- | --- |
| Alzheimer's disease | Beta amyloid (Aβ; Abeta) | NP_000475 | P05067 |
| Parkinson's disease | Alpha-synuclein (SNCA) | NP_000336 | P37840 |
| Transmissible spongiform encephalopathy (e.g., Creutzfeldt-Jakob disease) | Major Prion Protein (PrP) | NP_000302 | P04156 |
| Huntington's Disease | Huntingtin (HD) | NP_002102 | P42858 |
| Prolactinomas | Prolactin (PRL) | NP_000939 | P01236 |
| Dialysis related amyloidosis | Beta 2 microglobulin (β2M) | NP_004039 | P61769 |
| Cerebral amyloid angiopathy | Beta amyloid (Aβ; Abeta) | NP_000475 | P05067 |
| Cerebral amyloid angiopathy (Icelandic type) | Cystatin C (CST3) | NP_000090 | P01034 |
| Alzheimer's disease | Advanced glycosylation end product-specific receptor (RAGE) | NP_001127 | Q15109 |
| Pick's Disease | Microtubule-associated protein tau (tau) | NP_001116538 | P10636 |
| Pick's Disease | Ubiquitin (UBB; UBC) | NP_061828; NP_066289 | P0CG47; P0CG48 |

Neurodegenerative CNS disorders are typically characterized by progressive dysfunction and/or cell death in the central nervous system. The hallmark of many neurodegenerative CNS disorders is the accumulation of misfolded proteins, such as beta-amyloid, tau, alpha-synuclein, and TDP-43, both intracellularly and extracellularly. Many neurodegenerative diseases are also associated with gross mitochondrial dysfunction. Common examples of neurodegenerative CNS disorders include Alzheimer's disease (AD), Parkinson's disease (PD), Huntington's disease, Amyotrophic lateral sclerosis (ALS), and Pick's disease (PiD).

As used herein, the term "neurodegenerative brain disorder" refers to a disease or disorder characterized by progressive dysfunction and/or cell death in the brain. The hallmark of many neurodegenerative brain disorders is the accumulation of misfolded proteins, such as beta-amyloid, tau, alpha-synuclein, and TDP-43, both intracellularly and extracellularly. Many neurodegenerative diseases are also associated with gross mitochondrial dysfunction in the brain. Non-limiting examples of neurodegenerative brain disorders include Alzheimer's disease, Parkinson's disease, progressive supranuclear palsy, multiple system strophy, olivopontocerebellar atrophy (OPCA), Shy-Drager syndrome, striatonigral degeneration, Huntington's disease, amyotrophic lateral sclerosis (ALS), essential tremor, cortico-basal ganlionic degeneration, Diffuse Lewy body disease, Parkinson-ALS-dementia complex of Guam, and Pick's disease. Non-limiting examples of types of cells found in the brain include neuronal cells (e.g., pyramidal, purkinje, locus ceruleus, medium spiny neurons, spindle neurons, and granule cells), interneuronal cells (e.g., basket cells, stellate cells, unipolar brush cells), and glial cells (e.g., astrocytes, oligodendrocytes, ependyma, and radial glial cells).

As used herein, the terms "high titer anti-amyloid β pooled immunoglobulin G" and "high titer anti-amyloid β pooled IgG" refer to a composition containing polyvalent immunoglobulin G (IgG) purified from the blood/plasma of multiple donors, e.g., more than fifty, or more than a hundred, or more than a thousand blood/plasma donors, having a relative titer of anti-amyloid β immunoglobulin G that is greater than the expected titer of anti-amyloid β immunoglobulins in a pooled IgG composition prepared from the blood/plasma of more than a thousand random individuals. Commercially available intravenous immunoglobulin G (IVIG) preparations contain IgGs that specifically recognize epitopes of various conformers of amyloid β, e.g., amyloid β monomers, amyloid β fibrils, and cross-linked amyloid β protein species (CAPS). It has been reported that a commercial preparation of GAM-MAGARD® LIQUID (10% Immune Globulin Infusion (Human)) contains 0.1% anti-amyloid β fibril IgG, 0.04% anti-CAPS IgG, and 0.02% anti-amyloid β monomer IgG, having $EC_{50}$ affinities of 40 nM, 40 nM, and 350 nM for their target amyloid β conformer, respectively (O'Nuallain B. et al., Biochemistry, 2008 Nov. 25; 47(47):12254-6). In some embodiments, a high titer anti-amyloid β pooled immunoglobulin G composition contains a high titer of IgG specific for one or more conformer of amyloid β. In other embodiments, a high titer anti-amyloid β pooled immunoglobulin G composition contains a high titer of IgG specific for amyloid β monomers, amyloid β fibrils, and cross-linked amyloid β protein species (CAPS).

Accordingly, in one embodiment, a high titer anti-amyloid β pooled immunoglobulin G composition contains at least 0.1% anti-amyloid β IgG (e.g., 0.1% IgG with specific affinity for any amyloid β conformer). In another embodiment, a high titer anti-amyloid β pooled immunoglobulin G composition contains at least 0.2% anti-amyloid β IgG. In yet other embodiments, a high titer anti-amyloid β pooled immunoglobulin G composition contains at least 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.5%, 2.0%, 2.5%, 3.0%, 3.5%, 4.0%, 4.5%, 5.0% or more anti-amyloid β IgG.

In one embodiment, a high titer anti-amyloid β pooled immunoglobulin G composition contains at least 0.1% anti-amyloid β fibril IgG. In another embodiment, a high titer anti-amyloid β pooled immunoglobulin G composition contains at least 0.2% anti-amyloid β fibril IgG. In yet other embodiments, a high titer anti-amyloid β pooled immunoglobulin G composition contains at least 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.5%, 2.0%, 2.5%, 3.0%, 3.5%, 4.0%, 4.5%, 5.0% or more anti-amyloid β fibril IgG.

In one embodiment, a high titer anti-amyloid β pooled immunoglobulin G composition contains at least 0.04% anti-CAPS IgG. In another embodiment, a high titer anti-amyloid β pooled immunoglobulin G composition contains at least 0.08% anti-CAPS IgG. In yet other embodiments, a high titer anti-amyloid β pooled immunoglobulin G composition contains at least 0.04%, 0.05%, 0.06%, 0.07%, 0.08%, 0.09%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.5%, 2.0%, 2.5%, 3.0%, 3.5%, 4.0%, 4.5%, 5.0% or more anti-CAPS IgG.

In one embodiment, a high titer anti-amyloid β pooled immunoglobulin G composition contains at least 0.02% anti-amyloid β monomer IgG. In another embodiment, a high titer anti-amyloid β pooled immunoglobulin G composition contains at least 0.04% anti-amyloid β monomer IgG. In yet other embodiments, a high titer anti-amyloid β pooled immunoglobulin G composition contains at least 0.02%, 0.03%, 0.04%, 0.05%, 0.06%, 0.07%, 0.08%, 0.09%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1.0%, 1.5%, 2.0%, 2.5%, 3.0%, 3.5%, 4.0%, 4.5%, 5.0% or more anti-amyloid β monomer IgG.

In one embodiment, a high titer anti-amyloid β pooled immunoglobulin G composition contains at least 2-fold greater binding activity for at least one conformer of amyloid β (e.g., an Aβ42 monomer, an Aβ40 CAPS, or an Aβ40 fibril) than does a pooled total IgG composition prepared from the blood/plasma of more than a thousand random individuals. In some embodiments, a high titer anti-amyloid β pooled immunoglobulin G composition contains at least 3-fold, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one conformer of amyloid β than does a pooled total IgG composition prepared from the blood/plasma of more than a thousand random individuals. In some embodiments, the binding activity of a high titer anti-amyloid β pooled immunoglobulin G composition is enriched for an anti-amyloid β antibody as compared to the concentration and/or activity of the anti-amyloid β antibody in a commercial plasma-derived IgG composition.

Methods that may be used to measure the binding activity of anti-Aβ antibodies (e.g., in a plasma sample or in a plasma-derived IgG composition) are known in the art, for example, as described in O'Nuallain B. et al., Biochemistry, 2008 Nov. 25; 47(47):12254-6, U.S. Patent Application Publication No. 2012/0183527, and U.S. patent application Ser. No. 13/714,309, the contents of which are hereby expressly incorporated by reference in their entireties for all purposes, and in particular for all teachings related to the detection of antibodies in biological samples, including without limitation blood, plasma, and compositions purified from plasma.

As used herein, the terms "specific binding," "antibody recognizing" an antigen, "antibody specific" for an antigen, and "antibody which binds specifically" to an antigen are used interchangeably and refer to a selective binding quality of an antibody for a specific target epitope (i.e., a particular brain disease-related protein) such that the relative $K_D$ of the antibody for the specific target epitope is at least 5-fold less, preferably 10-fold less, than the $K_D$ of the antibody for another, non-targeted ligand.

As used herein, the term "cryo-poor plasma" refers to a supernatant formed by cryo-precipitation of blood plasma (e.g., plasma from a single source or a pool of plasma from multiple sources). Cryo-precipitation is typically performed by thawing frozen plasma a temperature near freezing, e.g., at a temperature below about 10° C., preferably at a temperature no higher than about 6° C. As used herein "plasma," unless otherwise specified, refers to both recovered plasma (i.e., plasma that has been separated from whole blood ex vivo) or source plasma (i.e., plasma collected via plasmapheresis). Although cryo-precipitation is commonly performed by thawing previously frozen plasma (e.g., pooled plasma) which has already been assayed for safety and quality considerations, in some embodiments, fresh plasma may also be used. After complete thawing of the frozen plasma at low temperature, the solid cryo-precipitates are separated from the liquid supernatant (i.e., the "cryo-poor plasma") in the cold (e.g., at a temperature below about 10° C., preferably no more than 6° C.) by centrifugation, filtration, or other suitable means.

As used herein, a "Cohn pool" or "Cohn plasma pool" refers to the starting material used for the fractionation of a plasma sample or pool of plasma samples. Cohn pools include, without limitation, whole plasma, cryo-poor plasma, and pools of whole plasma, cryo-poor plasma, or a combination thereof. In some embodiments, a Cohn pool is subjected to a pre-processing step. In certain embodiments, a Cohn pool is a cryo-poor plasma sample from which one or more blood factor have been removed in a pre-processing step, for example, adsorption onto a solid phase (e.g., aluminum hydroxide or finely divided silicon dioxide) or chromatographic step (e.g., ion exchange or heparin affinity chromatography). Various blood factors, including but not limited to, Factor Eight Inhibitor Bypass Activity (FEIBA), Factor IX-complex, Factor VII-concentrate, or Antithrombin III-complex, may be isolated from the cryo-poor plasma sample prior to use as a Cohn pool for isolation of IgG (e.g., a composition of IgG enriched in anti-brain disease-related protein IgG immunoglobulins).

As used herein, a "Fraction II+III precipitate" refers to a precipitate formed by cold incubation of blood plasma or a derivative thereof (e.g., cryo-poor plasma or Fraction I supernatant) after the addition of alcohol (e.g., denatured ethanol) to a final concentration of from about 17% to about 27% (v/v) at a pH of from about 5.5 to about 7.0, and encompasses common intermediates formed during Cohn-Oncley (e.g., Fraction II+III; Cohn et al., J. Am. Chem. Soc. 68:459-75 (1946); Oncley et al., J. Am. Chem. Soc. 71:541-50 (1949), the disclosures of which are hereby expressly incorporated by reference in their entireties for all purposes) and Kistler-Nitschmann (e.g., Precipitate A; Kistler and Nitschmann, Vox Sang. 7:414-424 (1962), the disclosure of which is hereby expressly incorporated by reference in its entirety for all purposes) alcohol fractionations, and derivative fractionation schemes thereof.

In some embodiments, a "Cohn Fraction II+III precipitate" refers to a precipitate formed by cold incubation of blood plasma or a derivative thereof (e.g., cryo-poor plasma of Fraction I supernatant) after the addition of alcohol (e.g., denatured ethanol) to a final concentration of from about 17% to about 27% (v/v), preferably from about 20% to 25% (v/v) at a pH of from about 6.5 to about 7.0, and encompasses common intermediates formed during Cohn-Oncley (e.g., Fraction II+III; Cohn et al., J. Am. Chem. Soc. 68:459-75 (1946); Oncley et al., J. Am. Chem. Soc. 71:541-50 (1949), the disclosures of which are hereby expressly incorporated by reference in their entireties for all purposes) alcohol fractionation, and derivative fractionation schemes thereof.

In some embodiments, a "Kistler-Nitschmann II+III precipitate" refers to a precipitate formed by cold incubation of blood plasma or a derivative thereof (e.g., cryo-poor plasma or Supernatant B) after the addition of alcohol (e.g., denatured ethanol) to a final concentration of from about 17% to about 22% (v/v) at a pH of from about 5.5 to about 6.0, and encompasses common intermediates formed during Kistler-Nitschmann plasma fractionation (e.g., Precipitate A; Kistler and Nitschmann, Vox Sang. 7:414-424 (1962), the disclosure of which is hereby expressly incorporated by reference in its entirety for all purposes), and derivative fractionation schemes thereof.

As used herein, the term "alcohol" refers to a $C_1$-$C_5$ monohydric alcohol capable of precipitating proteins from plasma. In some embodiments, the alcohol is ethanol or methanol. In a preferred embodiment, the alcohol is a denatured ethanol (e.g., ethanol SDA 3A containing approximately 95% ethanol and 5% methanol (w/w)). In some embodiments, the alcohol concentrations used for precipitation reactions disclosed herein refer to a final concentration of a denatured ethanol. The skilled artisan will understand how to adapt these percentages to optimize a precipitation reaction when using a different alcohol.

As used herein, the term "ultrafiltration (UF)" encompasses a variety of membrane filtration methods in which hydrostatic pressure forces a liquid against a semi-permeable membrane. Suspended solids and solutes of high molecular weight are retained, while water and low molecular weight solutes pass through the membrane. This separation process is often used for purifying and concentrating macromolecular ($10^3$-$10^6$ Da) solutions, especially protein solutions. A number of ultrafiltration membranes are available depending on the size of the molecules they retain. Ultrafiltration is typically characterized by a membrane pore size between 1 and 1000 kDa and operating pressures between 0.01 and 10 bar.

As used herein, the term "diafiltration" is performed with the same or a similar membrane as ultrafiltration and is typically performed in a tangential flow filtration mode. During diafiltration, buffer is introduced into the recycle tank while filtrate is removed from the unit operation. In processes where the product is in the retentate (for example, IgG), diafiltration is particularly useful for separating protein from small molecules like sugars and salts. In certain cases, diafiltration can be used to exchange the solution, buffer, or individual components of a buffering system.

As used herein, the term "about" denotes an approximate range of plus or minus 10% from a specified value. For instance, the language "about 20%" encompasses a range of 18-22%.

As used herein, the term "therapeutically effective amount or dose" or "sufficient/effective amount or dose," refers to a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins; the disclosures of which are hereby expressly incorporated herein by reference in their entireties for all purposes).

As used herein, the terms "intranasal administration" and "nasal administration" refer to administration of a therapeutic composition to the nasal cavity of a subject such that a therapeutic agent in the composition is delivered directly to one or more epithelium located in the nose. In certain embodiments, intranasal administration is achieved using a liquid preparation (e.g., an aqueous preparation), an aerosolized preparation, or a dry powder preparation, each of which can be administered via an externally propelled or self-propelled (e.g., via inhalation) non-invasive nasal delivery device, or via a gel, cream, ointment, lotion, or paste directly applied to one or more nasal epithelium (e.g., olfactory epithelium or nasal respiratory epithelium).

As used here, the terms "dose" and "dosage" are used interchangeably and refer to the amount of active ingredient given to an individual at each administration. The dose will vary depending on a number of factors, including frequency of administration; size and tolerance of the individual; severity of the condition; risk of side effects; and the route of administration. One of skill in the art will recognize that the dose can be modified depending on the above factors or based on therapeutic progress. The term "dosage form" refers to the particular format of the pharmaceutical, and depends on the route of administration.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

III. Enrichment of Anti-Brain Disease-Related Protein Antibodies from Plasma In some embodiments, methods are provided for preparing an immunoglobulin preparation enriched in brain disease-related immunoglobulins from plasma (e.g., pooled human plasma). The method includes providing a plasma-derived immunoglobulin composition (e.g., a suspended precipitate formed during the fractionation of plasma) containing IgG immunoglobulins including an anti-brain disease-related protein antibodies (e.g., anti-amyloid beta (anti-Aβ) immunoglobulins, anti-RAGE immunoglobulins, anti-α-synuclein immunoglobulins, or other immunoglobulins specific for a brain disease-related protein). The method also includes binding the IgG immunoglobulins to a cation exchange material (e.g., under conductivity and pH conditions in which the majority of the IgG immunoglobulins bind). The method, optionally, also includes a step of washing the bound cation exchange material to remove loosely bound contaminants. The method then includes eluting a majority of the bound IgG immunoglobulins from the cation exchange material (e.g., under conditions in which a smaller population of IgG immunoglobulins, enriched in anti-brain disease-related immunoglobulins, remains bound to the cation exchange material). The method then includes eluting IgG immunoglobulins not eluted in the first elution step off of the cation exchange column (e.g., by further increasing the conductivity or pH of the solution conditions, for example, in an elution buffer), the IgG immunoglobulins not eluted in the first elution step enriched in anti-brain disease-related protein immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein).

In some embodiments, these methods are achieved by eluting the bulk of the IgG immunoglobulins off of the cation exchange material (e.g., a weak cation exchange resin, such as a carboxymethyl (CM) resin), in a first elution step, under solution conditions (e.g., with an elution buffer) having a pH of from about 4.0 to about 10.0 and a conductivity of from about 3.0 mS/cm to about 16.0 mS/cm.

In some embodiments, IgG remaining bound to the cation exchange material (e.g., the weak cation exchange resin, such as a carboxymethyl resin) after the first elution step is eluted from the cation exchange material, in a second elution step, by increasing the conductivity and/or pH of the solution conditions used in the first elution step (e.g., with a second elution buffer that further destabilizes interactions between IgG immunoglobulins and cation exchange material. For example, where the first elution was performed using an elution buffer having a conductivity of about 5.0 mS/cm, pH 8.5, the second elution is performed with a second elution buffer having a conductivity above 5.0 mS/cm and/or a pH above 8.5.

In some embodiments, the second eluate, enriched in anti-brain disease-related protein immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein) recovered from the cation exchange material is further enriched or purified to produce a final composition. In some embodiments, the final composition is enriched in anti-brain disease-related protein immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein), as compared to the relative concentration of the anti-brain disease-related protein immunoglobulins, for example, in the starting material (e.g., a plasma sample or plasma pool) or in the first eluate fraction of the cation exchange elution step, or alternatively, to the relative concentration of, for example, an average commercial plasma-derived IgG preparation or an average human plasma sample (e.g., the concentration of anti-brain disease-related IgG in the final composition is higher than the average concentration in the human population, the average concentration in plasma samples from at least 1,000 random individuals, or the average concentration in samples of at least 1,000 lots of a commercial preparation of plasma-derived IgG).

In some embodiments, the composition enriched in anti-brain disease-related IgG immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein) is further enriched by one or more downstream enrichment steps, including without limitation, a further precipitation step (e.g., alcohol fractionation or polyethylene glycol fractionation), a chromatographic step (e.g., ion exchange chromatography such as anion exchange and/or cation exchange chromatography, affinity chromatography such as heparin affinity chromatography, immunoaffinity chromatography, size exclusion chromatography, or a combination thereof), a filtration step (e.g., ultrafiltration and/or diafiltration, nanofiltration, depth filtration, or sterile filtration), ultracentrifugation, electrophoretic preparation, and the like.

In some embodiments, the method further includes subjecting the composition enriched in anti-brain disease-related IgG immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein) to one or more dedicated virus removal and/or inactivation steps (e.g., solvent and detergent (S/D) treatment, nanofiltration, heat treatment, or incubation at low pH). In some embodiments, the IgG composition is further processes (e.g., enriched, buffer exchanged, or filtered) prior to and/or between performance of one or more dedicated virus removal and/or inactivation steps.

In some embodiments, the method includes a step of further purifying the composition enriched in anti-brain disease-related IgG immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein) recovered from the second cation exchange elution step by cation exchange chromatography.

In some embodiments, the method includes a step of further purifying the composition enriched in anti-brain disease-related IgG immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein) recovered from the second cation exchange elution step by flow-through anion exchange chromatography.

In a specific embodiment, the method includes steps of further purifying the composition enriched in anti-brain disease-related IgG immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein) by cation exchange chromatography and by flow through anion exchange chromatography.

In another specific embodiment, the method steps of further purifying the composition enriched in anti-brain disease-related IgG immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein) by cation exchange chromatography, by flow through anion exchange chromatography, by nanofiltration, and by incubation at low pH (e.g., for at least one week).

Further details regarding the separation, enrichment, purification, and viral removal and/or activation steps described above are provided below. It is contemplated that all combinations of specific conditions (e.g., pH, temperature, precipitant concentration, and/or ionic strength) for performing each of these individual steps can be used to perform the methods described herein for preparing an immunoglobulin composition (e.g., a plasma-derived IgG composition) enriched in anti-brain disease-related protein immunoglobulin (e.g., anti-amyloid beta (anti-Aβ) IgG immunoglobulins, anti-RAGE IgG immunoglobulins, anti-α-synuclein IgG immunoglobulins, or other IgG immunoglobulins specific for a brain disease-related protein) from plasma (e.g., human pooled plasma). For brevity, each of these specific conditions are not repeated here.

A. Preparation of Cryo-Poor Plasma

The starting material used for the preparation of commercial plasma-derived blood products, such as pooled IgG (e.g., IVIG or IgG for subcutaneous administration) generally consists of pooled lots of recovered plasma (i.e., plasma that has been separated from whole blood ex vivo) and/or or source plasma (i.e., plasma collected via plasmapheresis). The purification process typically starts by thawing previously frozen pooled plasma, which has already been assayed for safety and quality considerations, at a temperature no higher than 6° C. After complete thawing of the frozen plasma at low temperature, centrifugation is performed in the cold (e.g., ≤6° C.) to separate solid cryo-precipitates from the liquid supernatant. Alternatively, this separation step can be performed by filtration, rather than centrifugation. The liquid supernatant (also referred to as "cryo-poor plasma") is then, optionally, pre-processed by removing various factors, for example factor eight inhibitor bypass activity (FEIBA), Factor IX-complex, Factor VII, anti-thrombin III, Prothrombin complexes, by solid phase adsorption, chromatography, etc. The final product of these steps, which is used as the starting material for the fractionation process resulting in the isolation of IgG, alpha-1-antitrypsin (A1PI), and/or albumin, is commonly referred to a the "Cohn pool."

B. Fraction I Precipitation

To form a Fraction I precipitate (e.g., a Cohn or Kistler-Nitschmann Fraction I), the Cohn pool (e.g., cryo-poor plasma solution) is cooled to below about 6° C. (typically to about 0±1° C.) and the pH of the solution is adjusted to between about 7.0 and about 7.5. In some embodiments, the pH of the Cohn pool is adjusted to between about 7.1 and about 7.3. In a specific embodiment, the pH of the cryo-poor plasma is adjusted to a pH of at or about 7.2. Pre-cooled alcohol (typically ethanol, e.g., denatured ethanol) is then added to a target concentration of from about 6% to about 10% (v/v), typically while stirring the solution. In some embodiments, ethanol (e.g., denatured ethanol) is added to a target concentration of from about 7% to about 9% (v/v). In a specific embodiment, ethanol (e.g., denatured ethanol) is added to a target concentration of at or about 8% (v/v). At the same time the temperature is further lowered to below 0° C., typically between about −4° C. and about 0° C. In a specific embodiment, the temperature is lowered to at or about −2° C. Typically, the precipitation reaction includes a hold time of at least about 1 hour, although shorter or longer hold times may also be employed. After completion of the precipitation reaction, the supernatant (e.g., "Supernatant I") is then separated from the precipitate (e.g., "Fraction I" precipitate) by centrifugation, filtration, or other suitable means.

C. Fraction II+III Precipitation

To form a Fraction II+III precipitate (e.g., a Cohn Fraction II+III precipitate or Kistler-Nitschmann Precipitate A), a Cohn pool or a derivative thereof (e.g., a Fraction I supernatant) is cooled to below about 0° C. and the pH of the solution is adjusted to between about 5.5 and about 7.0. In some embodiments, the pH of the Cohn pool or derivative thereof is adjusted to between about 6.5 and about 7.0. In some embodiments, the pH of the Cohn pool or derivative thereof is adjusted to between about 5.5 and about 6.0. Pre-cooled alcohol (typically ethanol, e.g., denatured ethanol) is then added to a target concentration of from about 17% to about 27% (v/v), typically while stirring the solution. In some embodiments, ethanol (e.g., denatured ethanol) is added to a target concentration of from about 20% to about 25% (v/v). At the same time the temperature is further lowered, typically between about −9° C. and about −5° C. In a specific embodiment, the temperature is lowered to at or about −7° C., to precipitate components of the cryo-poor plasma or derivative thereof, including IgG. Typically, the precipitation reaction includes an incubation time of at least about 1 hour, although shorter or longer incubation times may also be employed. After completion of the precipitation reaction, the supernatant (e.g., "Supernatant II+III") is then separated from the precipitate (e.g., "Fraction II+III" precipitate) by centrifugation, filtration, or other suitable means.

D. IgG Extraction and Silicon Dioxide Treatment of Fraction II+III Precipitate

In order to solubilize the IgG content of a Fraction II+III precipitate, a cold extraction buffer is used to suspend the Fractionation II+III precipitate at a typical ratio of 1 part precipitate to 15 parts of extraction buffer. Other suitable re-suspension ratios may be used, for example from about 1:8 to about 1:30, or from about 1:10 to about 1:20, or from about 1:12 to about 1:18, or from about 1:13 to about 1:17, or from about 1:14 to about 1:16. In certain embodiments, the re-suspension ratio may be about 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, or higher.

Suitable solutions for the extraction of the Fraction II+III precipitate will generally have a pH between about 4.0 and about 5.5. In certain embodiments, the solution will have a pH between about 4.5 and about 5.0, in other embodiments, the extraction solution will have a pH of about 4.0, 4.1, 4.2, 4.3, 4.4, 4.5, 4.6, 4.7, 4.8, 4.9, 5.0, 5.1, 5.2, 5.3, 5.4, or 5.5. In a preferred embodiment, the pH of the extraction buffer will be at or about 4.5. In another preferred embodiment, the pH of the extraction buffer will be at or about 4.7. In another preferred embodiment, the pH of the extraction buffer will be at or about 4.9. Generally, these pH requirements can be met using a buffering agent selected from, for example, acetate, citrate, monobasic phosphate, dibasic phosphate, mixtures thereof, and the like. Suitable buffer concentrations typically range from about 5 to about 100 mM, or from about 10 to about 50 mM, or about 5, 10, 15, 20, 25, 30, 35, 40, 45, 50, 55, 60, 65, 70, 75, 80, 85, 90, 95, or 100 mM buffering agent.

The extraction buffer will preferably have a conductivity of from about 0.5 mS·cm$^{-1}$ to about 2.0 mS·cm$^{-1}$. For example, in certain embodiments, the conductivity of the extraction buffer will be about 0.5 mS·cm$^{-1}$, or about 0.6, 0.7, 0.8, 0.9, 1.0, 1.1, 1.2, 1.3, 1.4, 1.5, 1.6, 1.7, 1.8, 1.9, or about 2.0 mS·cm$^{-1}$. One of ordinary skill in the art will know how to generate extraction buffers having an appropriate conductivity.

In some embodiments, the extraction is performed at between about 0° C. and about 10° C., or between about 2° C. and about 8° C. In certain embodiments, the extraction may be performed at about 0° C., 1° C., 2° C., 3° C., 4° C., 5° C., 6° C., 7° C., 8° C., 9° C., or 10° C. In a particular embodiment, the extraction is performed at between about 2° C. and about 10° C. Typically, the extraction process will proceed for between about 60 and about 300 minutes, or for between about 120 and 240 min, or for between about 150 and 210 minutes, while the suspension is continuously stirred. In certain embodiments, the extraction process will proceed for about 60, 70, 80, 90, 100, 110, 120, 130, 140, 150, 160, 170, 180, 190, 200, 210, 220, 230, 240, 250, 260, 270, 280, 290, or about 300 minutes. In a preferred embodiment, the extraction process will proceed for at least 160 minutes with continuous stirring.

In some embodiments, the extraction buffer contains 5 mM monobasic sodium phosphate, 5 mM acetate, and 0.051% to 0.06% glacial acetic acid (v/v). In some embodiments, the Fraction II+III precipitate is extracted with a paste to buffer ration of at or about 1:15 at a pH of at or about 4.5±0.2. In some embodiments, the Fraction II+III precipitate in a dissolution buffer containing 600 mL glacial acetic acid per 1000 L. In one particular embodiment, an exemplary extraction buffer may contain at or about 5 mM monobasic sodium phosphate and at or about 5 mM acetate at a pH of at or about 4.5±0.2 and conductivity of at or about 0.7 to 0.9 mS/cm.

The extracted Fraction II+III precipitate is then treated by addition of finely divided silica dioxide particles (e.g., fumed silica, Aerosil®) followed by a 40 to 80 minute incubation period during which the suspension is constantly mixed. In certain embodiments, the incubation period will be between about 50 minutes and about 70 minutes, or about 30, 35, 40, 45, 50, 55, 60, 65, 70, 75, 80, or more minutes. Generally, the treatment will be performed at between about 0° C. and about 10° C., or between about 2° C. and about 8° C. In certain embodiments, the treatment may be performed at about 0° C., 1° C., 2° C., 3° C., 4° C., 5° C., 6° C., 7° C., 8° C., 9° C., or 10° C. In a particular embodiment, the treatment is performed at between about 2° C. and about 10° C.

In some embodiments, fumed silica is added at a concentration of between about 20 g/kg II+III paste and about 100 g/kg II+III paste (i.e., for a Fraction II+III precipitate that is extracted at a ratio of 1:15, fumed silica should be added at a concentration from about 20 g/16 kg II+III suspension to about 100 g/16 kg II+III suspension, or at a final concentration of about 0.125% (w/w) to about 0.625% (w/w)). In certain embodiments, the fumed silica may be added at a concentration of about 20 g/kg II+III paste, or about 25, 30, 35, 40, 45, 50, 55, 60, 65, 70, 75, 80, 85, 90, 95, or 100 g/kg II+III paste. In one specific embodiment, fumed silica (e.g., Aerosil 380 or equivalent) is added to the Modified Fraction II+III suspension to a final concentration of about 40 g/16 kg II+III. Mixing takes place at about 2 to 8° C. for at least 50 to 70 minutes.

In some embodiments, the fumed silica treatment includes addition of from about 0.01 kg/kg II+III paste to about 0.07 kg/kg II+III paste, or from about 0.02 kg/kg II+III paste to about 0.06 kg/kg II+III paste, or from about 0.03 kg/kg II+III paste to about 0.05 kg/kg II+III paste, or about 0.02, 0.03, 0.04, 0.05, 0.06, or 0.07 kg/kg II+III paste, and the mixture will be incubated for between about 50 minutes and about 70 minutes, or about 30, 35, 40, 45, 50, 55, 60, 65, 70, 75, 80, or more minutes at a temperature between about 2° C. and about 8° C.

In order to separate the insoluble fraction of the Fraction II+III precipitate (i.e., the Fraction II+III silicon dioxide filter cake), the suspension is filtered, typically using depth filtration. Depth filters that may be employed in the methods provided herein include, metallic, glass, ceramic, organic (such as diatomaceous earth) depth filters, and the like. Example of suitable filters include, without limitation, Cuno 50SA, Cuno 90SA, and Cuno VR06 filters (Cuno). Alternatively, the separation step can be performed by centrifugation rather than filtration.

In certain embodiments, filter aid, for example Celpure C300 (Celpure) or Hyflo-Supper-Cel (World Minerals), will be added after the silica dioxide treatment, to facilitate depth filtration. Filter aid can be added at a final concentration of from about 0.01 kg/kg II+III paste to about 0.07 kg/kg II+III paste, or from about 0.02 kg/kg II+III paste to about 0.06 kg/kg II+III paste, or from about 0.03 kg/kg II+III paste to about 0.05 kg/kg II+III paste. In certain embodiments, the filter aid will be added at a final concentration of about 0.01 kg/kg II+III paste, or about 0.02, 0.03, 0.04, 0.05, 0.06, or 0.07 kg/kg II+III paste.

In some embodiments, where the soluble fraction is separated from the insoluble fraction by filtration, the filter is washed with between about 3 and about 5 volumes of the filter dead volume after completing the filtration. In certain embodiments, the filter will be washed with between about 3.5 volumes and about 4.5 volumes, or at least about 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 volumes of the filter dead volume. In a particular embodiment, the filter press will be washed with at least about 3.6 dead volumes of suspension buffer.

E. First Cation Exchange Chromatography

In some embodiments, an IgG immunoglobulin composition enriched in anti-brain disease-related protein IgG immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein) is prepared by binding IgG immunoglobulins isolated from plasma (e.g., pooled human plasma or a fraction thereof, such as a cryo-poor plasma pool, Fraction I supernatant, Fraction II+III precipitate, or Precipitate G precipitate) to a cation exchange resin and differentially eluting the anti-brain disease-related protein immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein) and bulk plasma-derived IgG. This creates two IgG compositions, one which is not enriched for anti-brain disease-related protein IgG immunoglobulins and one that is enriched in anti-brain disease-related protein IgG immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein). In one embodiment, the differential elution is accomplished by first eluting the bulk of the bound IgG immunoglobulins from the cation exchange material, and subsequently eluting IgG remaining bound to the cation exchange material in a second elution step. In some embodiments, both IgG compositions can be further purified and/or processed to create IgG compositions with different relative concentrations of individual IgG immunoglobulins.

Optimal pH and conductivity used during the binding of plasma-derived immunoglobulins to a cation exchange material are dependent upon factors, including without limitation, the characteristics of the cation exchange material being used. One of skill will be able to determine appropriate binding conditions that allow for the majority (e.g., at least 75%, preferably at least 90%, more preferably at least 95%) of the IgG content to bind to the cation exchange material. The exact conditions under which the IgGs bind is not critical, assuming that an acceptable content of IgG are bound.

Of higher importance are the conditions under which the IgGs are eluted. In some embodiments, the methods provided herein are based on the discovery that IgG compositions enriched in anti-brain disease-related protein immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein) can be differentially eluted from cation exchange material based on their increased affinity. Because anti-brain disease-related protein IgGs (e.g., anti-amyloid beta (anti-Aβ) immunoglobulins, anti-RAGE immunoglobulins, anti-α-synuclein immunoglobulins, or other immunoglobulins specific for a brain disease-related protein) have a greater affinity for the cation exchange material (e.g., weak cation exchange material such as carboxymethyl resin), a first elution can be performed under moderate solutions conditions (e.g., ionic strength and pH) suitable for eluting the bulk of the IgG from the cation exchange and a second elution can be performed under more rigorous solution conditions (e.g., higher ionic strength and/or pH) to elute an IgG content, remaining bound to the cation exchange material after the first elution, enriched in the anti-brain disease-related protein IgGs (e.g., anti-amyloid beta (anti-Aβ) immunoglobulins, anti-RAGE immunoglobulins, anti-α-synuclein immunoglobulins, or other immunoglobulins specific for a brain disease-related protein)

In some embodiments, the first cation exchange elution step is performed using an elution buffer having a pH of 4.0 to 10.0 and a conductivity of 3.0 mS/cm to 16.0 mS/cm. In some embodiments, the pH of the first cation exchange elution step is about 4.0 to about 9.0, or from about 5.0 to about 10.0, or from about 5.0 to about 9.0, or from about 5.0 to about 8.0, or from about 6.0 to about 10.0, or from about 6.0 to about 9.0, or from about 6.0 to about 8.0, or from about 7.0 to about 10.0, or from about 7.0 to about 9.0, or from about 7.0 to about 8.0, or from about 8.0 to about 10.0, or from about 8.0 to about 9.0, or from about 9.0 to about 10.0. In some embodiments, the first cation exchange elution is performed using an elution buffer having a pH of about 4.5±0.5, 4.6±0.5, 4.7 4.8±0.5, 4.9±0.5, 5.0±0.5, 5.1±0.5, 5.2±0.5, 5.3±0.5, 5.4±0.5, 5.5±0.5, 5.6±0.5, 5.7±0.5, 5.8±0.5, 5.9±0.5, 6.0±0.5, 6.1±0.5, 6.2±0.5, 6.3±0.5, 6.4±0.5, 6.5±0.5, 6.6±0.5, 6.7±0.5, 6.8±0.5, 6.9±0.5, 7.0±0.5, 7.1±0.5, 7.2±0.5, 7.3±0.5, 7.4±0.5, 7.5±0.5, 7.6±0.5, 7.7±0.5, 7.8±0.5, 7.9±0.5, 8.0±0.5, 8.1±0.5, 8.2±0.5, 8.3±0.5, 8.4±0.5, 8.5±0.5, 8.6±0.5, 8.7±0.5, 8.8±0.5, 8.9±0.5, 9.0±0.5, 9.1±0.5, 9.2±0.5, 9.3±0.5, 9.4±0.5, or 9.5±0.5.

In some embodiments, the conductivity of the first cation exchange elution step is about 5±2, 6±2, 7±2, 8±2, 9±2, 10±2, 11±2, 12±2, 13±2, 14±2, 6±3, 7±3, 8±3, 9±3, 10±3, 11±3, 12±3, 13±3, 7±4, 8±4, 9±4, 10±4, 11±4, 12±4, 8±5, 9±5, 10±5, 11±5, 9±6, or 10±6.

In one embodiment, the second cation exchange elution step is performed using a second elution buffer having higher conductivity and/or a higher than the elution buffer used in the first cation elution step. In some embodiments, the second elution buffer has a pH of 4.0 to 10.0 and a conductivity of 10.0 mS/cm to 300 mS/cm. In some embodiments, the pH the second cation exchange elution step is about 4.0 to about 9.0, or from about 5.0 to about 10.0, or from about 5.0 to about 9.0, or from about 5.0 to about 8.0, or from about 6.0 to about 10.0, or from about 6.0 to about 9.0, or from about 6.0 to about 8.0, or from about 7.0 to about 10.0, or from about 7.0 to about 9.0, or from about 7.0 to about 8.0, or from about 8.0 to about 10.0, or from about 8.0 to about 9.0, or from about 9.0 to about 10.0. In some embodiments, the second cation exchange elution is performed using an elution buffer having a pH of about 4.5±0.5, 4.6±0.5, 4.7 4.8±0.5, 4.9±0.5, 5.0±0.5, 5.1±0.5, 5.2±0.5, 5.3±0.5, 5.4±0.5, 5.5±0.5, 5.6±0.5, 5.7±0.5, 5.8±0.5, 5.9±0.5, 6.0±0.5, 6.1±0.5, 6.2±0.5, 6.3±0.5, 6.4±0.5, 6.5±0.5, 6.6±0.5, 6.7±0.5, 6.8±0.5, 6.9±0.5, 7.0±0.5, 7.1±0.5, 7.2±0.5, 7.3±0.5, 7.4±0.5, 7.5±0.5, 7.6±0.5, 7.7±0.5, 7.8±0.5, 7.9±0.5, 8.0±0.5, 8.1±0.5, 8.2±0.5, 8.3±0.5, 8.4±0.5, 8.5±0.5, 8.6±0.5, 8.7±0.5, 8.8±0.5, 8.9±0.5, 9.0±0.5, 9.1±0.5, 9.2±0.5, 9.3±0.5, 9.4±0.5, or 9.5±0.5.

In some embodiments, the conductivity of the second cation exchange elution step is from about 50 mS/cm to about 250 mS/cm, from about 80 mS/cm to about 200 mS/cm, from about 80 mS/cm to about 150 mS/cm, from about 80 mS/cm to about 120 mS/cm, or about 100±80 mS/cm, 100±60 mS/cm, 100±40 mS/cm, 100±20 mS/cm, or 100±10 mS/cm.

F. Conductivity Reduction/pH Adjustment

In some embodiments, the eluate, recovered from the first cation exchange chromatography step, containing the IgG fraction enriched in anti-brain disease-related protein IgG immunoglobulins has a relatively high salt concentration, because these immunoglobulins bind more tightly to the cation exchange material than does the bulk fraction of IgG immunoglobulins. In some embodiments, where the next purification step includes binding the IgG fraction enriched in anti-brain disease-related proteins to a second ion exchange material (e.g., in a second cation exchange chromatographic step), the conductivity of the composition is reduced to promote binding. In some embodiments, the pH of the solution is also adjusted to improve binding of the immunoglobulins and/or the resolving power of the subsequent chromatographic step. Non-limiting examples of methods useful for reducing the conductivity and/or adjusting the pH of the solution include diafiltration, ultrafiltration and diafiltration (UF/DF), dialysis, dilution, dilution and concentration, and gel filtration/de-salting chromatography.

In one embodiment, the conductivity of the eluate, recovered from the first cation exchange chromatography step, containing the IgG fraction enriched in anti-brain disease-related protein IgG immunoglobulins is reduced by a combination of ultrafiltration, diafiltration, and dilution. Ultra/diafiltration methods, systems, and membranes useful for buffer exchange and concentration of immunoglobulins are well known in the art (see, e.g., U.S. Pat. No. 8,546,548 and U.S. Patent Application Publication No. 2011/0213126, the disclosures of which are hereby expressly incorporated herein by reference in their entireties for all purposes).

In some embodiments, ultra/diafiltration is performed using a cassette (e.g., with an open channel screen) and an ultra/diafiltration membrane having a nominal molecular weight cut off (NMWCO) of no more than about 150 kDa or no more than about 140, 130, 120, 100, 90, 80, 70, 60, 50, 40, or 30 kDa. In one embodiment, the ultrafiltration membrane has a NMWCO of about 30 kDa. In one embodiment, the ultra/diafiltration membrane is used with an A-screen geometry. In another embodiment, the ultra/diafiltration membrane is used with a V-screen geometry.

In some embodiments, the eluate, recovered from the first cation exchange chromatography step, containing the IgG fraction enriched in anti-brain disease-related protein IgG immunoglobulins is adjusted to a pH of from about 5.0 to about 7.0 and a conductivity of from about 1.0 mS/cm to about 15 mS/cm prior to binding the immunoglobulins to a second cation exchange resin. In one embodiment, the eluate is adjusted to a pH of from 5.0 to 6.0 and a conductivity of from 1.0 mS/cm to 15 mS/cm. In another embodiment, the eluate is adjusted to a pH of from 5.0 to 6.0 and a conductivity of from 3.0 mS/cm to 9.0 mS/cm. In another embodiment, the eluate is adjusted to a pH of from 5.0 to 6.0 and a conductivity of from 8.0 mS/cm to 14.0 mS/cm. In another embodiment, the eluate is adjusted to a pH of from 5.0 to 5.5 and a conductivity of from 3.0 mS/cm to 9.0 mS/cm. In another embodiment, the eluate is adjusted to a pH of from 5.0 to 5.5 and a conductivity of from 8.0 mS/cm to 14.0 mS/cm. In another embodiment, the eluate is adjusted to a pH of $5.2\pm0.1$ and a conductivity of $6.0\pm2$ mS/cm. In another embodiment, the eluate is adjusted to a pH of $5.2\pm0.1$ and a conductivity of $11.0\pm2$.

In some embodiments, the pH of the eluate is adjusted to $5.0\pm0.2$, $5.1\pm0.2$, $5.2\pm0.2$, $5.3\pm0.2$, $5.4\pm0.2$, $5.5\pm0.2$, $5.6\pm0.2$, $5.7\pm0.2$, $5.8\pm0.2$, $5.9\pm0.2$, $6.0\pm0.2$, $6.1\pm0.2$, $6.2\pm0.2$, $6.3\pm0.2$, $6.4\pm0.2$, $6.5\pm0.2$, $6.6\pm0.2$, $6.7\pm0.2$, $6.8\pm0.2$, $6.9\pm0.2$, $7.0\pm0.2$, $5.0\pm0.1$, $5.1\pm0.1$, $5.2\pm0.1$, $5.3\pm0.1$, $5.4\pm0.1$, $5.5\pm0.1$, $5.6\pm0.1$, $5.7\pm0.1$, $5.8\pm0.1$, $5.9\pm0.1$, $6.0\pm0.1$, $6.1\pm0.1$, $6.2\pm0.1$, $6.3\pm0.1$, $6.4\pm0.1$, $6.5\pm0.1$, $6.6\pm0.1$, $6.7\pm0.1$, $6.8\pm0.1$, $6.9\pm0.1$, or $7.0\pm0.1$.

In some embodiments, the conductivity of the eluate is adjusted to $3.0\pm2$ mS/cm, $4.0\pm2$ mS/cm, $5.0\pm2$ mS/cm, $6.0\pm2$ mS/cm, $7.0\pm2$ mS/cm, $8.0\pm2$ mS/cm, $9.0\pm2$ mS/cm, $10\pm2$ mS/cm, $11\pm2$ mS/cm, $12\pm2$ mS/cm, $13\pm2$ mS/cm, $14\pm2$ mS/cm, $2.0\pm1$ mS/cm, $3.0\pm1$ mS/cm, $4.0\pm1$ mS/cm, $5.0\pm1$ mS/cm, $6.0\pm1$ mS/cm, $7.0\pm1$ mS/cm, $8.0\pm1$ mS/cm, $9.0\pm1$ mS/cm, $10\pm1$ mS/cm, $11\pm1$ mS/cm, $12\pm1$ mS/cm, $13\pm1$ mS/cm, $14\pm1$ mS/cm, or $15\pm1$ mS/cm.

In some embodiments, the eluate, recovered from the first cation exchange chromatography step, containing the IgG fraction enriched in anti-brain disease-related protein IgG immunoglobulins is concentrated to a protein concentration of from about 2 g/L (0.2%) to about 100 g/L (10%) prior to binding the immunoglobulins to a second cation exchange resin. In one embodiment, the eluate is concentrated to a protein concentration of from about 5 g/L (0.5%) to about 50 g/L (5%). In one embodiment, the eluate is concentrated to a protein concentration of from about 2 g/L (0.2%) to about 50 g/L (5%). In one embodiment, the eluate is concentrated to a protein concentration of from 10 g/L (1%) to 50 g/L (5%). In one embodiment, the eluate is concentrated to a protein concentration of from 10 g/L (1%) to 30 g/L (3%). In some embodiments, the eluate is concentrated to a protein concentration of 2 g/L (0.2%), 3 g/L (0.3%), 4 g/L (0.4%), 5 g/L (0.5%), 6 g/L (0.6%), 7 g/L (0.7%), 8 g/L (0.8%), 9 g/L (0.9%), 10 g/L (1%), 12.5 g/L (1.25%), 15 g/L (1.5%), 17.5 g/L (1.75%), 20 g/L (2%), 25 g/L (2.5%), 30 g/L (3%), 35 g/L (3.5%), 40 g/L (4%), 45 g/L (4.5%), 50 g/L (5%), 55 g/L (5.5%), 60 g/L (6%), 65 g/L (6.5%), 70 g/L (7%), 75 g/L (7.5%), 80 g/L (8%), 85 g/L (8.5%), 90 g/L (9%), 95 g/L (9.5%), or 100 g/L (10%).

In one embodiment, the eluate is adjusted to a pH of from 5.0 to 5.5, a conductivity of from 3.0 mS/cm to 9.0 mS/cm, and a protein concentration of from 5 g/L (0.5%) to 50 g/L (5%) prior to binding the immunoglobulins to a second cation exchange resin. In one embodiment, the eluate is adjusted to a pH of from 5.0 to 5.5, a conductivity of from 8.0 mS/cm to 14.0 mS/cm, and a protein concentration of from 5 g/L (0.5%) to 50 g/L (5%) prior to binding the immunoglobulins to a second cation exchange resin.

G. Second Cation Exchange Chromatography

In some embodiments, an IgG composition enriched in anti-brain disease-related protein IgG immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein), for example as isolated using a cation exchange chromatographic step described above, is further purified by cation exchange chromatography. In some embodiments, the method includes binding the anti-brain disease-related protein IgG composition to a cation exchange material (e.g., a weak cation exchange material such as a carboxymethyl resin, for example, CM Sepharose or CM HyperD resin), optionally washing loosely bound impurities bound to the cation exchange material in a wash step, and eluting the IgG immunoglobulins from the cation exchange material. In one embodiment, the weak cation exchange material is a carboxymethyl resin. In one embodiment, the carboxymethyl resin is CM HyperD resin.

In some embodiments, the binding step is performed under solution conditions having a pH of 4.0 to 10.0 and a conductivity of 1 to 15 mS/cm. In some embodiments, the binding step is performed under solution conditions having a pH of about 4.0 to about 9.0, or from about 5.0 to about 10.0, or from about 5.0 to about 9.0, or from about 5.0 to about 8.0, or from about 6.0 to about 10.0, or from about 6.0 to about 9.0, or from about 6.0 to about 8.0, or from about 7.0 to about 10.0, or from about 7.0 to about 9.0, or from about 7.0 to about 8.0, or from about 8.0 to about 10.0, or from about 8.0 to about 9.0, or from about 9.0 to about 10.0. In some embodiments, the first cation exchange elution is performed using an elution buffer having a pH of about $4.5\pm0.5$, $4.6\pm0.5$, 4.7 $4.8\pm0.5$, $4.9\pm0.5$, $5.0\pm0.5$, $5.1\pm0.5$, $5.2\pm0.5$, $5.3\pm0.5$, $5.4\pm0.5$, $5.5\pm0.5$, $5.6\pm0.5$, $5.7\pm0.5$, $5.8\pm0.5$, $5.9\pm0.5$, $6.0\pm0.5$, $6.1\pm0.5$, $6.2\pm0.5$, $6.3\pm0.5$, 6.4±0.5, 6.5±0.5, 6.6±0.5, 6.7±0.5, 6.8±0.5, 6.9±0.5, 7.0±0.5, 7.1±0.5, 7.2±0.5, 7.3±0.5, 7.4±0.5, 7.5±0.5, 7.6±0.5, 7.7±0.5, 7.8±0.5, 7.9±0.5, 8.0±0.5, 8.1±0.5, 8.2±0.5, 8.3±0.5, 8.4±0.5, 8.5±0.5, 8.6±0.5, 8.7±0.5, 8.8±0.5, 8.9±0.5, 9.0±0.5, 9.1±0.5, 9.2±0.5, 9.3±0.5, 9.4±0.5, or 9.5±0.5.

In some embodiments, the binding step is performed under solution conditions having a conductivity of about 3±2, 4±2, 5±2, 6±2, 7±2, 8±2, 9±2, 10±2, 11±2, 12±2, 13±2, 14±2, 4±3, 5±3, 6±3, 7±3, 8±3, 9±3, 10±3, 11±3, 12±3, 13±3, 5±4, 6±4, 7±4, 8±4, 9±4, 10±4, 11±4, 12±4, 6±5, 7±5, 8±5, 9±5, 10±5, 11±5, 7±6, 8±6, 9±6, 10±6, 8±7, or 9±7.

In one embodiment, the binding step is performed under solution conditions having a pH of from about 5.0 to about 7.0 and a conductivity of from about 1.0 mS/cm to about 15 mS/cm. In one embodiment, the binding step is performed under solution conditions having a pH of from 5.0 to 6.0 and a conductivity of from 1.0 mS/cm to 15 mS/cm. In another embodiment, the binding step is performed under solution conditions having a pH of from 5.0 to 6.0 and a conductivity of from 3.0 mS/cm to 9.0 mS/cm. In another embodiment, the binding step is performed under solution conditions having a pH of from 5.0 to 6.0 and a conductivity of from 8.0 mS/cm to 14.0 mS/cm. In another embodiment, the binding step is performed under solution conditions having a pH of from 5.0 to 5.5 and a conductivity of from 3.0 mS/cm to 9.0 mS/cm. In another embodiment, the binding step is performed under solution conditions having a pH of from 5.0 to 5.5 and a conductivity of from 8.0 mS/cm to 14.0 mS/cm. In another embodiment, the binding step is performed under solution conditions having a pH of 5.2±0.1 and a conductivity of 6.0±2 mS/cm. In another embodiment, the binding step is performed under solution conditions having a pH of 5.2±0.1 and a conductivity of 11.0±2.

In some embodiments, the elution step is performed under solution conditions having a pH of 4.0 to 10.0 and a conductivity of 15.0 mS/cm to 300 mS/cm. In some embodiments, the elution buffer has a pH of 4.0 to 10.0 and a conductivity of 10.0 mS/cm to 300 mS/cm. In some embodiments, the pH of the elution step is about 4.0 to about 9.0, or from about 5.0 to about 10.0, or from about 5.0 to about 9.0, or from about 5.0 to about 8.0, or from about 6.0 to about 10.0, or from about 6.0 to about 9.0, or from about 6.0 to about 8.0, or from about 7.0 to about 10.0, or from about 7.0 to about 9.0, or from about 7.0 to about 8.0, or from about 8.0 to about 10.0, or from about 8.0 to about 9.0, or from about 9.0 to about 10.0. In some embodiments, the pH of the elution step is about 4.5±0.5, 4.6±0.5, 4.7 4.8±0.5, 4.9±0.5, 5.0±0.5, 5.1±0.5, 5.2±0.5, 5.3±0.5, 5.4±0.5, 5.5±0.5, 5.6±0.5, 5.7±0.5, 5.8±0.5, 5.9±0.5, 6.0±0.5, 6.1±0.5, 6.2±0.5, 6.3±0.5, 6.4±0.5, 6.5±0.5, 6.6±0.5, 6.7±0.5, 6.8±0.5, 6.9±0.5, 7.0±0.5, 7.1±0.5, 7.2±0.5, 7.3±0.5, 7.4±0.5, 7.5±0.5, 7.6±0.5, 7.7±0.5, 7.8±0.5, 7.9±0.5, 8.0±0.5, 8.1±0.5, 8.2±0.5, 8.3±0.5, 8.4±0.5, 8.5±0.5, 8.6±0.5, 8.7±0.5, 8.8±0.5, 8.9±0.5, 9.0±0.5, 9.1±0.5, 9.2±0.5, 9.3±0.5, 9.4±0.5, or 9.5±0.5.

In some embodiments, the conductivity of the elution step is from about 50 mS/cm to about 250 mS/cm, from about 80 mS/cm to about 200 mS/cm, from about 80 mS/cm to about 150 mS/cm, from about 80 mS/cm to about 120 mS/cm, or about 100±80 mS/cm, 100±60 mS/cm, 100±40 mS/cm, 100±20 mS/cm, or 100±10 mS/cm. Generally, the conductivity used to elute the immunoglobulins from the second cation exchange resin will depend upon the pH used, and vice versa. For example, where the pH of the elution condition is lower (e.g., below 7.0), higher conductivity will be needed to elute the immunoglobulins. In contrast, where the pH of the elution condition is higher (e.g., above 7.0), lower conductivity will be sufficient to elute the immunoglobulins. The skilled artisan will appreciate how to adjust the pH and conductivity of the elution conditions appropriately.

In one embodiment, the elution step is performed under solution conditions having a pH of from 7.0 to 10 and a conductivity of greater than 10 mS/cm. In one embodiment, the elution step is performed under solution conditions having a pH of from 7.0 to 10 and a conductivity of from 10 mS/cm to 100 mS/cm. In one embodiment, the elution step is performed under solution conditions having a pH of from 7.0 to 10 and a conductivity of from 10 mS/cm to 50 mS/cm. In one embodiment, the elution step is performed under solution conditions having a pH of from 7.0 to 10 and a conductivity of from 10 mS/cm to 25 mS/cm. In one embodiment, the elution step is performed under solution conditions having a pH of from 7.0 to 10 and a conductivity of from 10 mS/cm to 15 mS/cm.

In one embodiment, the elution step is performed under solution conditions having a pH of from 8.0 to 9.0 and a conductivity of greater than 10 mS/cm. In one embodiment, the elution step is performed under solution conditions having a pH of from 8.0 to 9.0 and a conductivity of from 10 mS/cm to 100 mS/cm. In one embodiment, the elution step is performed under solution conditions having a pH of from 8.0 to 9.0 and a conductivity of from 10 mS/cm to 50 mS/cm. In one embodiment, the elution step is performed under solution conditions having a pH of from 8.0 to 9.0 and a conductivity of from 10 mS/cm to 25 mS/cm. In one embodiment, the elution step is performed under solution conditions having a pH of from 8.0 to 9.0 and a conductivity of from 10 mS/cm to 15 mS/cm.

In one embodiment, the elution step is performed under solution conditions having a pH of 8.5±0.2 and a conductivity of greater than 10 mS/cm. In one embodiment, the elution step is performed under solution conditions having a pH of 8.5±0.2 and a conductivity of from 10 mS/cm to 100 mS/cm. In one embodiment, the elution step is performed under solution conditions having a pH of 8.5±0.2 and a conductivity of from 10 mS/cm to 50 mS/cm. In one embodiment, the elution step is performed under solution conditions having a pH of 8.5±0.2 and a conductivity of from 10 mS/cm to 25 mS/cm. In one embodiment, the elution step is performed under solution conditions having a pH of 8.5±0.2 and a conductivity of from 10 mS/cm to 15 mS/cm. In one embodiment, the elution step is performed under solution conditions having a pH of 8.5±0.2 and a conductivity of from 13±2 mS/cm.

H. Conductivity Reduction/pH Adjustment

In some embodiments, the eluate, recovered from the second cation exchange chromatography step, containing the IgG fraction enriched in anti-brain disease-related protein IgG immunoglobulins has a relatively high conductivity. In some embodiments, where the next purification step includes binding impurities from the IgG fraction enriched in anti-brain disease-related proteins to an anion exchange material, the conductivity of the composition is reduced to promote binding. In some embodiments, the pH of the solution is also adjusted to improve binding of the impurities, while the immunoglobulins flow-through the resin. Non-limiting examples of methods useful for reducing the conductivity and/or adjusting the pH of the solution include diafiltration, ultrafiltration and diafiltration (UF/DF), dialysis, dilution, dilution and concentration, and gel filtration/de-salting chromatography. In one embodiment, the conductivity of the eluate is reduced by dilution.

In some embodiments, ultra/diafiltration is performed using a cassette (e.g., with an open channel screen) and an ultra/diafiltration membrane having a nominal molecular weight cut off (NMWCO) of no more than about 150 kDa or no more than about 140, 130, 120, 100, 90, 80, 70, 60, 50, 40, or 30 kDa. In one embodiment, the ultrafiltration membrane has a NMWCO of about 30 kDa. In one embodiment, the ultra/diafiltration membrane is used with an A-screen geometry. In another embodiment, the ultra/diafiltration membrane is used with a V-screen geometry.

In one embodiment, the eluate recovered from the second cation exchange chromatography step is adjusted to a pH of from about 5.5 to about 7.5 and a conductivity of from about 0.5 mS/cm to about 15 mS/cm prior to binding the immunoglobulins to an anion exchange material. In one embodiment, the eluate is adjusted to a pH of from 5.9 to 6.9 and a conductivity of from 1.0 mS/cm to 15 mS/cm. In another embodiment, the eluate is adjusted to a pH of from 5.9 to 6.9 and a conductivity of from 1.0 mS/cm to 5.0 mS/cm. In another embodiment, the eluate is adjusted to a pH of $6.4\pm0.2$ and a conductivity of from 1.0 mS/cm to 5.0 mS/cm. In another embodiment, the eluate is adjusted to a pH of $6.4\pm0.2$ and a conductivity of $2.2\pm1$ mS/cm.

In some embodiments, the pH of the eluate is adjusted to $5.5\pm0.2$, $5.6\pm0.2$, $5.7\pm0.2$, $5.8\pm0.2$, $5.9\pm0.2$, $6.0\pm0.2$, $6.1\pm0.2$, $6.2\pm0.2$, $6.3\pm0.2$, $6.4\pm0.2$, $6.5\pm0.2$, $6.6\pm0.2$, $6.7\pm0.2$, $6.8\pm0.2$, $6.9\pm0.2$, $7.0\pm0.2$, $7.1\pm0.2$, $7.2\pm0.2$, $7.3\pm0.2$, $7.4\pm0.2$, $7.5\pm0.2$, $5.5\pm0.1$, $5.6\pm0.1$, $5.7\pm0.1$, $5.8\pm0.1$, $5.9\pm0.1$, $6.0\pm0.1$, $6.1\pm0.1$, $6.2\pm0.1$, $6.3\pm0.1$, $6.4\pm0.1$, $6.5\pm0.1$, $6.6\pm0.1$, $6.7\pm0.1$, $6.8\pm0.1$, $6.9\pm0.1$, $7.0\pm0.1$, $7.1\pm0.1$, $7.2\pm0.1$, $7.3\pm0.1$, $7.4\pm0.1$, or $7.5\pm0.1$.

In some embodiments, the conductivity of the eluate is adjusted to $2.0\pm1$ mS/cm, $3.0\pm1$ mS/cm, $4.0\pm1$ mS/cm, $5.0\pm1$ mS/cm, $6.0\pm1$ mS/cm, $7.0\pm1$ mS/cm, $8.0\pm1$ mS/cm, $9.0\pm1$ mS/cm, $10\pm1$ mS/cm, $11\pm1$ mS/cm, $12\pm1$ mS/cm, $13\pm1$ mS/cm, $14\pm1$ mS/cm, or $15\pm1$ mS/cm.

I. Anion Exchange Chromatography

In some embodiments, an IgG composition enriched in anti-brain disease-related protein IgG immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein), for example as isolated using the cation exchange chromatographic step described above and, optionally, further purified according to the second cation exchange chromatographic step described above, is further purified by anion exchange chromatography. Any suitable anion exchange resin may be used in the methods provided herein. Non-limiting examples of anion exchange resins suitable for use include, diethylaminoethyl (DEAE), quaternary aminoethyl (QAE), quaternary ammonium (Q), and diethylaminopropyl (ANX) resins. In one embodiment, the anion exchange resin is an ANX resin. In one embodiment, the ANX resin is ANX Sepharose ff resin.

In some embodiments, the method includes applying the anti-brain disease-related protein IgG composition to an anion exchange column and collecting the flow-through fraction, containing the anti-brain disease-related protein immunoglobulins. In some embodiments, this flow-through anion exchange chromatographic step is performed under solution condition including a pH of 5.0 to 8.0 and a conductivity of 0.5 mS/cm to 5.0 mS/cm.

In some embodiments, the anion exchange flow-through step is performed under solution conditions having a pH of about 5.0 to about 7.0, or from about 5.0 to about 6.0, or from about 6.0 to about 8.0, or from about 6.0 to about 7.0, or from about 7.0 to about 8.0. In some embodiments, the anion exchange flow-through step is performed under solution conditions having a pH of about $5.5\pm0.5$, $5.6\pm0.5$, $5.7\pm0.5$, $5.8\pm0.5$, $5.9\pm0.5$, $6.0\pm0.5$, $6.1\pm0.5$, $6.2\pm0.5$, $6.3\pm0.5$, $6.4\pm0.5$, $6.5\pm0.5$, $6.6\pm0.5$, $6.7\pm0.5$, $6.8\pm0.5$, $6.9\pm0.5$, $7.0\pm0.5$, $7.1\pm0.5$, $7.2\pm0.5$, $7.3\pm0.5$, $7.4\pm0.5$, or $7.5\pm0.5$.

In some embodiments, the anion exchange flow-through step is performed under solution conditions having a conductivity of about $1.0\pm0.5$, $1.5\pm0.5$, $2.5\pm0.5$, $3.0\pm0.5$, $3.5\pm0.5$, $4.0\pm0.5$, $4.5\pm0.5$, $1.5\pm1$, $2.0\pm1$, $2.5\pm1$, $3.0\pm1$, $3.5\pm1$, $4.0\pm1$, $2.0\pm1.5$, $2.5\pm1.5$, $3.0\pm1.5$, $3.5\pm1.5$, $2.5\pm2$, or $3.0\pm2$.

In one embodiment, the anion exchange flow-through step is performed under solution conditions having a pH of from about 5.5 to about 7.5 and a conductivity of from about 0.5 mS/cm to about 15 mS/cm. In one embodiment, the anion exchange flow-through step is performed under solution conditions having a pH of from 5.9 to 6.9 and a conductivity of from 1.0 mS/cm to 15 mS/cm. In another embodiment, the anion exchange flow-through step is performed under solution conditions having a pH of from 5.9 to 6.9 and a conductivity of from 1.0 mS/cm to 5.0 mS/cm. In another embodiment, the anion exchange flow-through step is performed under solution conditions having a pH of $6.4\pm0.2$ and a conductivity of from 1.0 mS/cm to 5.0 mS/cm. In another embodiment, the anion exchange flow-through step is performed under solution conditions having a pH of $6.4\pm0.2$ and a conductivity of $2.2\pm1$ mS/cm.

J. Virus Removal and Inactivation

In some embodiments, the methods provided herein for the preparation of an IgG composition enriched in anti-brain disease-related protein immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein) include at least one, preferably at least two, more preferably three viral inactivation and/or removal steps. Non-limiting examples of viral inactivation or removal steps that may be employed with the methods provided herein include, solvent detergent treatment (Horowitz et al., Blood Coagul Fibrinolysis 1994 (5 Suppl 3):S21-S28 and Kreil et al., Transfusion 2003 (43):1023-1028, the disclosures of which are hereby expressly incorporated herein by reference in their entireties for all purposes), nanofiltration (Hamamoto et al., Vox Sang 1989 (56)230-236 and Yuasa et al., J Gen Virol. 1991 (72 (pt 8)):2021-2024, the disclosures of which are hereby expressly incorporated herein by reference in their entireties for all purposes), and low pH incubation at high temperatures (Kempf et al., Transfusion 1991 (31)423-427 and Louie et al., Biologicals 1994 (22):13-19, the disclosure of which is hereby expressly incorporated herein by reference in its entirety for all purposes). In some embodiments, the methods provided herein include S/D treatment, nanofiltration, and incubation at low pH steps.

Viral inactivation or removal steps may be performed on a final enriched IgG composition and/or on any intermediate enriched IgG compositions generated during the manufacturing process. For example, in one embodiment, a viral inactivation or removal step may be performed on a Fraction I supernatant, a Fraction II+III silicon dioxide filter cake extract, a cation exchange eluate fraction, an anion exchange flow-through fraction, an ultrafiltration or diafiltration product, etc.

1. Solvent and Detergent (S/D) Treatment

In order to inactivate various viral contaminants which may be present in plasma-derived or recombinant products, one or more enriched IgG intermediate compositions may be subjected to a solvent detergent (S/D) treatment. Methods for the detergent treatment of plasma-derived fractions are well known in the art (for review see, Pelletier J P et al., Best Pract Res Clin Haematol. 2006; 19(1):205-42, the disclosure of which is expressly incorporated by reference herein in its entirety for all purposes). Generally, any standard S/D treatment may be used in conjunction with the methods provided herein. For example, an exemplary protocol for an S/D treatment is provided below.

In some embodiments, Triton X-100, Tween-20, and tri(n-butyl)phosphate (TNBP) are added to a Factor H intermediate composition at final concentrations of at or about 1.0%, 0.3%, and 0.3%, respectively. The mixture is then stirred at a temperature of between about 18° C. and about 25° C. for at least about an hour.

In one embodiment, the S/D reagents (e.g., Triton X-100, Tween-20, and TNBP) are added by spraying rather than by fluent addition. In other embodiments, the detergent reagents may be added as solids to the enriched IgG intermediate solution, which is being mixed to ensure rapid distribution of the S/D components. In certain embodiments, it is preferable to add solid reagents by sprinkling the solids over a delocalized surface area of the filtrate such that local overconcentration does not occur, such as in fluent addition. In another embodiment, the enriched IgG solution is pumped into a tank where the SD-reagents are already present either in concentrated or diluted form.

2. Nanofiltration

In some embodiments, the methods provided herein include nanofiltration of an enriched IgG composition, or an intermediate thereof, using a suitable nanofiltration device. In certain embodiments, the nanofiltration device will have a mean pore size of from about 15 nm to about 100 nm. Examples of nanofilters suitable for this use include, without limitation, DVD, DV 50, DV 20 (Pall), Viresolve NFP, Viresolve NFR (Millipore), Planova 15N, 20N, 35N, and 75N (Planova). In some embodiments, the nanofilter has a mean pore size of from about 15 nm to about 72 nm, or from about 19 nm to about 35 nm, or about 15 nm, 19 nm, 35 nm, or 72 nm. In some embodiments, the nanofilter has a mean pore size of about 19 nm, such as an Asahi PLANOVA 35N filter, or equivalent thereof.

3. Incubation at Low pH

In some embodiments, the enriched IgG composition, or an intermediate thereof, is incubated at low pH to reduce or inactivate the viral load of the composition. In one embodiment, this is achieved by adjusting the pH of the of the composition to low pH, for example, less than at or about 6.0, and incubating for at least about a week prior to releasing the composition. In a preferred embodiment, the pH of the bulk solution is adjusted to less than at or about 5.5 prior to incubation. In a more preferred embodiment, the pH of the solution is lowered to less than at or about 5.0 prior to incubation. In certain embodiments, the pH of the solution is lowered to less than at or about 6.0 or less than at or about 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, or lower prior to incubation.

In some embodiments, the enriched IgG composition, or an intermediate thereof, is incubated for at least about one week, or at least about 2, 3, 4, or more weeks, or for at least about 1, 2, 3, or more months. In some embodiments, the composition is incubated at a temperature above about 20° C., or above about 25° C., or above about 30° C. In some embodiments, the composition is incubated at a temperature of at or about 20° C., or at or about 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., or higher.

4. Lyophilization and Heat Treatment

In some embodiments, in which the IgG composition enriched in anti-brain disease-related protein IgG (e.g., anti-amyloid beta (anti-Aβ) immunoglobulins, anti-RAGE immunoglobulins, anti-α-synuclein immunoglobulins, or other immunoglobulins specific for a brain disease-related protein) is lyophilized, the method for preparing the composition includes heat treatment of the lyophilized composition. Heat treatments for the inactivation of viruses in compositions of blood factors are well known in the art (for example, see, Piszkiewicz et al., Thromb Res. 1987 Jul. 15; 47(2):235-41; Piszkiewicz et al., Curr Stud Hematol Blood Transfus. 1989; (56):44-54; Epstein and Fricke, Arch Pathol Lab Med. 1990 March; 114(3):335-40, the disclosures of which are hereby expressly incorporated by reference in their entireties for all purposes).

K. Ultrafiltration and Diafiltration

In some embodiments, the methods provided herein include an ultrafiltration step to concentrate and/or formulate the IgG composition enriched in anti-brain disease-related protein IgG (e.g., anti-amyloid beta (anti-Aβ) immunoglobulins, anti-RAGE immunoglobulins, anti-α-synuclein immunoglobulins, or other immunoglobulins specific for a brain disease-related protein). In some embodiments, ultrafiltration is performed using a cassette (e.g., with an open channel screen) and an ultrafiltration membrane having a nominal molecular weight cut off (NMWCO) of less than about 150 kDa or less than about 140, 130, 120, 100, 90, 80, 70, 60, 50, 40, or 30 kDa. In some embodiments, the ultrafiltration membrane has a NMWCO of no more than 50 kDa. In some embodiments, the IgG composition enriched in anti-brain disease-related protein IgG (e.g., anti-amyloid beta (anti-Aβ) immunoglobulins, anti-RAGE immunoglobulins, anti-α-synuclein immunoglobulins, or other immunoglobulins specific for a brain disease-related protein) is concentrated to a final protein concentration of at or about between 0.5% and 25% (w/v), or at or about between 1% and 25% (w/v), or at or about between 2% and 20% (w/v), or at or about between 3% and 15% (w/v), or at or about between 5% and 10% (w/v), or at or about between 9% and 12%, or at or about between 3% and 7% (w/v), or at or about between 8% and 14% (w/v), or at or about between 4% and 6%, or to a final concentration of at or about 0.1%, 0.25%, 0.5%, 1%, 2%, 3%, 4%, 5%, or 6%, 7%, 8%, 9%, 10%, 11%, 12%, 13%, 14%, 15%, 16%, 17%, 18%, 19%, 20%, 21%, 22%, 23%, 24%, 25% or higher.

In some embodiments, prior to and/or after ultrafiltration, buffer exchange may be performed by diafiltration against a solution suitable for intravenous, intramuscular, subcutaneous, intranasal, or other appropriate route for administration of IgG. Typically, the minimum exchange volume is at least about 3 times the original concentrate volume or at least about 4, 5, 6, 7, 8, 9, or more times the original concentrate volume.

In one embodiment, ultra/diafiltration is performed prior to a viral reduction step, e.g., nanofiltration. In another embodiment, ultra/diafiltration is performed after a viral reduction step, e.g., nanofiltration. In one embodiments, a low pH viral reduction step is performed after the ultra/diafiltration step, e.g., while the composition is present in its final formulation.

IV. Plasma-Derived IgG Compositions

In one aspect, IgG compositions enriched in anti-brain disease-related protein immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein) prepared according to any of the methods described herein are provided. In some embodiments, the IgG composition enriched in anti-brain disease-related protein immunoglobulins is an aqueous composition. In some embodiments, the IgG composition enriched in anti-brain disease-related protein immunoglobulins is formulated for pharmaceutical administration, for example by intravenous, intramuscular, subcutaneous, intranasal, or any other appropriate route for therapeutic administration of IgG.

Pharmaceutical carriers and excipients as well as suitable pharmaceutical formulations are well known in the art (see, for example "Pharmaceutical Formulation Development of Peptides and Proteins," Frokjaer et al., Taylor & Francis (2000) or "Handbook of Pharmaceutical Excipients," 3rd edition, Kibbe et al., Pharmaceutical Press (2000)).

In some embodiments, an IgG pharmaceutical composition enriched in anti-brain disease-related protein immunoglobulins may be formulated in lyophilized or stable soluble form. The IgG composition may be lyophilized by a variety of procedures known in the art. Lyophilized formulations are reconstituted prior to use by the addition of one or more pharmaceutically acceptable diluents such as sterile water for injection or sterile physiological saline solution.

Formulations of the IgG composition enriched in anti-brain disease-related protein immunoglobulins are delivered to the individual by any pharmaceutically suitable means of administration. Various delivery systems are known and can be used to administer the composition by any convenient route. In some embodiments, the compositions provided herein are administered systemically. For systemic use, in accordance with some embodiments, IgG is formulated for parenteral (e.g. intravenous, subcutaneous, intramuscular, intraperitoneal, intracerebral, intrapulmonar, intranasal, intravitreal, or transdermal) or enteral (e.g., oral, vaginal or rectal) delivery according to conventional methods. The formulations can be administered continuously by infusion or by bolus injection. Some formulations encompass slow release systems. Preferred routes of administration will depend upon the indication being treated, managed, or prevented. A skilled physician will readily be able to determine the preferred route of administration for the particular affliction being treated, managed, or prevented.

In some embodiments, IgG compositions enriched in anti-amyloid beta (anti-Aβ) IgG immunoglobulins prepared according to any of the methods described herein are provided. In some embodiments, the IgG composition enriched in anti-amyloid beta (anti-Aβ) IgG immunoglobulins is a high titer anti-amyloid β pooled immunoglobulin G. In one embodiment, the high titer anti-amyloid β pooled immunoglobulin G composition contains at least 2-fold greater binding activity for at least one conformer of amyloid β (e.g., an Aβ42 monomer, an Aβ40 CAPS, and/or an Aβ40 fibril) than does a pooled total IgG composition prepared from the blood/plasma of more than a thousand random individuals. In some embodiments, a high titer anti-amyloid β pooled immunoglobulin G composition contains at least 3-fold, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one conformer of amyloid β than does a pooled total IgG composition prepared from the blood/plasma of more than a thousand random individuals. In some embodiments, the binding activity of a high titer anti-amyloid β pooled immunoglobulin G composition is enriched for an anti-amyloid β antibody as compared to the concentration and/or activity of the anti-amyloid β antibody in a commercial plasma-derived IgG composition.

In some embodiments, IgG compositions enriched in anti-amyloid beta 40 (anti-Aβ 40) IgG immunoglobulins prepared according to any of the methods described herein are provided. In some embodiments, the IgG composition enriched in anti-amyloid beta 40 (anti-Aβ 40) IgG immunoglobulins is a high titer anti-amyloid β 40 pooled immunoglobulin G. In one embodiment, the high titer anti-amyloid β 40 pooled immunoglobulin G composition contains at least 2-fold greater binding activity for at least one epitope of amyloid β 40 than does a pooled total IgG composition prepared from the blood/plasma of more than a thousand random individuals. In some embodiments, a high titer anti-amyloid β 40 pooled immunoglobulin G composition contains at least 3-fold, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one epitope of amyloid β 40 than does a pooled total IgG composition prepared from the blood/plasma of more than a thousand random individuals. In some embodiments, the binding activity of a high titer anti-amyloid β 40 pooled immunoglobulin G composition is enriched for an anti-amyloid β 40 antibody as compared to the concentration and/or activity of the anti-amyloid β 40 antibody in a commercial plasma-derived IgG composition.

In some embodiments, IgG compositions enriched in anti-amyloid beta 42 (anti-Aβ 42) IgG immunoglobulins prepared according to any of the methods described herein are provided. In some embodiments, the IgG composition enriched in anti-amyloid beta 42 (anti-Aβ 42) IgG immunoglobulins is a high titer anti-amyloid β 42 pooled immunoglobulin G. In one embodiment, the high titer anti-amyloid β 42 pooled immunoglobulin G composition contains at least 2-fold greater binding activity for at least one epitope of amyloid β 42 than does a pooled total IgG composition prepared from the blood/plasma of more than a thousand random individuals. In some embodiments, a high titer anti-amyloid β 42 pooled immunoglobulin G composition contains at least 3-fold, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one epitope of amyloid β 42 than does a pooled total IgG composition prepared from the blood/plasma of more than a thousand random individuals. In some embodiments, the binding activity of a high titer anti-amyloid β 42 pooled immunoglobulin G composition is enriched for an anti-amyloid β 42 antibody as compared to the concentration and/or activity of the anti-amyloid β 42 antibody in a commercial plasma-derived IgG composition.

In some embodiments, IgG compositions enriched in anti-amyloid beta 40 oligomers (anti-Aβ 40 oligomers) IgG immunoglobulins prepared according to any of the methods described herein are provided. In some embodiments, the IgG composition enriched in anti-amyloid beta 40 oligomers (anti-Aβ 40 oligomers) IgG immunoglobulins is a high titer anti-amyloid β 40 oligomers pooled immunoglobulin G. In one embodiment, the high titer anti-amyloid β 40 oligomers pooled immunoglobulin G composition contains at least 2-fold greater binding activity for at least one epitope of amyloid β 40 oligomers than does a pooled total IgG composition prepared from the blood/plasma of more than a thousand random individuals. In some embodiments, a high titer anti-amyloid β 40 oligomers pooled immunoglobulin G composition contains at least 3-fold, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one epitope of amyloid β 40 oligomers than does a pooled total IgG composition prepared from the blood/plasma of more than a thousand random individuals. In some embodiments, the binding activity of a high titer anti-amyloid β 40 oligomers pooled immunoglobulin G composition is enriched for an anti-amyloid β 40 oligomers antibody as compared to the concentration and/or activity of the anti-amyloid β 40 oligomers antibody in a commercial plasma-derived IgG composition.

In some embodiments, IgG compositions enriched in anti-amyloid beta 40 fibrils (anti-Aβ 40 fibrils) IgG immunoglobulins prepared according to any of the methods described herein are provided. In some embodiments, the IgG composition enriched in anti-amyloid beta 40 fibrils (anti-Aβ 40 fibrils) IgG immunoglobulins is a high titer anti-amyloid β 40 fibrils pooled immunoglobulin G. In one embodiment, the high titer anti-amyloid β 40 fibrils pooled immunoglobulin G composition contains at least 2-fold greater binding activity for at least one epitope of amyloid β 40 fibrils than does a pooled total IgG composition prepared from the blood/plasma of more than a thousand random individuals. In some embodiments, a high titer anti-amyloid β 40 fibrils pooled immunoglobulin G composition contains at least 3-fold, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one epitope of amyloid β 40 fibrils than does a pooled total IgG composition prepared from the blood/plasma of more than a thousand random individuals. In some embodiments, the binding activity of a high titer anti-amyloid β 40 fibrils pooled immunoglobulin G composition is enriched for an anti-amyloid β 40 fibrils antibody as compared to the concentration and/or activity of the anti-amyloid β 40 fibrils antibody in a commercial plasma-derived IgG composition.

In some embodiments, IgG compositions enriched in anti-RAGE IgG immunoglobulins prepared according to any of the methods described herein are provided. In some embodiments, the IgG composition enriched in anti-RAGE IgG immunoglobulins is a high titer anti-RAGE pooled immunoglobulin G. In one embodiment, the high titer anti-RAGE pooled immunoglobulin G composition contains at least 2-fold greater binding activity for at least one epitope of RAGE than does a pooled total IgG composition prepared from the blood/plasma of more than a thousand random individuals. In some embodiments, a high titer anti-RAGE pooled immunoglobulin G composition contains at least 3-fold, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one epitope of RAGE than does a pooled total IgG composition prepared from the blood/plasma of more than a thousand random individuals. In some embodiments, the binding activity of a high titer anti-RAGE pooled immunoglobulin G composition is enriched for an anti-RAGE antibody as compared to the concentration and/ or activity of the anti-RAGE antibody in a commercial plasma-derived IgG composition.

In some embodiments, IgG compositions enriched in anti-α-synuclein IgG immunoglobulins prepared according to any of the methods described herein are provided. In some embodiments, the IgG composition enriched in anti-α-synuclein IgG immunoglobulins is a high titer anti-α-synuclein pooled immunoglobulin G. In one embodiment, the high titer anti-α-synuclein pooled immunoglobulin G composition contains at least 2-fold greater binding activity for at least one epitope of α-synuclein than does a pooled total IgG composition prepared from the blood/plasma of more than a thousand random individuals. In some embodiments, a high titer anti-α-synuclein pooled immunoglobulin G composition contains at least 3-fold, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one epitope of α-synuclein than does a pooled total IgG composition prepared from the blood/plasma of more than a thousand random individuals. In some embodiments, the binding activity of a high titer anti-α-synuclein pooled immunoglobulin G composition is enriched for an anti-α-synuclein antibody as compared to the concentration and/or activity of the anti-α-synuclein antibody in a commercial plasma-derived IgG composition.

In some embodiments, IgG compositions enriched in anti-*Haemophilus influenzea* Type B (Hib) IgG immunoglobulins prepared according to any of the methods described herein are provided. In some embodiments, the IgG composition enriched in anti-Hib IgG immunoglobulins is a high titer anti-Hib pooled immunoglobulin G. In one embodiment, the high titer anti-Hib pooled immunoglobulin G composition contains at least 2-fold greater binding activity for at least one epitope of *Haemophilus influenzea* Type B than does a pooled total IgG composition prepared from the blood/plasma of more than a thousand random individuals. In some embodiments, a high titer anti-Hib pooled immunoglobulin G composition contains at least 3-fold, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one epitope of *Haemophilus influenzea* Type B than does a pooled total IgG composition prepared from the blood/plasma of more than a thousand random individuals. In some embodiments, the binding activity of a high titer anti-Hib pooled immunoglobulin G composition is enriched for an anti-Hib antibody as compared to the concentration and/or activity of the anti-Hib antibody in a commercial plasma-derived IgG composition.

In some embodiments, IgG compositions enriched in anti-Hepatitis B virus (Hbs) IgG immunoglobulins prepared according to any of the methods described herein are provided. In some embodiments, the IgG composition enriched in anti-Hbs IgG immunoglobulins is a high titer anti-Hbs pooled immunoglobulin G. In one embodiment, the high titer anti-Hbs pooled immunoglobulin G composition contains at least 2-fold greater binding activity for at least one epitope of Hepatitis B virus (e.g., an epitope of Hepatitis B Surface Antigen) than does a pooled total IgG composition prepared from the blood/plasma of more than a thousand random individuals. In some embodiments, a high titer anti-Hbs pooled immunoglobulin G composition contains at least 3-fold, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one epitope of Hepatitis B (e.g., an epitope of Hepatitis B Surface Antigen) than does a pooled total IgG composition prepared from the blood/plasma of more than a thousand random individuals. In some embodiments, the binding activity of a high titer anti-Hbs pooled immunoglobulin G composition is enriched for an anti-Hbs antibody as compared to the concentration and/or activity of the anti-Hbs antibody in a commercial plasma-derived IgG composition.

In some embodiments, IgG compositions enriched in anti-poliovirus type 1 mahoney (anti-PV1) IgG immunoglobulins prepared according to any of the methods described herein are provided. In some embodiments, the IgG composition enriched in anti-PV1 IgG immunoglobulins is a high titer anti-PV1 pooled immunoglobulin G. In one embodiment, the high titer anti-PV1 pooled immunoglobulin G composition contains at least 2-fold greater binding activity for at least one epitope of poliovirus than does a pooled total IgG composition prepared from the blood/plasma of more than a thousand random individuals. In some embodiments, a high titer anti-PV1 pooled immunoglobulin G composition contains at least 3-fold, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one epitope of poliovirus than does a pooled total IgG composition prepared from the blood/plasma of more than a thousand random individuals. In some embodiments, the binding activity of a high titer anti-PV1 pooled immunoglobulin G composition is enriched for an anti-PV1 antibody as compared to the concentration and/or activity of the anti-PV1 antibody in a commercial plasma-derived IgG composition.

In some embodiments, IgG compositions enriched in anti-Hepatitis A virus (HAV) IgG immunoglobulins prepared according to any of the methods described herein are provided. In some embodiments, the IgG composition enriched in anti-HAV IgG immunoglobulins is a high titer anti-HAV pooled immunoglobulin G. In one embodiment, the high titer anti-HAV pooled immunoglobulin G composition contains at least 2-fold greater binding activity for at least one epitope of Hepatitis A virus than does a pooled total IgG composition prepared from the blood/plasma of more than a thousand random individuals. In some embodiments, a high titer anti-HAV pooled immunoglobulin G composition contains at least 3-fold, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one epitope of Hepatitis A virus than does a pooled total IgG composition prepared from the blood/plasma of more than a thousand random individuals. In some embodiments, the binding activity of a high titer anti-HAV pooled immunoglobulin G composition is enriched for an anti-HAV antibody as compared to the concentration and/or activity of the anti-HAV antibody in a commercial plasma-derived IgG composition.

In some embodiments, IgG compositions enriched in anti-cytomegalovirus (anti-CMV) IgG immunoglobulins prepared according to any of the methods described herein are provided. In some embodiments, the IgG composition enriched in anti-CMV IgG immunoglobulins is a high titer anti-CMV pooled immunoglobulin G. In one embodiment, the high titer anti-CMV pooled immunoglobulin G composition contains at least 2-fold greater binding activity for at least one epitope of cytomegalovirus than does a pooled total IgG composition prepared from the blood/plasma of more than a thousand random individuals. In some embodiments, a high titer anti-CMV pooled immunoglobulin G composition contains at least 3-fold, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one epitope of cytomegalovirus than does a pooled total IgG composition prepared from the blood/plasma of more than a thousand random individuals. In some embodiments, the binding activity of a high titer anti-CMV pooled immunoglobulin G composition is enriched for an anti-CMV antibody as compared to the concentration and/or activity of the anti-CMV antibody in a commercial plasma-derived IgG composition.

In some embodiments, IgG compositions enriched in anti-tetanus IgG immunoglobulins prepared according to any of the methods described herein are provided. In some embodiments, the IgG composition enriched in anti-tetanus IgG immunoglobulins is a high titer anti-tetanus pooled immunoglobulin G. In one embodiment, the high titer anti-tetanus pooled immunoglobulin G composition contains at least 2-fold greater binding activity for at least one epitope of tetanus than does a pooled total IgG composition prepared from the blood/plasma of more than a thousand random individuals. In some embodiments, a high titer anti-tetanus pooled immunoglobulin G composition contains at least 3-fold, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one epitope of tetanus than does a pooled total IgG composition prepared from the blood/plasma of more than a thousand random individuals. In some embodiments, the binding activity of a high titer anti-tetanus pooled immunoglobulin G composition is enriched for an anti-tetanus antibody as compared to the concentration and/or activity of the anti-tetanus antibody in a commercial plasma-derived IgG composition.

In some embodiments, IgG compositions enriched in anti-parvo B19 virus IgG immunoglobulins prepared according to any of the methods described herein are provided. In some embodiments, the IgG composition enriched in anti-parvo B19 IgG immunoglobulins is a high titer anti-parvo B19 pooled immunoglobulin G. In one embodiment, the high titer anti-parvo B19 pooled immunoglobulin G composition contains at least 2-fold greater binding activity for at least one epitope of parvo B19 virus than does a pooled total IgG composition prepared from the blood/plasma of more than a thousand random individuals. In some embodiments, a high titer anti-parvo B19 pooled immunoglobulin G composition contains at least 3-fold, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one epitope of parvo B19 virus than does a pooled total IgG composition prepared from the blood/plasma of more than a thousand random individuals. In some embodiments, the binding activity of a high titer anti-parvo B19 pooled immunoglobulin G composition is enriched for an anti-parvo B19 antibody as compared to the concentration and/or activity of the anti-parvo B19 antibody in a commercial plasma-derived IgG composition.

In some embodiments, IgG compositions enriched in *Corynebacterium diphtheriae* (anti-*diphtheriae*) IgG immunoglobulins prepared according to any of the methods described herein are provided. In some embodiments, the IgG composition enriched in anti-*diphtheriae* IgG immunoglobulins is a high titer anti-*diphtheriae* pooled immunoglobulin G. In one embodiment, the high titer anti-*diphtheriae* pooled immunoglobulin G composition contains at least 2-fold greater binding activity for at least one epitope of *Corynebacterium diphtheriae* than does a pooled total IgG composition prepared from the blood/plasma of more than a thousand random individuals. In some embodiments, a high titer anti-*diphtheriae* pooled immunoglobulin G composition contains at least 3-fold, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one epitope of *Corynebacterium diphtheriae* than does a pooled total IgG composition prepared from the blood/plasma of more than a thousand random individuals. In some embodiments, the binding activity of a high titer anti-*diphtheriae* pooled immunoglobulin G composition is enriched for an anti-*diphtheriae* antibody as compared to the concentration and/or activity of the anti-*diphtheriae* antibody in a commercial plasma-derived IgG composition.

A. Supplemented Plasma-Derived IgG Compositions

In some embodiments, the enriched compositions provided herein can be used to supplement traditional plasma-derived IgG compositions to achieve an increased titer for a specific anti-brain disease-related protein immunoglobulin. In certain embodiments, a total plasma-derived IgG composition (e.g., one that is not enriched in anti-brain disease-related protein immunoglobulins) is supplemented with the enriched compositions described herein to achieve a final anti-brain disease-related protein immunoglobulin titer that is about 2-fold, 3-fold, 4-fold, 5-fold, 6-fold, 7-fold, 8-fold, 9-fold, 10-fold, 11-fold, 12-fold, 13-fold, 14-fold, 15-fold, 20-fold, 25-fold, 30-fold, 35-fold, 40-fold, 45-fold, 50-fold, or more-fold higher than would normally be found in the composition. Thus, it is contemplated that less of the supplemented plasma-derived IgG composition could be administered for the treatment of a symptom of the related brain disease.

For example, an IVIG composition that is supplemented with 8-fold higher of an anti-brain disease-related protein immunoglobulins (e.g., prepared by adding about 1 volume of an 80-fold enriched IgG composition to 10 volumes of the normal IVIG) may be administered for the treatment of a symptom of the brain disease at a dosage as low as 25 mg/kg to 50 mg/kg, greatly reducing the demand of IgG for the therapy of a symptom of brain diseases.

In some embodiments, IgG compositions are provided that are supplemented with from about 2-fold higher to about 50-fold higher titer of one or more anti-brain disease-related protein immunoglobulin. In some embodiments, the supplemented composition had about 2-fold higher to about 25-fold higher titer, about 2-fold higher to about 20-fold higher titer, about 2-fold higher to about 15-fold higher titer, about 2-fold higher to about 10-fold higher titer, about 2-fold higher to about 5-fold higher titer of one or more anti-brain disease-related protein immunoglobulin.

Advantageously, because the titer of a specific anti-brain disease-related protein immunoglobulin can be determined (e.g., by ELISA or other suitable method known in the art), a non-enriched IgG composition can be supplemented with any concentration of the brain-disease related-protein immunoglobulin desired. In this fashion, therapeutics can be tailored to include a specific titer of one or more anti-brain disease-related protein immunoglobulins.

V. Treatment of Brain Diseases and Disorders

In one aspect, methods are provided for treating a brain disease in a subject in need thereof by administering a therapeutically effective amount of an IgG composition enriched in anti-brain disease-related protein immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein) prepared according to any of the methods described herein. In some embodiments, the brain disease is a disease or disorder that is associated with the mis-expression (e.g., over- or under-expression) of a protein in the brain, a mutated protein normally or abnormally expressed in the brain, a protein that is abnormally located in the brain (e.g., mis-located or over-located as in the deposition of protein plaques on the cerebral cortex). In some embodiments, the brain disease or disorder is associated with a protein selected from the group consisting of amyloid beta (Aβ), alpha-synuclein (SNCA), Major Prion Protein (PrP), Huntingtin (HD), Prolactin (PRL), Cystatin C (CST3), and advanced glycosylation end product-specific receptor (RAGE). Table 1 provides non-limiting examples of brain disease-related proteins and their corresponding brain disease.

In some embodiments, the subject is administered an IgG composition enriched in anti-brain disease-related protein IgG immunoglobulin, where the brain disease-related protein is selected from the group consisting of amyloid beta (Aβ), alpha-synuclein (SNCA), Major Prion Protein (PrP), Huntingtin (HD), Prolactin (PRL), Cystatin C (CST3), and advanced glycosylation end product-specific receptor (RAGE). In some embodiments, the IgG composition enriched in more than one type of anti-brain disease-related protein IgG immunoglobulin. For example, in some embodiments, the IgG composition is enriched in two or more of anti-amyloid beta (anti-Aβ) immunoglobulins, anti-RAGE immunoglobulins, and anti-α-synuclein immunoglobulins.

In current trials investigating the therapeutic effect of IVIG administration on brain diseases, subjects are administered between 0.4 g/kg body weight and 2.0 g/kg body weight IVIG per dosage. In some embodiments, the increased titers of the anti-brain disease-related protein IgG in the compositions provided herein can reduce the amount of IgG administered to these patients, for example, by up to 100-fold.

In some embodiments, an IgG composition enriched in anti-brain disease-related protein immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein) obtainable by or prepared according to any of the methods described herein, is administered for the therapy of a brain disease or disorder at a dosage of from about 0.25 mg/kg to about 400 mg/kg. In some embodiments, the enriched IgG composition is administered at a dosage of from about 1.0 mg/kg to about 200 mg/kg. In some embodiments, the enriched IgG composition is administered at a dosage of from about 2.5 mg/kg to about 200 mg/kg. In some embodiments, the enriched IgG composition is administered at a dosage of from about 2.5 mg/kg to about 100 mg/kg. In some embodiments, the enriched IgG composition is administered at a dosage of from about 2.5 mg/kg to about 50 mg/kg. In some embodiments, the enriched IgG composition is administered at a dosage of from about 2.5 mg/kg to about 20 mg/kg. In some embodiments, the enriched IgG composition is administered at a dosage of about 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, or greater.

In other embodiments, the enriched compositions provided herein can be used to supplement traditional plasma-derived IgG compositions to achieve an increased titer for a specific anti-brain disease-related protein immunoglobulin. In certain embodiments, a total plasma-derived IgG composition (e.g., one that is not enriched in anti-brain disease-related protein immunoglobulins) is supplemented with the enriched compositions described herein to achieve a final anti-brain disease-related protein immunoglobulin titer that is about 2-fold, 3-fold, 4-fold, 5-fold, 6-fold, 7-fold, 8-fold, 9-fold, 10-fold, 11-fold, 12-fold, 13-fold, 14-fold, 15-fold, 20-fold, 25-fold, 30-fold, 35-fold, 40-fold, 45-fold, 50-fold, or more-fold higher than would normally be found in the composition. Thus, it is contemplated that less of the supplemented plasma-derived IgG composition could be administered for the treatment of a symptom of the related brain disease.

For example, an IVIG composition that is supplemented with 8-fold higher of an anti-brain disease-related protein immunoglobulins (e.g., prepared by adding about 1 volume of an 80-fold enriched IgG composition to 10 volumes of the normal IVIG) may be administered for the treatment of a symptom of the brain disease at a dosage as low as 25 mg/kg to 50 mg/kg, greatly reducing the demand of IgG for the therapy of a symptom of brain diseases.

Accordingly, in some embodiments, a supplemented IgG composition is administered for the therapy of a symptom of a brain disease at a dosage of from about 10 mg/kg to about 400 mg/kg. In some embodiments, the enriched IgG composition is administered at a dosage of from about 10.0 mg/kg to about 150 mg/kg. In some embodiments, the enriched IgG composition is administered at a dosage of from about 10 mg/kg to about 100 mg/kg. In some embodiments, the enriched IgG composition is administered at a dosage of from about 25 mg/kg to about 150 mg/kg. In some embodiments, the enriched IgG composition is administered at a dosage of from about 25 mg/kg to about 100 mg/kg. In some embodiments, the enriched IgG composition is administered at a dosage of from about 25 mg/kg to about 50 mg/kg. In some embodiments, the enriched IgG composition is administered at a dosage of about 12.5±10 mg/kg, 15±10 mg/kg, 17.5±10 mg/kg, 20±10 mg/kg, 25±10 mg/kg, 30±10 mg/kg, 35±10 mg/kg, 40±10 mg/kg, 45±10 mg/kg, 50±10 mg/kg, 60±10 mg/kg, 70±10 mg/kg, 80±10 mg/kg, 90±10 mg/kg, 100±10 mg/kg, 125±10 mg/kg, 150±10 mg/kg, 175±10 mg/kg, 200±10 mg/kg, 225 mg/kg, 250 mg/kg, 275 mg/kg, 300 mg/kg, 325 mg/kg, 350 mg/kg, 375 mg/kg, 400 mg/kg, or greater.

A. Alzheimer's Disease

IVIG has been used in the treatment of Alzheimer's disease. It has been proposed that IVIG contains antibodies against β-amyloid. Relkin et al. 2009 (Neurobiol. Aging 30(11): 1728-36). In this study, pooled human IgG was administered intravenously (IVIG therapy) to eight subjects diagnosed with mild Alzheimer's disease (AD). The patients received IVIG therapy for 6 months, discontinued treatment, and then resumed treatment for 9 more months. It was found that β-amyloid antibodies in the serum from AD patients increased in proportion to IVIG dose and plasma levels of β-amyloid increased transiently after each infusion. After 6 months of treatment, mini-mental state tests were performed on the patients. The mini-mental state scores increased an average of 2.5 points after 6 months, returned to baseline during washout and remained stable during subsequent IVIG treatment.

In some embodiments, methods are provided for the treatment of a symptom of Alzheimer's disease in a subject in need thereof. The method includes administering to the subject a therapeutically effective amount of an IgG composition enriched in anti-brain disease-related protein immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein) obtainable by or prepared according to any of the methods described herein.

In a specific embodiment, the method includes administration to the subject a therapeutically effective amount of an IgG composition enriched in anti-amyloid beta (anti-Aβ) immunoglobulins obtainable by or prepared according to any of the methods described herein. In some embodiments, the composition contains at least 2-fold, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one conformer of amyloid β than does a pooled total IgG composition prepared from the blood/plasma of more than a thousand random individuals. In some embodiments, the composition enriched for an anti-amyloid β antibody as compared to the concentration and/or activity of the anti-amyloid β antibody in a commercial plasma-derived IgG composition.

In another specific embodiment, the method includes administration to the subject a therapeutically effective amount of an IgG composition enriched in anti-RAGE immunoglobulins obtainable by or prepared according to any of the methods described herein. In some embodiments, the composition contains at least 2-fold, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one epitope of a RAGE protein than does a pooled total IgG composition prepared from the blood/plasma of more than a thousand random individuals. In some embodiments, the composition enriched for an anti-RAGE antibody as compared to the concentration and/or activity of the anti-RAGE antibody in a commercial plasma-derived IgG composition.

Typical intravenous dosing of IgG in human Alzheimer's trials ranges from about 200 mg/kg to about 400 mg/kg every two weeks. If treatment at these dosages was to be approved for the therapy of Alzheimer's symptoms, it is unlikely that the world supply of plasma-derived IgG, which is already regulated for currently approved treatments in some countries, could meet the increased demand. However, the methods described herein provide a new supply of plasma-derived immunoglobulins highly enriched in anti-Alzheimer's related protein immunoglobulins (e.g., anti-Aβ immunoglobulin IgG and anti-RAGE immunoglobulin IgG), which does not affect the manufacturing process or yield of currently manufactured IgG products (e.g., IVIG). Advantageously, it may be possible to administer these IgG compositions enriched in anti-Aβ immunoglobulins and anti-RAGE immunoglobulins at lower dosages because of their high anti-Alzheimer's related protein immunoglobulin content.

For example, it is shown in Example 9 that IgG compositions having 20-fold higher anti-RAGE and 80-fold higher anti-Aβ immunoglobulin titers can be prepared in large scale according to the methods described herein. Thus, it may be possible to administer effective therapy for symptoms of Alzheimer's using these compositions at 20-fold to 80-fold lower dosages (e.g., at dosages as low as 2.5 mg/kg to 5.0 mg/kg).

Accordingly, in some embodiments, an IgG composition enriched in anti-brain disease-related protein immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein) obtainable by or prepared according to any of the methods described herein, is administered for the therapy of a symptom of Alzheimer's disease at a dosage of from about 0.25 mg/kg to about 400 mg/kg. In some embodiments, the enriched IgG composition is administered at a dosage of from about 1.0 mg/kg to about 200 mg/kg. In some embodiments, the enriched IgG composition is administered at a dosage of from about 2.5 mg/kg to about 200 mg/kg. In some embodiments, the enriched IgG composition is administered at a dosage of from about 2.5 mg/kg to about 100 mg/kg. In some embodiments, the enriched IgG composition is administered at a dosage of from about 2.5 mg/kg to about 50 mg/kg. In some embodiments, the enriched IgG composition is administered at a dosage of from about 2.5 mg/kg to about 20 mg/kg. In some embodiments, the enriched IgG composition is administered at a dosage of about 12.5±10 mg/kg, 15±10 mg/kg, 17.5±10 mg/kg, 20±10 mg/kg, 25±10 mg/kg, 30±10 mg/kg, 35±10 mg/kg, 40±10 mg/kg, 45±10 mg/kg, 50±10 mg/kg, 60±10 mg/kg, 70±10 mg/kg, 80±10 mg/kg, 90±10 mg/kg, 100±10 mg/kg, 125±10 mg/kg, 150±10 mg/kg, 175±10 mg/kg, 200±10 mg/kg, 225±10 mg/kg, 250±10 mg/kg, 275±10 mg/kg, 300±10 mg/kg, 325±10 mg/kg, 350±10 mg/kg, 375±10 mg/kg, 400±10 mg/kg, or greater.

In other embodiments, the enriched compositions provided herein can be used to supplement traditional plasma-derived IgG compositions to achieve an increased titer for a specific anti-Alzheimer's related protein immunoglobulin. In certain embodiments, a total plasma-derived IgG composition (e.g., one that is not enriched in anti-brain disease-related protein immunoglobulins) is supplemented with the enriched compositions described herein to achieve a final anti-brain disease-related protein immunoglobulin titer that is about 2-fold, 3-fold, 4-fold, 5-fold, 6-fold, 7-fold, 8-fold, 9-fold, 10-fold, 11-fold, 12-fold, 13-fold, 14-fold, 15-fold, 20-fold, 25-fold, 30-fold, 35-fold, 40-fold, 45-fold, 50-fold, or more-fold higher than would normally be found in the composition. Thus, it is contemplated that less of the supplemented plasma-derived IgG composition could be administered for the treatment of a symptom of Alzheimer's disease.

For example, an IVIG composition that is supplemented with 8-fold higher anti-amyloid beta (anti-Aβ) and/or anti-RAGE immunoglobulins (e.g., prepared by adding about 1 volume of an 80-fold enriched IgG composition to 10 volumes of the normal IVIG) may be administered for the treatment of a symptom of Alzheimer's disease at a dosage as low as 25 mg/kg to 50 mg/kg, greatly reducing the demand of IgG for the therapy of a symptom of Alzheimer's disease.

Accordingly, in some embodiments, a supplemented IgG composition is administered for the therapy of a symptom of Alzheimer's disease at a dosage of from about 10 mg/kg to about 200 mg/kg. In some embodiments, the enriched IgG composition is administered at a dosage of from about 10.0 mg/kg to about 150 mg/kg. In some embodiments, the enriched IgG composition is administered at a dosage of from about 10 mg/kg to about 100 mg/kg. In some embodiments, the enriched IgG composition is administered at a dosage of from about 25 mg/kg to about 150 mg/kg. In some embodiments, the enriched IgG composition is administered at a dosage of from about 25 mg/kg to about 100 mg/kg. In some embodiments, the enriched IgG composition is administered at a dosage of from about 25 mg/kg to about 50 mg/kg. In some embodiments, the enriched IgG composition is administered at a dosage of about 12.5±10 mg/kg, 15±10 mg/kg, 17.5±10 mg/kg, 20±10 mg/kg, 25±10 mg/kg, 30±10 mg/kg, 35±10 mg/kg, 40±10 mg/kg, 45±10 mg/kg, 50±10 mg/kg, 60±10 mg/kg, 70±10 mg/kg, 80±10 mg/kg, 90±10 mg/kg, 100±10 mg/kg, 125±10 mg/kg, 150±10 mg/kg, 175±10 mg/kg, 200±10 mg/kg, or greater.

B. Parkinson's Disease

Parkinson's disease (PD) is a degenerative disorder of the CNS. PD is notably linked to a decrease in motor control. The loss of motor control caused by PD results from the death of dopamine-generating cells in the substantia nigra, a region of the midbrain. Early in the progression of the disease, the most common symptoms include shaking, rigidity, slowness of movement and difficulty with walking and gait. As the disease progresses, cognitive and behavioral problems arise, with dementia occurring in the advanced stages of the disease. Additional symptoms include sensory, sleep and emotional problems. PD is more common in the elderly, with symptoms most commonly occurring after the age of 50.

There are numerous transgenic mouse models for PD. These models include, for example, Park2 (parkin) transgenic strains, LRRK2 transgenic strains, and synuclein transgenic strains (Jackson Laboratories, Bar Harbor, Me.). In addition to transgenic models, parkinsonian symptoms can also be induced in mice by administering the compounds MPTP, rotenone, paraquat, or maneb.

In some embodiments, methods are provided for the treatment of a symptom of Parkinson's disease in a subject in need thereof. The method includes administering to the subject a therapeutically effective amount of an IgG composition enriched in anti-brain disease-related protein immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein) obtainable by or prepared according to any of the methods described herein.

In a specific embodiment, the method includes administration to the subject a therapeutically effective amount of an IgG composition enriched in anti-α-synuclein immunoglobulins obtainable by or prepared according to any of the methods described herein. In some embodiments, the composition contains at least 2-fold, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, or more-fold greater binding activity for at least one epitope of an α-synuclein protein than does a pooled total IgG composition prepared from the blood/plasma of more than a thousand random individuals. In some embodiments, the composition enriched for an anti-α-synuclein antibody as compared to the concentration and/or activity of the anti-α-synuclein antibody in a commercial plasma-derived IgG composition.

In some embodiments, an IgG composition enriched in anti-brain disease-related protein immunoglobulins (e.g., anti-amyloid beta (anti-Aβ) immunoglobulins, anti-RAGE immunoglobulins, anti-α-synuclein immunoglobulins, or other immunoglobulins specific for a brain disease-related protein) obtainable by or prepared according to any of the methods described herein, is administered for the therapy of a symptom of Parkinson's disease at a dosage of from about 0.25 mg/kg to about 400 mg/kg. In some embodiments, the enriched IgG composition is administered at a dosage of from about 1.0 mg/kg to about 200 mg/kg. In some embodiments, the enriched IgG composition is administered at a dosage of from about 2.5 mg/kg to about 200 mg/kg. In some embodiments, the enriched IgG composition is administered at a dosage of from about 2.5 mg/kg to about 100 mg/kg. In some embodiments, the enriched IgG composition is administered at a dosage of from about 2.5 mg/kg to about 50 mg/kg. In some embodiments, the enriched IgG composition is administered at a dosage of from about 2.5 mg/kg to about 20 mg/kg. In some embodiments, the enriched IgG composition is administered at a dosage of about 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, or greater.

In other embodiments, the enriched compositions provided herein can be used to supplement traditional plasma-derived IgG compositions to achieve an increased titer for a specific anti-Parkinson's related protein immunoglobulin. In certain embodiments, a total plasma-derived IgG composition (e.g., one that is not enriched in anti-brain disease-related protein immunoglobulins) is supplemented with the enriched compositions described herein to achieve a final anti-brain disease-related protein immunoglobulin titer that is about 2-fold, 3-fold, 4-fold, 5-fold, 6-fold, 7-fold, 8-fold, 9-fold, 10-fold, 11-fold, 12-fold, 13-fold, 14-fold, 15-fold, 20-fold, 25-fold, 30-fold, 35-fold, 40-fold, 45-fold, 50-fold, or more-fold higher than would normally be found in the composition. Thus, it is contemplated that less of the supplemented plasma-derived IgG composition could be administered for the treatment of a symptom of Alzheimer's disease.

For example, an IVIG composition that is supplemented with 8-fold higher anti-α-synuclein (SNCA) immunoglobulins (e.g., prepared by adding about 1 volume of an 80-fold enriched IgG composition to 10 volumes of the normal IVIG) may be administered for the treatment of a symptom of Parkinson's disease at a dosage as low as 25 mg/kg to 50 mg/kg, greatly reducing the demand of IgG for the therapy of a symptom of Parkinson's disease.

Accordingly, in some embodiments, a supplemented IgG composition is administered for the therapy of a symptom of Parkinson's disease at a dosage of from about 10 mg/kg to about 400 mg/kg. In some embodiments, the enriched IgG composition is administered at a dosage of from about 10.0 mg/kg to about 150 mg/kg. In some embodiments, the enriched IgG composition is administered at a dosage of from about 10 mg/kg to about 100 mg/kg. In some embodiments, the enriched IgG composition is administered at a dosage of from about 25 mg/kg to about 150 mg/kg. In some embodiments, the enriched IgG composition is administered at a dosage of from about 25 mg/kg to about 100 mg/kg. In some embodiments, the enriched IgG composition is administered at a dosage of from about 25 mg/kg to about 50 mg/kg. In some embodiments, the enriched IgG composition is administered at a dosage of about 12.5±10 mg/kg, 15±10 mg/kg, 17.5±10 mg/kg, 20±10 mg/kg, 25±10 mg/kg, 30±10 mg/kg, 35±10 mg/kg, 40±10 mg/kg, 45±10 mg/kg, 50±10 mg/kg, 60±10 mg/kg, 70±10 mg/kg, 80±10 mg/kg, 90±10 mg/kg, 100±10 mg/kg, 125±10 mg/kg, 150±10 mg/kg, 175±10 mg/kg, 200±10 mg/kg, 225 mg/kg, 250 mg/kg, 275 mg/kg, 300 mg/kg, 325 mg/kg, 350 mg/kg, 375 mg/kg, 400 mg/kg, or greater.

VI. Treatment of Infectious Diseases

In one aspect, methods are provided for treating an infectious disease in a subject in need thereof by administering a therapeutically effective amount of an IgG composition enriched in anti-infectious disease-related agent immunoglobulins (e.g., anti-Hib immunoglobulins, anti-Hbs immunoglobulins, anti-PV1 immunoglobulins, anti-HAV immunoglobulins, anti-CMV immunoglobulins, anti-tetanus immunoglobulins, anti-parvo B19 immunoglobulins, or anti-*diphtheriae* immunoglobulins) prepared according to any of the methods described herein.

In some embodiments, the subject is administered an IgG composition enriched in anti-infectious disease-related agent IgG immunoglobulin, where the infectious disease agent is selected from the group consisting of *Haemophilus influenzae* Type B (Hib), hepatitis B virus (HBV), hepatitis A virus (HAV), poliovirus (PV), cytomegaloviruse (CMV), *Clostridium tetani* (tetanus), parvovirus B19, or *Corynebacterium diphtheriae* (*diphtheriae*). In some embodiments, the IgG composition enriched in more than one type of anti-infectious disease-related agent IgG immunoglobulin. In some embodiments, the increased titers of the anti-infectious disease-related agent IgG in the compositions provided herein can reduce the amount of IgG administered to patients, for example, by up to 100-fold.

In some embodiments, an IgG composition enriched in anti-infectious disease-related agent immunoglobulins (e.g., anti-Hib immunoglobulins, anti-Hbs immunoglobulins, anti-PV1 immunoglobulins, anti-HAV immunoglobulins, anti-CMV immunoglobulins, anti-tetanus immunoglobulins, anti-parvo B19 immunoglobulins, or anti-*diphtheriae* immunoglobulins) obtainable by or prepared according to any of the methods described herein, is administered for the therapy of an infectious disease at a dosage of from about 0.25 mg/kg to about 400 mg/kg. In some embodiments, the enriched IgG composition is administered at a dosage of from about 1.0 mg/kg to about 200 mg/kg. In some embodiments, the enriched IgG composition is administered at a dosage of from about 2.5 mg/kg to about 200 mg/kg. In some embodiments, the enriched IgG composition is administered at a dosage of from about 2.5 mg/kg to about 100 mg/kg. In some embodiments, the enriched IgG composition is administered at a dosage of from about 2.5 mg/kg to about 50 mg/kg. In some embodiments, the enriched IgG composition is administered at a dosage of from about 2.5 mg/kg to about 20 mg/kg. In some embodiments, the enriched IgG composition is administered at a dosage of about 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, or greater.

In other embodiments, the enriched compositions provided herein can be used to supplement traditional plasma-derived IgG compositions to achieve an increased titer for a specific anti-infectious disease-related agent immunoglobulin. In certain embodiments, a total plasma-derived IgG composition (e.g., one that is not enriched in anti-infectious disease-related agent immunoglobulins) is supplemented with an enriched composition described herein to achieve a final anti-infectious disease-related agent immunoglobulin titer that is about 2-fold, 3-fold, 4-fold, 5-fold, 6-fold, 7-fold, 8-fold, 9-fold, 10-fold, 11-fold, 12-fold, 13-fold, 14-fold, 15-fold, 20-fold, 25-fold, 30-fold, 35-fold, 40-fold, 45-fold, 50-fold, or more-fold higher than would normally be found in the composition. Thus, it is contemplated that less of the supplemented plasma-derived IgG composition could be administered for the treatment of a symptom of the related infectious disease.

For example, an IVIG composition that is supplemented with 8-fold higher of an anti-infectious disease-related agent immunoglobulins (e.g., prepared by adding about 1 volume of an 80-fold enriched IgG composition to 10 volumes of the normal IVIG) may be administered for the treatment of a symptom of the infectious disease at a dosage as low as 25 mg/kg to 50 mg/kg, greatly reducing the demand of IgG for the therapy of a symptom of infectious diseases.

Accordingly, in some embodiments, a supplemented IgG composition is administered for the therapy of a symptom of an infectious disease at a dosage of from about 10 mg/kg to about 400 mg/kg. In some embodiments, the enriched IgG composition is administered at a dosage of from about 10.0 mg/kg to about 150 mg/kg. In some embodiments, the enriched IgG composition is administered at a dosage of from about 10 mg/kg to about 100 mg/kg. In some embodiments, the enriched IgG composition is administered at a dosage of from about 25 mg/kg to about 150 mg/kg. In some embodiments, the enriched IgG composition is administered at a dosage of from about 25 mg/kg to about 100 mg/kg. In some embodiments, the enriched IgG composition is administered at a dosage of from about 25 mg/kg to about 50 mg/kg. In some embodiments, the enriched IgG composition is administered at a dosage of about 12.5±10 mg/kg, 15±10 mg/kg, 17.5±10 mg/kg, 20±10 mg/kg, 25±10 mg/kg, 30±10 mg/kg, 35±10 mg/kg, 40±10 mg/kg, 45±10 mg/kg, 50±10 mg/kg, 60±10 mg/kg, 70±10 mg/kg, 80±10 mg/kg, 90±10 mg/kg, 100±10 mg/kg, 125±10 mg/kg, 150±10 mg/kg, 175±10 mg/kg, 200±10 mg/kg, 225 mg/kg, 250 mg/kg, 275 mg/kg, 300 mg/kg, 325 mg/kg, 350 mg/kg, 375 mg/kg, 400 mg/kg, or greater.

VII. Examples

The following examples are provided by way of illustration only and not by way of limitation. Those of skill in the art will readily recognize a variety of non-critical parameters that could be changed or modified to yield essentially the same or similar results.

Example 1—Identification of Brain Disease-Related Immunoglobulins in High Salt Wash Fraction Formed During Chromatographic Regeneration To identify a method for preparing a pooled immunoglobulin G composition enriched in anti-amyloid beta (Aβ) immunoglobulins, pooled human plasma containing a high titer of anti-Aβ immunoglobulins was used as a starting material for the preparation of a plasma-derived IgG composition. The pooled human plasma was fractionated with ethanol according to standard conditions and then IgG in the resulting plasma fraction was further enriched by chromatography, as outlined in FIG. 1. However, analysis of the final product revealed that, unlike the starting plasma pool, the pooled human immunoglobulin G composition was not enriched in anti-Aβ immunoglobulins.

Because the final composition did not contain the expected high titer of anti-Aβ immunoglobulins, it was contemplated that these immunoglobulins were being partially separated at a step in the purification process that results in a loss in yield. One such candidate step is cation exchange chromatography step 110, which results in a loss of less than 5% of the total immunoglobulin G content of the starting Cohn plasma pool. It was deemed possible that the buffer used to elute immunoglobulins from the cation exchange resin in chromatographic step 110, does not have sufficient ionic strength (5.0±0.2 mS/cm) at pH 8.5 to elute this fraction of IgG. Thus, the 2 M sodium chloride wash fraction, generated during regeneration of the cation exchange resin was investigated. The overall IgG content and pattern of sialylation in the 2 M sodium chloride wash fraction were also investigated.

Results of these analyses, described in detail below, demonstrate that, as compared with the main IgG fraction recovered in the first cation exchange eluate fraction, the 2 M wash fraction: (i) had a different IgG subclass distribution, including increased levels of $IgG_3$; (ii) contained higher specific binding activities against all plate-immobilized Aβ conformers investigated, indicating a higher relative concentration of anti-Aβ immunoglobulins; and (iii) contained increased relative levels of monosialylated $IgG_1$ N-glycans. The molecular size distribution profile of the 2 M sodium chloride wash fraction revealed higher levels of immunoglobulin dimers and polymers, which is at least partially explained by the higher relative IgM concentration in the wash fraction. The data presented below provide comprehensive evidence that the IgG contained in this waste fraction have higher binding to all Aβ conformers and higher average levels of sialylated Fc glycans than the IgG of the main cation exchange eluate fraction.

Example 2—ELISA Analysis of Amyloid Beta Binding in the Eluate and High Salt Wash Fractions Formed During Cation Exchange Chromatography Frozen samples of eight cation exchange eluates and corresponding 2 M wash fractions formed during large scale preparation of a plasma-derived IgG composition were used for the analyses described below. Prior to analysis, the samples were thawed, aliquoted, and re-frozen to ensure the integrity of the material used for each analysis was the same.

Human β-amyloid peptide (1-42) (Aβ42) (Calbiochem; PP69 or American Peptide; 62-0-80) was dissolved for coating without further treatment in trifluoroacetic acid (250 g/25 μL TFA or formic acid). Higher order β-amyloid preparations, e.g., soluble cross-linked β-amyloid protein species (CAPS) and Aβ fibrils, were obtained from Brian O'Nuallain (University of Knoxville, Tenn.) and prepared as published (O'Nuallain B. et al., Biochemistry 47, 12254-12256 (2008), the content of which is hereby expressly incorporated by reference in its entirety for all purposes, and in particular for all teachings related to the generation of higher order β-amyloid preparations). Buffers used in the subsequent ELISA analysis of Aβ binding are described in Table 2.

TABLE 2

Buffers used for anti-Aβ ELISA analyses.

| Buffer | Formulation |
| --- | --- |
| Coating buffer | 0.1M NaHCO3, 0.1M Na2CO3; dissolved in HPLC-grade water; pH 9.5 with 3M HCl |
| Washing buffer (PBST) | 0.8% NaCl, 0.02% KCl, 0.02% KH2PO4, 0.126% Na2HPO4×2 H2O, 0.05% Tween 20, pH 7.0-7.4 |
| Blocking/dilution buffer "gelatine" | 0.1% gelatine, 2 mM benzamidine in PBST |
| Blocking/dilution buffer "milk" | 0.1% non-fat dry milk, 2 mM benzamidine in PBST |
| Blocking/dilution buffer "hSA" | 1% hSA, 2 mM benzamidine in PBST |
| Blocking/dilution buffer "BSA" | 0.1% BSA, 2 mM benzamidine in PBST |
| Low conductivity dilution buffer | 20 mM HEPES, pH 7.4; 1% hSA, 2 mM benzamidine, 0.1% Tween 20 |
| Stopping solution | 1.5M H2SO4 |

Levels of anti-Aβ IgGs were measured using direct ELISA with the test antigen directly coated to the plate and subtracted the binding of the samples' dilutions to blank wells as described (*New Trends in Alzheimer and Parkinson Related Disorders: ADPD*2009, Collection of Selected free Papers from the 9th International Conference on Alzheimer's and Parkinson's Disease AD/PD, Edited by Abraham Fisher & Israel Hanin; and Szabo P. et al., (2010): J Neuroimmunology; doi 10.1016/j.jneuroim.2010.06.010, the contents of which are hereby expressly incorporated herein by reference in their entireties for all purposes, and in particular for all teachings related to ELISA procedures). In particular, Aβ42 monomers, Aβ40 CAPS, and Aβ40 fibrils were used to coat the ELISA plates. ELISAs were performed at both isotonic conditions using PBS and at lower conductivity in 20 mM HEPES buffer, pH 7.2. The coating antigen Aβ42 monomer was diluted to 10 μg/mL with 0.2 m-filtered coating buffer, while CAPS and fibrils were diluted to 2 μg/mL. 100 μL/well of the coating solution were loaded to the upper half (rows A-D) of the 96-well polystyrene microplate (Maxisorp F96) using sterile tips. The lower half of the plate (rows E-H) was loaded with 100 μL/well of coating buffer. The plate was then sealed and incubated at 4° C. overnight. PBST was used as a washing buffer. Washing terminated the coating procedure and was further done between the individual steps. Washed plates were incubated with 200 μL/well 0.2 m-filtered blocking/dilution buffer "hSA" at 37° C. for 1 hour and then washed. The sample dilution series, consisting of six 1+1 dilutions, were then prepared on the plate (100 μL/well) and incubated for 1 h at RT. The dilution series started at about 100-times higher dilutions for the HEPES system, taking into account the higher signals obtained at lower conductivity. After washing, 100 μL/well of anti-human IgG peroxidase (DakoCytomation, 1/2000 in blocking/dilution buffer) was added to the washed plate and incubated at RT for 1 hour, prior to an additional wash. Bound peroxidase was measured by means of Sureblue (100 μL/well) and the color reaction stopped after 15 min at RT by adding 100 μL/well of 1.5 M sulfuric acid. Binding was subsequently measured at 450 nm with the reference wavelength set at 620 nm. Data evaluation was as follows: the averaged optical densities (ODs) of duplicates were corrected by subtracting the mean OD of the respective reagent blank. In the next step, the mean ODs obtained for a particular dilution of the sample on the Aβ42-coated wells were further corrected by subtracting the respective mean ODs measured for the same dilution on blank wells. ODs thus obtained were further used for establishing a concentration-response curve with the IgG concentrations of the dilutions. The final results of the assays were obtained using this linear concentration-response curve and expressed as OD per mg IgG.

The results of the ELISA analysis performed in the PBS buffer system for the eight sample pairs are shown in FIG. 2A. In particular, the mean signals for Aβ40 fibril and non-coated wells are given, measured for the lowest dilution of the dilution series, as well as the ratios between these signals and the ODs per mg IgG to normalize for the different IgG concentrations of the samples. Finally, the table gives the ratios between the IgG-normalized signals of the 2 M wash fractions and the cation exchange eluates, shown in the column "Ratio 2M/E."

As reported in FIG. 2A, the 2M wash fractions showed a higher binding to the plate-immobilized Aβ40 fibrils than the corresponding eluates in all cases, with ratios ranging from 1.4 to 4.2, resulting in a mean ratio of 2.5. Interestingly, the IgG contained in the 2M wash fraction demonstrated, on average, almost two times higher binding to the blank wells. In particular, the two 2 M wash fractions with the highest binding to the blank wells, LE12H254Z and LE12H256Z, were also the wash fractions which showed the lowest increase in Aβ binding, as compared to the corresponding eluate fractions. This suggests that antibodies with different specificities are responsible for this observed binding.

The results of the ELISA analysis performed in the low ionic strength system for the eight sample pairs are shown in FIG. 2B. Again, in all cases, the 2M wash fractions demonstrated higher binding to Aβ40 fibrils than the corresponding eluates, with ratios ranging from 3.3 to 8.0, resulting in a mean ratio of 4.6. Overall, the low ionic strength conditions increased the binding to the Aβ-coated wells, such that lower IgG concentrations could be used in the assays. This decreased the binding to the non-Aβ coated wells for both fractions, which was lower than 4% for both fractions. Interestingly, under these conditions the IgGs of the 2M wash fraction showed lower binding to the blank wells than those contained in the eluate. Overall, the results obtained at both isotonic and low ionic strength demonstrate that the 2 M wash fraction contain higher relative concentrations of antibodies specific for Aβ40 fibril, than the corresponding cation exchange eluates (e.g., the 2 M wash fractions are more enriched for anti-Aβ40 fibril antibodies). Interestingly, this difference is more pronounced under the conditions of low ionic strength. The Aβ40 fibril ELISA data are summarized in FIG. 3, which directly compares normalized ODs observed for the 2 M wash fractions and cation exchange eluates.

Binding of the 2 M wash fractions and corresponding cation exchange eluates to Aβ40 CAPS was next investigated. FIG. 4 shows the data obtained from measurements of the eight sample pairs using the PBS buffer system. Specifically, the mean signals from the CAPS coated and blank wells are given, measured for the lowest dilution of the dilution series. The ratios between these signals and the ODs per mg IgG are also reported, which are normalized for the IgG concentrations of the samples. Finally, the table gives the ratios between the IgG-normalized signals of the 2 M wash fractions and corresponding cation exchange eluates.

As reported in FIG. 4A, under isotonic buffer conditions, the 2 M wash fractions had higher binding to the Aβ40 CAPS than the corresponding cation exchange eluates in all cases, with ratios (2M/E) ranging from 1.8 to 2.9, resulting in a mean ratio of 2.1. The 2 M wash fraction also displayed greater binding to the blank wells than the corresponding eluates.

Figures 5A, 5B:
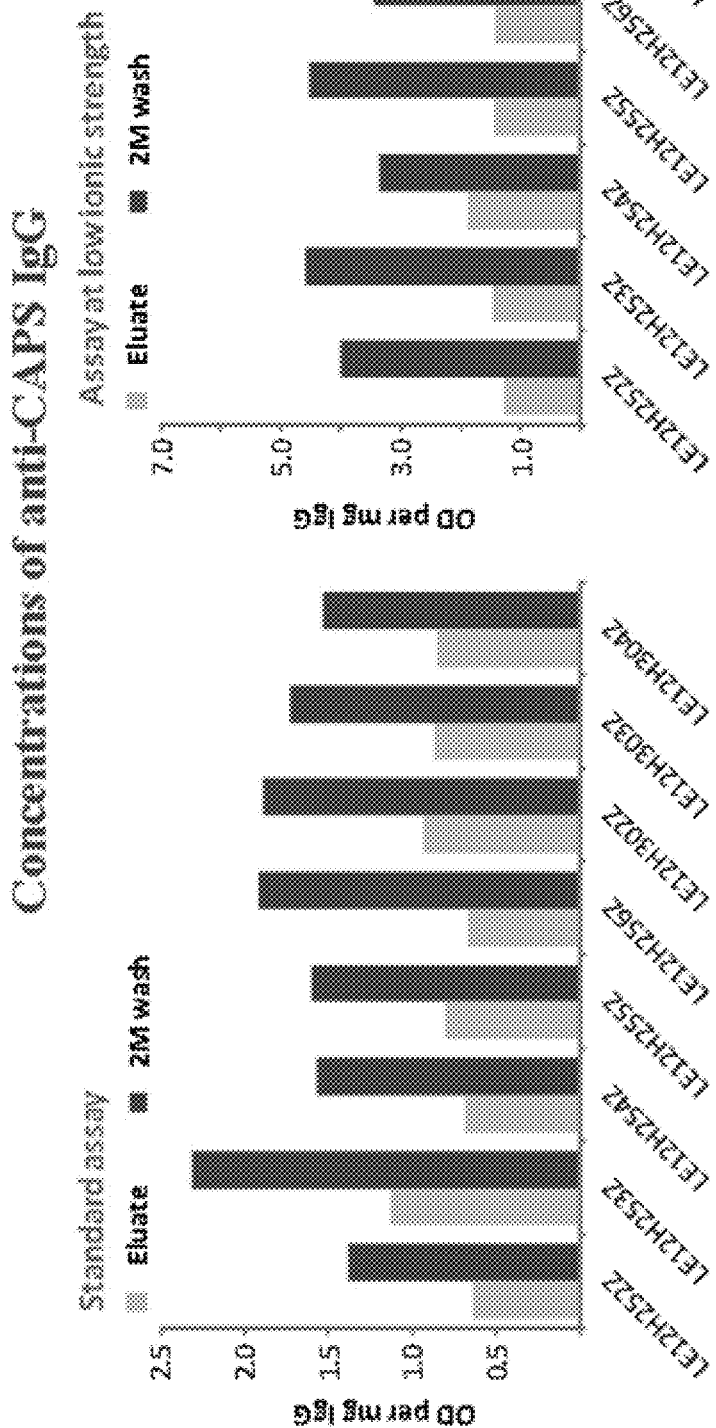
FIG. 5A-5B illustrate the relative concentrations of anti-Aβ40 CAPS IgG antibodies in matching samples of the cation exchange eluate and corresponding 2 M wash fraction generated during preparation of a plasma-derived IgG composition, as determined under isotonic (FIG. 5A) or low ionic strength (FIG. 5B) conditions.

The results of the ELISA analysis performed in the low ionic strength buffer system for the eight sample pairs are shown in FIG. 4B. Again, the 2 M wash fractions demonstrated higher binding to the Aβ40 CAPS than the corresponding eluates, with ratios ranging from 1.8 to 4.4, resulting in a mean ratio of 3.1. Overall, using the low conductivity buffer system, binding of IgG to the plate-bound CAPS was enhanced, whereas binding to blank wells was reduced, making up less than 4% of the total measured signal when the assay was done at low conductivity. Interestingly, the difference in binding to the Aβ40 CAPS between the 2 M wash and eluate fractions was more pronounced under low strength conditions. Overall, the results obtained at both isotonic and low ionic strength demonstrate that the 2 M wash fraction contain higher relative concentrations of antibodies specific for Aβ40 CAPS, than the corresponding cation exchange eluates (e.g., the 2 M wash fractions are more enriched for anti-Aβ40 CAPS antibodies). As seen for the Aβ40 fibril ELISAs, the signals generated using the low ionic strength buffer system, using 100-fold higher dilutions, evidence the higher binding obtained with the low ionic strength ELISA buffer system. The Aβ40 CAPS ELISA data are summarized in FIG. 5, which directly compares normalized ODs observed for the 2 M wash fractions and cation exchange eluates.

Finally, Binding of the 2 M wash fractions and corresponding cation exchange eluates to Aβ42 monomers was investigated. FIG. 6 presents the data obtained from ELISA assays of the eight sample pairs using the PBS and low ionic strength buffer systems. Specifically, the mean signals from the Aβ42 monomer-coated and blank wells are given, measured for the lowest dilution of the dilution series. The ratios between these signals and the ODs per mg IgG are also reported, which are normalized for the IgG concentrations of the samples. Finally, the table gives the ratios between the IgG-normalized signals of the 2 M wash fractions and corresponding cation exchange eluates.

As reported in FIG. 6A, under isotonic buffer conditions, the 2 M wash fractions had higher binding to the Aβ42 monomers than the corresponding cation exchange eluates, with ratios (2M/E) ranging from 0.9 to 3.0, resulting in a mean ratio of 1.7. The 2 M wash fraction also displayed greater binding to the blank wells than the corresponding eluates.

Figure 7A:
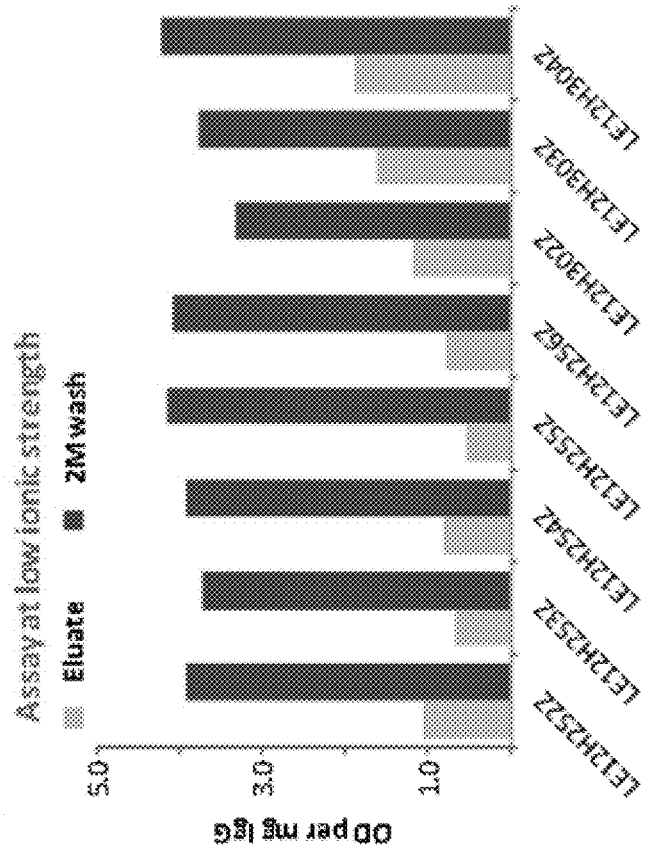
FIG. 7A-7B illustrate the relative concentrations of anti-Aβ42 monomer IgG antibodies in matching samples of the cation exchange eluate and corresponding 2 M wash fraction generated during preparation of a plasma-derived IgG composition, as determined under isotonic (FIG. 7A) or low ionic strength (FIG. 7B) conditions.
Figure 7B:
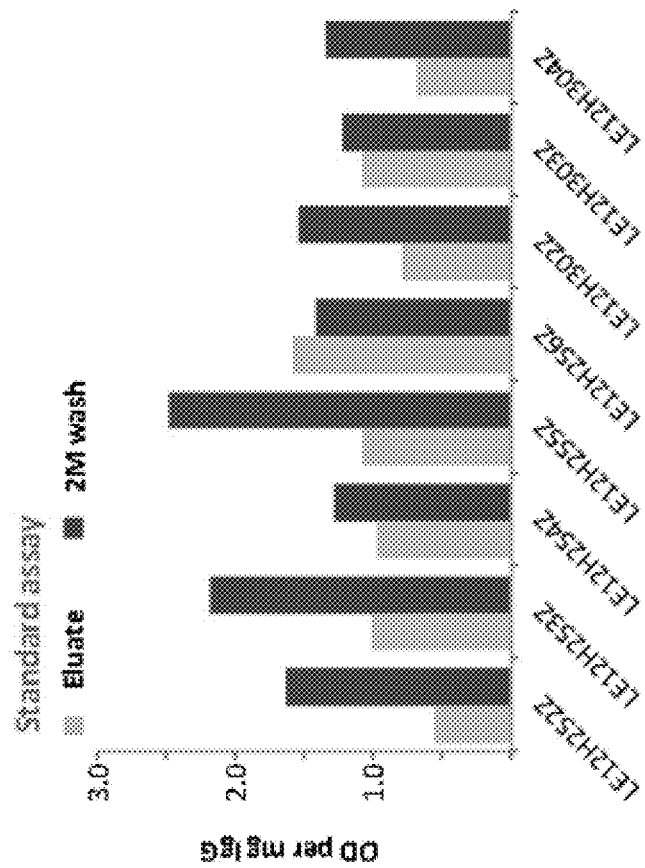

The results of the ELISA analysis performed in the low ionic strength buffer system for the eight sample pairs are shown in FIG. 6B. Again, the 2 M wash fractions demonstrated higher binding to the Aβ42 monomers than the corresponding eluates, with ratios ranging from 2.3 to 7.8, resulting in a mean ratio of 3.7. Overall, using the low conductivity buffer system, binding of IgG to the plate-bound Aβ42 monomers was enhanced, whereas binding to blank wells was reduced, making up no more than 9% of the total measured signal when the assay was done at low conductivity. Again, the difference in binding to the Aβ42 monomers between the 2 M wash and eluate fractions was more pronounced under low strength conditions. Overall, the results obtained at both isotonic and low ionic strength demonstrate that the 2 M wash fraction contain higher relative concentrations of antibodies specific for Aβ42 monomers, than the corresponding cation exchange eluates (e.g., the 2 M wash fractions are more enriched for anti-Aβ42 monomers antibodies). As seen for the Aβ40 fibril and CAPS ELISAs, the signals generated using the low ionic strength buffer system, using 100-fold higher dilutions, evidence the higher binding obtained with the low ionic strength ELISA buffer system. The Aβ42 monomer ELISA data are summarized in FIG. 7, which directly compares normalized ODs observed for the 2 M wash fractions and cation exchange eluates.

FIG. 8 summarizes all the ELISA data collected for anti-Aβ antibody binding in the cation exchange 2 M wash and eluate fractions. The 2M wash fractions showed greater binding to all conformers of Aβ peptide tested than did the eluate fractions, evidencing higher relative contents of anti-Aβ antibodies in the wash fraction. On average, under isotonic conditions, the 2M wash fraction contained 1.7, 2.1 and 2.5-fold higher binding to Aβ42 monomer, Aβ40 CAPS, and Aβ42 fibrils, respectively, than the corresponding eluate (FIG. 8A). These findings were corroborated by the results obtained at low conductivity (e.g., sub-isotonic conditions), where the difference in binding affinity was more pronounced. Under sub-isotonic conditions, the 2M wash fraction contained 3.7, 3.1 and 4.6-fold higher binding to Aβ42 monomer, Aβ40 CAPS, and Aβ42 fibrils, respectively, than the corresponding eluate (FIG. 8B).

In summary, the ELISA data demonstrates that the 2M wash fraction of the CM cation exchange chromatography step contains enriched levels of anti-amyloidogenic IgG, when compared head-to-head with the corresponding eluate fractions. The enrichment of Aβ binding in the 2 M wash fraction is even more pronounced when low ionic strength assay conditions are used for the ELISAs.

Example 3—IgG Subclass Analysis of Antibodies in the Eluate and High Salt Wash Fractions Formed During Cation Exchange Chromatography The same eight pairs of cation exchange eluates and corresponding 2 M wash fractions formed during large scale preparation of a plasma-derived IgG composition described in Example 2 were used in the IgG subclass analysis described below.

Figures 9A, 9B:
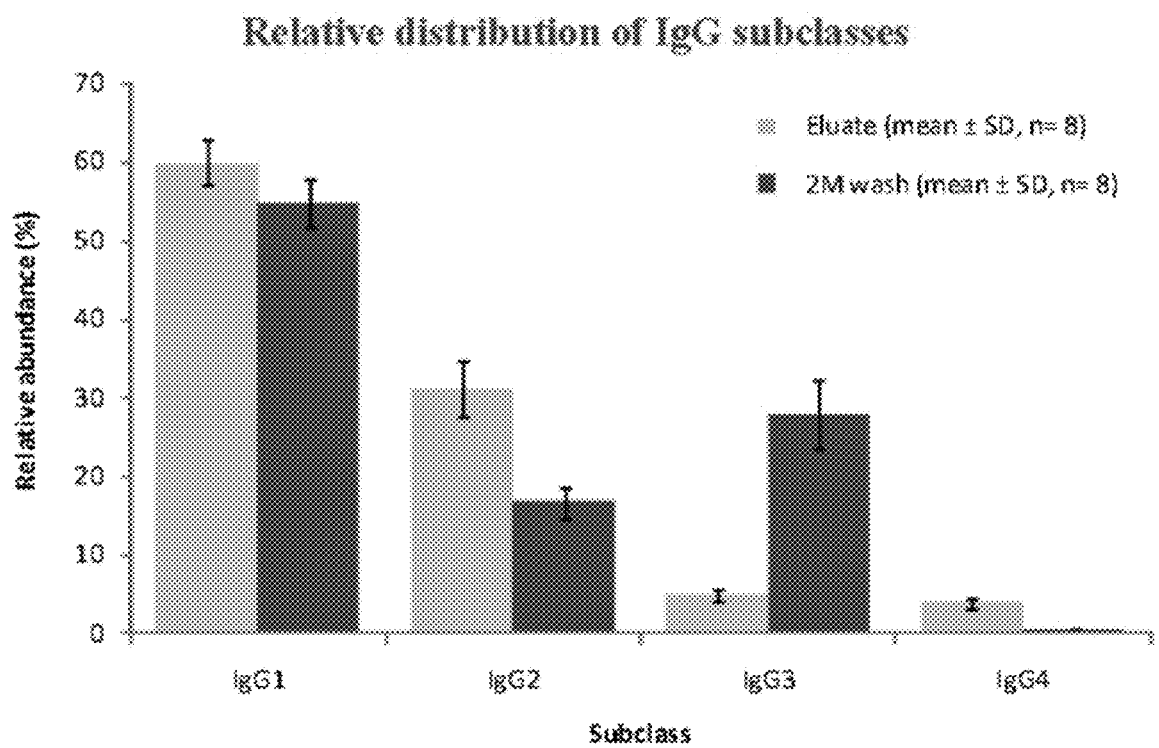
FIG. 9A-9B provide the results of IgG subclass analysis of matching samples of the cation exchange eluate and corresponding 2 M wash fraction generated during preparation of a plasma-derived IgG composition.

The proportion of IgG subclasses in the 2 M wash and eluate fractions were measured by ELISA against human IgG subclass-specific capture and detection antibodies (The Binding Site). Assays were calibrated according to the published IgG subclass concentrations of the international reference preparation CRM470 (Schauer U. et al., (2003): Clin Chem 49(11), 1924-1929). FIG. 9A shows the data collected for each of the eight sample pairs of eluates and corresponding 2 M wash fractions. These data are reported as a percent of the total IgG, which was determined as the sum of the four subclass measurements.

The subclass distribution of the IgG in the 2M wash fraction differed markedly from that determined for the eluate fraction, as summarized in FIG. 9B. Most striking, the 2 M wash fractions have almost 6-fold higher relative contents of $IgG_3$ than the corresponding eluate fractions. Accordingly, the relative $IgG_2$ and $IgG_4$ concentrations were reduced in the 2 M wash fractions, while the relative $IgG_1$ concentration was the same in the 2 M wash and eluate fractions.

Figures 10A, 10B, 10C:
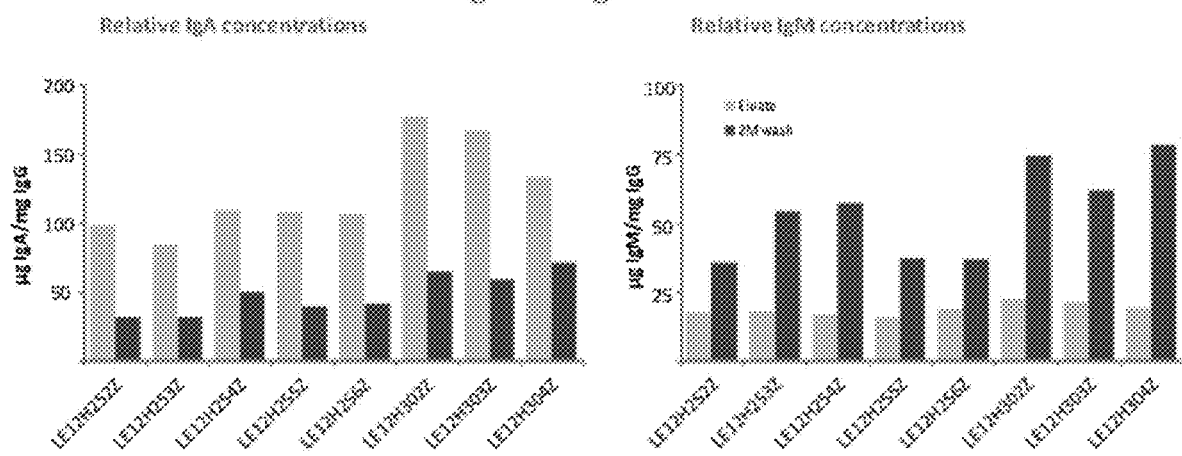
FIG. 10A-10C provide the results of IgA and IgM analysis of matching samples of the cation exchange eluate and corresponding 2 M wash fraction generated during preparation of a plasma-derived IgG composition.

Example 4—Analysis of IgA and IgM Contents in the Eluate and High Salt Wash Fractions Formed During Cation Exchange Chromatography Because carboxymethyl (CM) cation exchange chromatography was the first downstream enrichment step used for the preparation of the plasma-derived IgG composition (outlined in FIG. 1), it was speculated that the 2 M wash and eluate fractions may have different relative concentrations of IgA and IgM. To investigate this possibility, ELISA assays specific for human IgA and IgM antibodies were performed. FIG. 10A reports the results of these assays, showing concentrations of IgA and IgM in each of the eight pairs of cation exchange eluate and the 2 M wash fractions described above. Concentrations are reported as absolute (μg/mL) and as normalized to the corresponding IgG concentration of the sample (g IgA or IgM per mg IgG). The difference in IgA and IgM content for each matching sample is illustrated in FIGS. 10B and 10C, respectively.

As seen in FIG. 10, the cation exchange eluate and 2 M wash fractions had different IgA and IgM concentrations. Interestingly, the relative IgA concentrations in the eluate fractions were, on average, 2.5-fold higher than in the corresponding 2 M wash fractions, while the opposite was found for the IgM content, where were found to be, on average, 2.9-fold higher in the 2 M wash fractions than in the corresponding eluates. In absolute terms, the eluates contained lower levels of IgM than IgA, while the 2 M wash fractions had similar levels of both types of immunoglobulins. These data help explain the differences in the molecular size distribution profiles observed for the eluate and 2 M wash fractions, reported below.

Figures 11A, 11B:
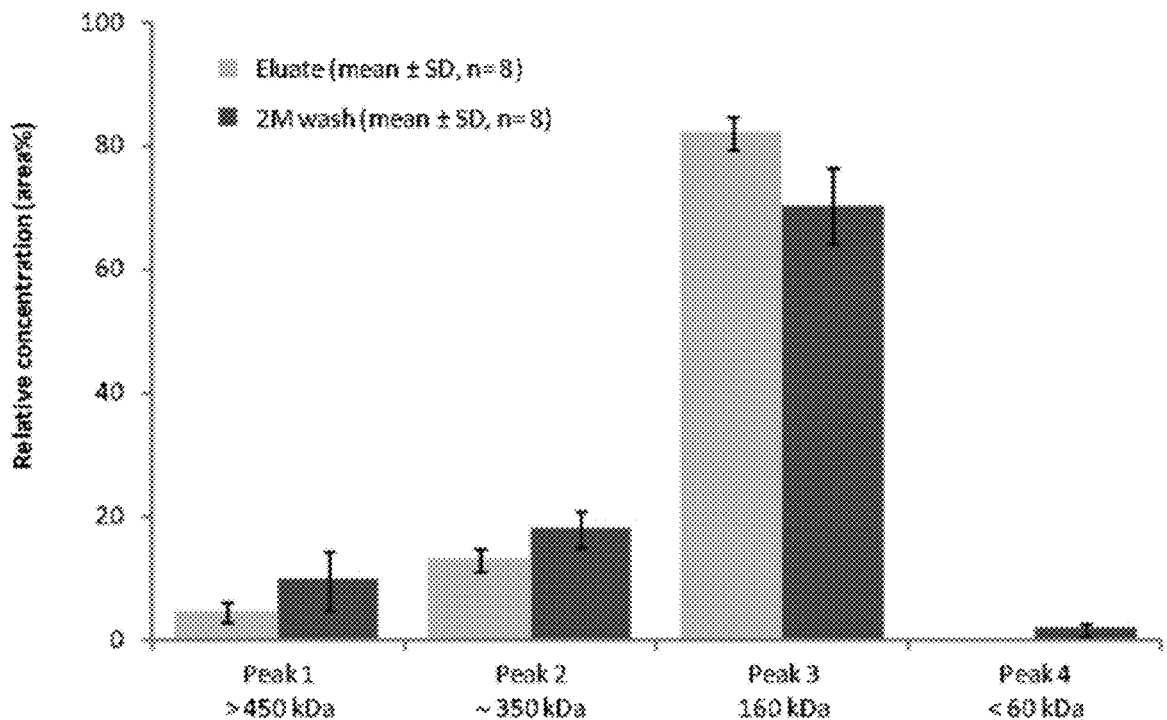
FIG. 11A-11B provide the results of HP-SEC analysis of the size distribution of protein in matching samples of the cation exchange eluate and corresponding 2 M wash fraction generated during preparation of a plasma-derived IgG composition.

Example 5—HP-SEC Analysis of the Molecular Weight Profiles of Eluate and High Salt Wash Fractions Formed During Cation Exchange Chromatography HP-SEC performed using hydrophilic silica columns is the established method of choice for analysis of the molecular size distribution profile of immunoglobulin compositions. Here, one should have in mind that: (i) this analysis was performed on intermediate fractions, rather than a final product; and (ii) the 2 M wash and corresponding wash fractions differed in their IgA and IgM concentrations. While the first point to consider explains the unusual high relative levels of aggregates, measured for both fractions, the second point help to explain the differences with respect to relative concentrations of aggregates observed in both fractions. FIG. 11A illustrates the mean relative concentrations of the four peaks separated on HP-SEC for the eluate and 2 M wash fractions. The raw numerical data are for each sample are reported in FIG. 11B.

As illustrated in FIG. 11A, the mean relative aggregate concentration of the 2M wash fractions was 2-fold higher than for the eluate fractions. However, as can be seen in FIG. 11B, this difference is mostly caused by three particular lots (LE12H302Z, LE12H303Z and LE12H304Z) which each had relative aggregate concentrations of greater than 10%. These lots also had the highest relative IgM concentrations, accounting for at least a portion of the elevated levels of aggregation. The higher relative concentration of dimer observed in each individual 2 M wash fraction, as compared to the corresponding eluate fraction, can be explained at least in part by the higher relative concentrations of $IgG_3$ subclass found in the 2 M wash fraction, as this IgG subtype elutes later in SEC analysis due to of its elongated hinge region.

Figures 12A, 12B:
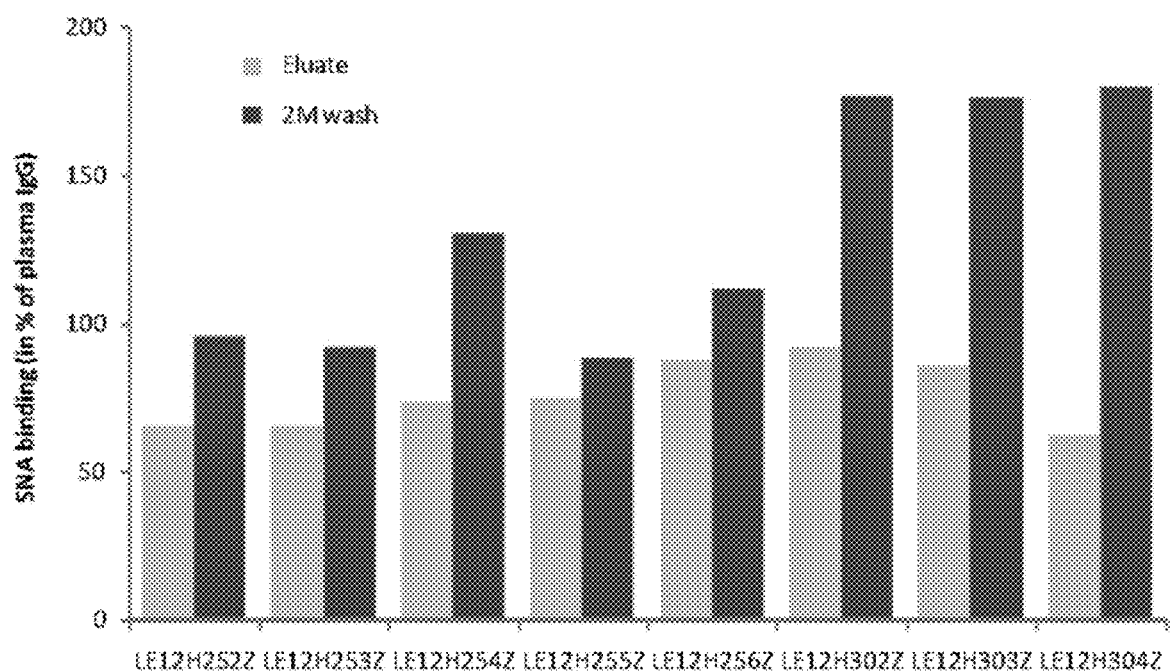
FIG. 12A-12B report data obtained (FIG. 12A) from anti-SNA lectin ELISAs performed with matching samples of the cation exchange eluate and corresponding 2 M wash fraction generated during preparation of a plasma-derived IgG composition, and illustrates (FIG. 12B) relative IgG binding to SNA lectin as a percentage of control plasma IgG binding for each of the matching samples.

Example 6—Lectin Binding Analysis of IgG Present in Eluate and High Salt Wash Fractions Formed During Cation Exchange Chromatography Lectins are useful tools for investigating complex carbohydrates, as they bind with high selectivity recognizing in most cases not only single mono- or oligosaccharides but also linkages. SNA is an example for such a selective lectin as it strictly binds only to sialic acid when present in an α2,6-linkage to galactose (Stadlmann J et al. (2009): Proteomics 9, 1-11). In contrast to other plasma glycoproteins, where the N-glycans and especially the terminal sialic acids are easily accessible, the two Fc N-glycans of IgG are known to be shielded by the protein backbone of the CH2 domain. This specific alignment of the Fc N-glycans causes steric hindrance preventing every α2,6-bound sialic acid on the IgG1 Fc from being able to bind to SNA. Thus, $IgG_1$ Fc glyco-variants carrying one sialic acid only on their two N-glycans will not bind to the lectin. Lectin binding assay were performed which selectively measure the α2,6-sialylation of IgG, without introducing bias from the presence of other sialylated glycoproteins, because human IgG is specifically captured on the assay plate. This approach is also used to evaluate SNA binding of IgG based on the measurement of a human reference plasma. The results of the SNA binding assay are reported in FIG. 12A, as a percent of SNA bound in the reference plasma sample. Individual samples were measured in triplicate, and the averages for each of the eight sample pairs described above of the samples are illustrated in FIG. 12B. As seen in FIG. 12, in all cases, the cation exchange 2 M wash fractions have higher relative SNA binding activities than the corresponding eluate fractions. In four of the 2 M wash fraction samples (LS12H254Z, LE12H302Z, LE12H303Z, and LE12H304Z), SNA binding was substantially enriched as compared to the reference plasma sample.

Figure 13:
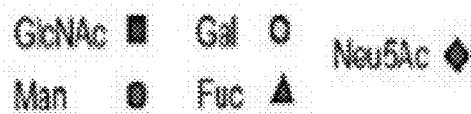
FIG. 13 reports the results of total N-glycan analysis on matching samples of the cation exchange eluate and corresponding 2 M wash fraction generated during preparation of a plasma-derived IgG composition.

Example 7—Total N-Glycan Analysis of IgG Present in Eluate and High Salt Wash Fractions Formed During Cation Exchange Chromatography The data from SNA binding assays, reported in Example 6, warranted further investigation. First, a complete analysis of the N-glycan pattern of IgG present in the sample pairs from lots LE12H252Z, LE12H254Z, and LE12H255Z was performed. The total N-glycan profiles for these samples were obtained after enzymatic release of the N-glycans. This analysis compared the N-glycan profiles independent of whether or not the N-glycan was derived from IgG. This has to be considered when directly comparing the data because the N-glycans of the non-IgG glycoproteins contained in the samples such as IgA and IgM, which are both highly glycosylated, also contributed to these data. The results of this analysis are presented in FIG. 13, which shows the relative abundance of each N-glycan.

As seen in these results, the 2 M wash fractions from lots LE12H254Z and LE12H255Z had higher levels of mono- and disialylated N-glycans, whereas the 2 M wash fraction from the third lot contained lower levels of sialylated N-glycans. This seems to contrast with the results of the SNA binding assay, where all 2 M wash fractions showed a higher binding to the sialic acid-specific lectin, but can be explained by the specificity of the lectin binding assay. As the concentrations of IgA and IgM only differed moderately among the three lots, the presence of other glycoproteins seems to be the most likely reason for these differences.

Example 8—N-Glycan Analysis of $IgG_1$ Fc Present in Eluate and High Salt Wash Fractions Formed During Cation Exchange Chromatography The $IgG_1$ Fc N-glycan content of the respective 2 M wash and eluate fractions of the three sample lots tested in Example 7 was determined by LC-MS analysis of tryptic glycopeptides, which allow unambiguous identification of $IgG_1$ Fc N-glycans based on amino acid sequences. The results of this analysis are provided in FIG. 14, reported as relative percentages of the main N-glycans found on $IgG_1$ Fc regions. The individual results for lots LE12H252Z, LE12H154Z, and LE12H255Z are illustrated in FIGS. 15A-C, respectively.

As shown in FIG. 14, all three 2 M wash fractions showed higher levels of $IgG_1$ Fc sialylation than the corresponding eluate fractions, with rather uniform absolute differences of 3.5%, 4.0%, and 3.4%. This translated to a relative increase of 30% in the sialylation of $IgG_1$ in the 2 M eluate fractions. As seen in FIGS. 15A-15C, all three sample pairs showed a similar distribution of $IgG_1$ Fc N-glycan structures. In all cases, the mono-sialylated biantennary ANaF N-glycan was found at higher levels in the 2 M wash fraction, whereas levels of the second sialylated N-glycan, GnNAF, showed only slight differences. Interestingly, the bi-galactosylated glycan AFF, a biosynthetic precursor of ANaF, which is the substrate for the sialyltransferase, was also found at higher levels in the 2 M wash fractions than in the corresponding eluates. In contrast, the monogalactosylated AGnF glycan was present at lower levels in the 2 M wash fraction than in the corresponding eluates. The data suggest that $IgG_1$ in the 2 M wash fraction is characterized not only by enrichment of sialylation but also by enrichment of galactosylation.

Discussion

Figure 1:
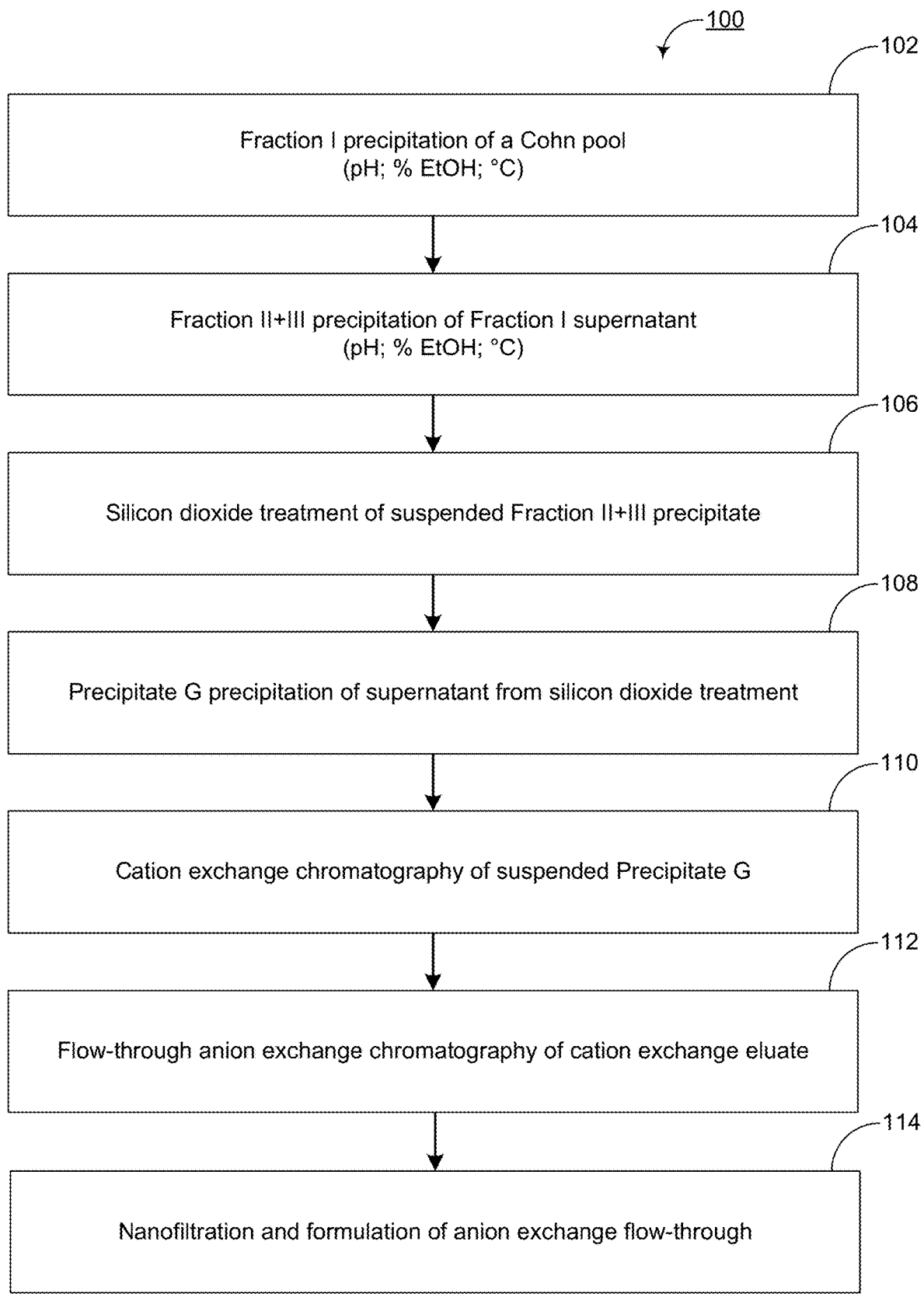
FIG. 1 illustrates an exemplary method for the preparation of a plasma-derived IgG composition.

The biochemical characterization presented in Example 1-Example 8 of the minor IgG fraction found in the 2 M wash fraction generated during regeneration of the CM chromatographic resin used for enrichment of plasma-derived IgG, as outlined in FIG. 1, provides evidence that IgG lost at this step is not merely representative of the IgG composition as a whole. Rather, it was found that IgGs specific for several Aβ peptide substrates are enriched in this wash fraction. In addition, the N-glycosylation pattern of IgGs in the wash fraction varies from the corresponding cation exchange eluate, with higher levels of binding to the α2,6-neuraminic-acid-specific lectin SNA. This difference was confirmed by LC-MS analysis of the $IgG_1$ Fc N-profile, which revealed higher relative concentrations of monosialylated N-glycans in the 2 M wash fractions. The sialylation of human IgG has been associated with its anti-inflammatory activity (Kaneko Y. et al., Science 313, 670-673 (2006); and Anthony R M et al., Science 320, 373-376 (2008), the disclosures of which are hereby expressly incorporated in their entireties for all purposes) although data have been published (Bayry J. et al., PNAS 106(9) (2009), the disclosure of which is hereby expressly incorporated in its entirety for all purposes) suggesting that α2,6-$IgG_1$ Fc sialylation might not be the only mechanism involved in what has been called the anti-inflammatory paradox of IGIV (Nimmerjahn and Ravetch, J. Exp. Med. 204, 11-15 (2007), the disclosure of which is hereby expressly incorporated in its entirety for all purposes).

Nevertheless, these studies demonstrate that the 2 M wash fraction of the IgG enrichment step outlined in FIG. 1 contains higher levels of Fc sialylated IgGs, which allows for the use of this, and similar fractions, for as a starting material for the purification of this IgG subpopulation. This is an attractive possibility that is further encouraged by the finding that this fraction also contains higher levels of anti-Aβ IgGs than the corresponding eluate formed by cation exchange chromatography. The data presented above evidence that the 2 M wash fraction is enriched for binding to all Aβ conformers investigated, especially when the binding assay was performed under low conductivity conditions, where background binding to the wells themselves was reduced to a minimum.

The higher relative levels $IgG_3$ subclass antibodies in the 2 M wash fraction is interesting, because as compared to the other three IgG subclasses, $IgG_3$ has an extended hinge region, rendering this subclass almost unable to bind to the neonatal Fc receptor in the presence of other IgG subclasses, and also rendering it highly susceptible to proteolytic degradation. On the other hand, this extended hinge region could provide additional, as of yet unidentified, structural elements involved in non-Fab-mediated binding to Aβ peptides, and thus establishing a direct correlation between higher binding to Aβ conformers and $IgG_3$ levels. Such a contribution of IgG constant regions to Aβ binding has recently been shown for the human IgG γ-heavy chain (Adekar S P et al., Biol. Chem. 285, 1066-1074 (2009)).

Significantly, the data provided above provide an explanation as to why, up to now, it was not possible to maintain enriched anti-Aβ42 titers during the manufacture of large-scale plasma-derived immunoglobulin preparations, although starting materials having 4-fold greater titer, as compared to averages for pooled human plasma were used as starting materials. The results obtained here evidence that anti-Aβ IgGs can be lost at the CM chromatographic enrichment step of common manufacturing processes.

Example 9—Purification of IgG Compositions from High Salt Wash Fractions Formed During Cation Exchange Enrichment of Plasma-Derived IgG Given the unexpected properties of the high salt wash fraction identified in the examples above, it was investigated whether an immunoglobulin composition suitable for pharmaceutical use could be prepared from this side fraction. As described in detail below, IgG from five samples of the 2 M sodium chloride wash formed during regeneration of the cation exchange resin used for enrichment of plasma-derived IgG as outlined in FIG. 1 (CHR435, CHR446, CHR456, CHR457, and CHR460), was enriched to a final composition. Biochemical analysis of these five compositions revealed that they met or nearly met each of the impurity specifications for plasma-derived IVIG compositions. Remarkably, the final compositions had anti-RAGE, anti-α-synuclein, and anti-Aβ titers that were about 20-fold, 50-fold, and 80-fold higher than the average titers in IVIG compositions prepared by the method outlined in FIG. 1, respectively. On average, the final yield of the anti-brain disease-related protein immunoglobulin compositions was 0.06 g per L starting plasma.

Figure 16:
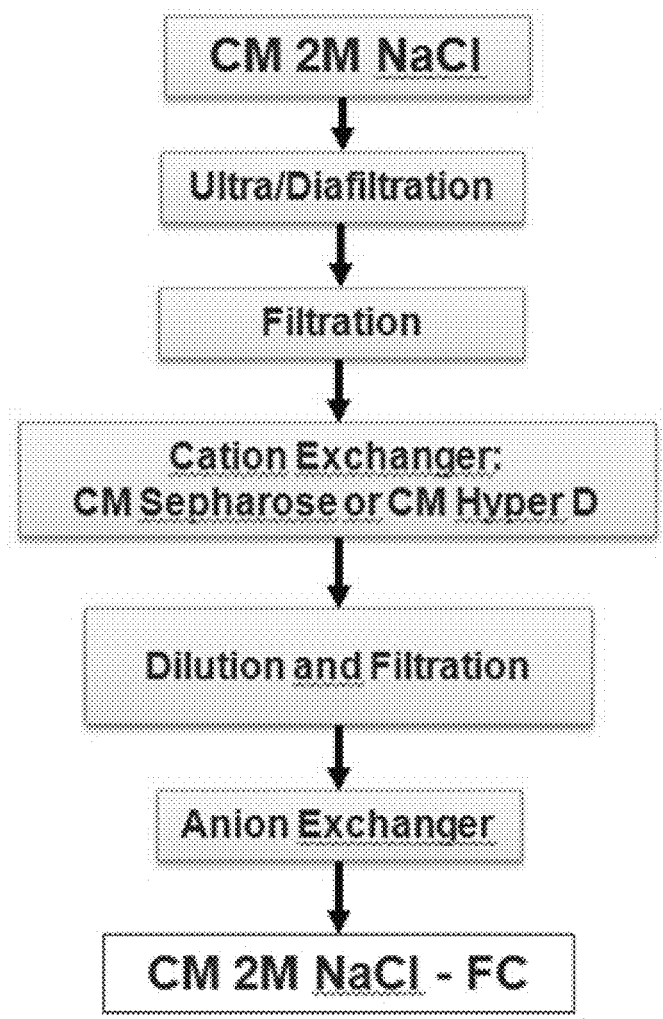
FIG. 16 illustrates an exemplary method for the preparation of a plasma-derived IgG compositions enriched in anti-brain disease-related protein IgG antibodies.

The five samples described above, each equivalent to 750 L of plasma starting material, were enriched according to the method outlined in FIG. 16. Briefly, the 2 M wash fractions were concentrated by ultrafiltration to a target concentration of 1% protein (e.g., 10 mg/mL). The concentrated solution was then diafiltered against water to reduce the conductivity to a target of 6 mS/cm for CM Sepharose chromatography and 11 mS/cm for CM HyperD chromatography, and then concentrated by ultrafiltration to a final concentration of 2% protein. The concentrated solution was then filtered and loaded onto either a CM Sepharose or CM HyperD® (Pall Corporation) cation exchange column.

For IgG binding to CM Sepharose, the column was equilibrated with buffer containing 10 mM sodium acetate (about 0.85 mS/cm; pH 5.2) prior to loading. After loading, the column was washed with buffer containing 10 mM sodium acetate (about 0.85 mS/cm; pH 5.5). The immunoglobulins were then eluted off of the CM Sepharose cation exchange resin with an elution buffer containing 100 mM monosodium phosphate, 10 mM Tris (about 13 mS/cm; pH 8.5).

For IgG binding to CM HyperD, the column was equilibrated with buffer containing 10 mM sodium acetate (about 2 mS/cm; pH 5.2) prior to loading. After loading, the column was washed with buffer containing 10 mM sodium acetate (about 2 mS/cm; pH 5.5). The immunoglobulins were then eluted off of the CM HyperD cation exchange resin with an elution buffer containing 100 mM monosodium phosphate, 10 mM Tris (about 13 mS/cm; pH 8.5).

The cation exchange eluates were then diluted to reduce the solution conductivity to 2.2 mS/cm and adjust the pH to 6.4. The diluted samples were then applied to an anion exchange column equilibrated with buffer having a conductivity of 2.2 mS/cm. The flow through from the anion exchange resin was collected. This flow through was then concentrated to a target concentration of 5% by ultrafiltration, diafiltered against 0.25 M glycine pH 4.2, and concentrated to a final target protein concentration of 10.2% by ultrafiltration. The ultrafiltrate was sterile filtered and then incubated at 30° C. for three weeks As shown in Table 3, analysis of the IgG compositions enriched from the 2 M cation exchange wash fraction demonstrate greater than 80% recovery of IgG in the four purifications using CM HyperD cation exchange resin, and about 79% recovery with CM Sepharose resin. Biochemical analysis also show low level of impurities (e.g., IgA, IgM, fibrinogen, and transferrin), all of which are within the specification for plasma-derived IVIG manufacturing. Size distribution shows that the compositions purified with CM HyperD have greater than 99.5% monomeric IgG, while the composition purified with CM Sepharose contains 97.5% monomeric IgG and 2.5% fragmented IgG.

The final compositions were also tested for markers of potential pro-coagulant activities. As shown in Table 4, the IgG compositions prepared using CM HyperD contained very low levels of all markers tested.

TABLE 3

Protein analysis and impurities in final IgG compositions prepared from the 2M sodium chloride wash fraction formed in the method outlined in FIG. 1.

| Parameter | Unit | Bulk CM Sepharose CHR435 | Bulk CM Hyper D CHR446 | Bulk CM Hyper D CHR456 | Bulk CM Hyper D CHR457 | Bulk CM Hyper D CHR460 | Specifications IVIG Manufacturing |
|---|---|---|---|---|---|---|---|
| Protein Recovery | % of 2M NaCl | 78.9 | 68.0 | 70.1 | 75.1 | 64.8 | — |
| IgG (ELISA) Recovery | % of 2M NaCl | 78.8 | 88.0 | 81.2 | 92.6 | 83.5 | — |
| IgA (ELISA) | mg/mL (at 10% TPUV) | 0.021 | 0.015 | 0.021 | 0.022 | 0.025 | ≤0.14 |
| IgM (ELISA) | mg/mL (at 10% TPUV) | 0.0013 | 0.0017 | 0.0011 | 0.0027 | 0.0016 | — |
| Fibrinogen | mg/mL (at 10% TPUV) | 0.00035 | <0.00014 | <0.00016 | 0.00097 | <0.00028 | — |
| Transferrin | mg/mL (at 10% TPUV) | 0.0011 | 0.00118 | 0.00111 | 0.00105 | 0.00105 | — |
| MSD VIE | Aggregates (>450 kDa) [%] | 0.04 | 0.07 | 0.05 | 0.08 | 0.03 | ≤2 |
| Monomer/Dimers | (160-320 kDa) [%] | 97.5 | 99.8 | 99.79 | 99.8 | 99.65 | 95 |
|  | Fragments (<60 kDa) [%] | 2.5 | 0.13 | 0.16 | 0.11 | 0.31 | ≤3 |
| CZE (FC) | % γ-globulin | 98 | 100 | 100 | 100 | 100 | ≥98 |
| ACA | % | 57 | 43 | 44 | 45 | 53 | <50 |

TABLE 4

Biochemical analysis of markers for potential pro-coagulant activities in final IgG compositions prepared from the 2M sodium chloride wash fraction formed in the method outlined in FIG. 1.

| Parameter | Unit | FC CM Sepharose CHR435 | FC CM Hyper D CHR446 | FC CM Hyper D CHR456 | FC CM Hyper D CHR457 | FC CM Hyper D CHR460 | Spec.*/Mean/ Range IVIG manufacturing |
|---|---|---|---|---|---|---|---|
| Amidolytic Activity | nmol/mL min | <10 | <10 | <10 | <10 | <10 | <10 |
| FXI zymogen | mU/ml | 0.18 | <0.01 | <0.01 | 0.02 | <0.01 | — |
| FXIa | ng/ml | 2.51 | <0.2 | <0.5 | <0.5 | <0.5 | — |
| NAPTT (FXI Plasma) | mg | >10.2 | >11.4 | >10 | >9.4 | >10.4 | — |

TABLE 4-continued

Biochemical analysis of markers for potential pro-coagulant activities in final IgG compositions prepared from the 2M sodium chloride wash fraction formed in the method outlined in FIG. 1.

| Parameter | Unit | FC CM Sepharose CHR435 | FC CM Hyper D CHR446 | FC CM Hyper D CHR456 | FC CM Hyper D CHR457 | FC CM Hyper D CHR460 | Spec.*/Mean/ Range IVIG manufacturing |
|---|---|---|---|---|---|---|---|
| PKA | IE/ml | <4 | <4 | <4 | <4 | <4 | <10* |
| SN13 a | mU/ml FXI like axtivity | 6.3 | <0.39 | <0.39 | <0.39 | <0.39 (Bulk) | — |
| TGA | % NP | 137.1 | 118.8 | 120.9 | 124.1 | 115.1 | 132.2 |

The titer of specific antibodies was next determined in the composition prepared using CM Sepharose cation exchange resin (CHR435) and one of the compositions prepared using CM HyperD cation exchange resin (CHR460). As shown in Table 5, the content of all specific antibodies tested satisfied the specification requirements for IVIG manufacturing. The content of several anti-brain disease related protein antibodies were determined relative to average levels in large scale IVIG compositions prepared according to the method outlined in FIG. 1. Significantly, the level of anti-RAGE, anti-α synuclein, and anti-Aβ antibodies in the final compositions were about 20-fold, 50-fold, and 80-fold higher, as compared to levels in the large scale IVIG compositions prepared according to the method outlined in FIG. 1. The content of anti-Aβ antibodies specific for different Aβ forms (e.g., fibrils, oligomers, Aβ40, and Aβ42) for the two compositions tested is shown in Table 6, as a ratio of content compared to the mean content of 3 lots of a commercial IVIG preparation. The content of additional antibodies in the high salt CM wash fraction compositions is shown in Table 7.

TABLE 5

Titers of several antibodies normally tested in pooled human IgG compositions, in the final IgG compositions prepared from the 2M sodium chloride wash fraction formed in the method outlined in FIG. 1.

| Parameter | Unit | FC CM Sepharose CHR435 | FC CM Hyper D CHR460 | Spec.*/Mean/ Range IVIG Manufacturing |
|---|---|---|---|---|
| Anti-A Antibody | Titer | 1:2 | 1:4 | 1:<64* |
| Anti-B Antibody | Titer | 1:2 | 1:2 | 1:<64* |
| Anti-D Antibody | — | Satisfying | Satisfying | Satisfying* |
| HBs Antibody | IU/ml | 6.38 | 9.94 | ≥0.20* IU/ml |
| Diphteriae Antibody | U/ml of US Standard | 14 | 11 | ≥1.2* U of US Standard Antitoxin/ml |
| Polio | Quot. gg. Lot 176 | n.a. | 0.29 | ≥0.20* Quot. gg. Lot 176 |
| Tetanus antitoxin | IU/ml | n.a. | 160.9 | |
| CMV | PEI U/ml | n.a. | 218 | |
| HAV | IU/ml | n.a. | 11.5 | |
| Parvo B19 | IU/ml | n.a. | 1935 | |

TABLE 6

Levels of anti-Aβ antibodies in the final IgG compositions prepared from the 2M sodium chloride wash fraction formed in the method outlined in FIG. 1.

| Anti-β Amyloid | CHR435 CM Sepharose ff | | CHR460 CM Hyper D | |
|---|---|---|---|---|
| | OD/μg | Ratio to IVIG | OD/μg | Ratio to IVIG |
| Fibrills | 2.9 | 81 | 2.6 | 74 |
| Oligomers | 5.7 | 87 | 5.6 | 85 |
| Aβ40 | 4.1 | 75 | 3.7 | 66 |
| Aβ42 | 7.4 | 96 | 5.8 | 76 |

TABLE 7

Levels of sialylation, auto-antibodies, and brain disease-related antibodies in the final IgG compositions prepared from the 2M sodium chloride wash fraction formed in the method outlined in FIG. 1.

| | Unit | FC CM Sepharose ff | FC CM Ceramic Hyper D 4 | Range/ Mean of 3 Commercial IVIG lots |
|---|---|---|---|---|
| IgG-SNA | % plasma | 80.1 | 80.5 | 65.2-94.8 |
| Anti-DNA IgG | ratio to IVIG | 3.0 | 3.2 | — |
| Anti-tubulin IgG | ratio to IVIG | 2.0 | 2.1 | — |
| Anti-rHuPH20 IgG | μg/ml | <6.5 | 11.2 | 10.3 |
| Anti-RAGE IgG | ratio to IVIG | 4.5 | 22.4 | — |
| Anti-α synuclein IgG | ratio to IVIG | 53.1 | 51.2 | — |

The IgG subclasses in one of the final compositions were separated, using Capture Select IgG 4 and Mab Select SuRe. Analysis of the subclass fractions is presented in Table 8. Further analysis of the subclass compositions revealed that anti-RAGE antibodies are enriched in the $IgG_1$ and $IgG_4$ subclasses, and that anti-Aβ antibodies are enriched in the $IgG_3$ and $IgG_1$ subclass fractions.

TABLE 8

Analysis of IgG subclass content in a final IgG composition prepared from the 2M sodium chloride wash fraction formed in the method outlined in FIG. 1.

| | IgG Subclasses | | | |
|---|---|---|---|---|
| | IgG 1 | IgG 2 | IgG 3 | IgG 4 |
| FC starting material | 58% | 16% | 25.5% | 0.5% |
| FC IgG 4 | <7% | 55% | <6% | 32% |
| FC D | <0.6% | <0.4% | 97% | 2% |
| FC E2 | 19% | 71% | 10% | <0.2% |
| FC E3 | 96% | 23% | 0.7% | 0.3% |

Complement protein C3 and Factor I contents of the FC CM Sepharose CHR435 and FC CM Hyper D CHR460 final compositions were determined. As shown in Table 9, the levels of both of these proteins are lower in the high salt CM wash fraction preparations than in a commercial IVIG preparation.

TABLE 9

Complement C3 and Factor I contents in final IgG composition prepared from the 2M sodium chloride wash fraction formed in the method outlined in FIG. 1.

|  | Unit | FC CM Sepharose ff | FC CM Ceramic Hyper D 4 | Commercial IVIG |
|---|---|---|---|---|
| Complement C3 | g/L | 0.00036 | <0.00031 | 0.0012 |
| Factor I | g/L | 0.00535 | 0.00250 | 0.025 |

Figure 20:
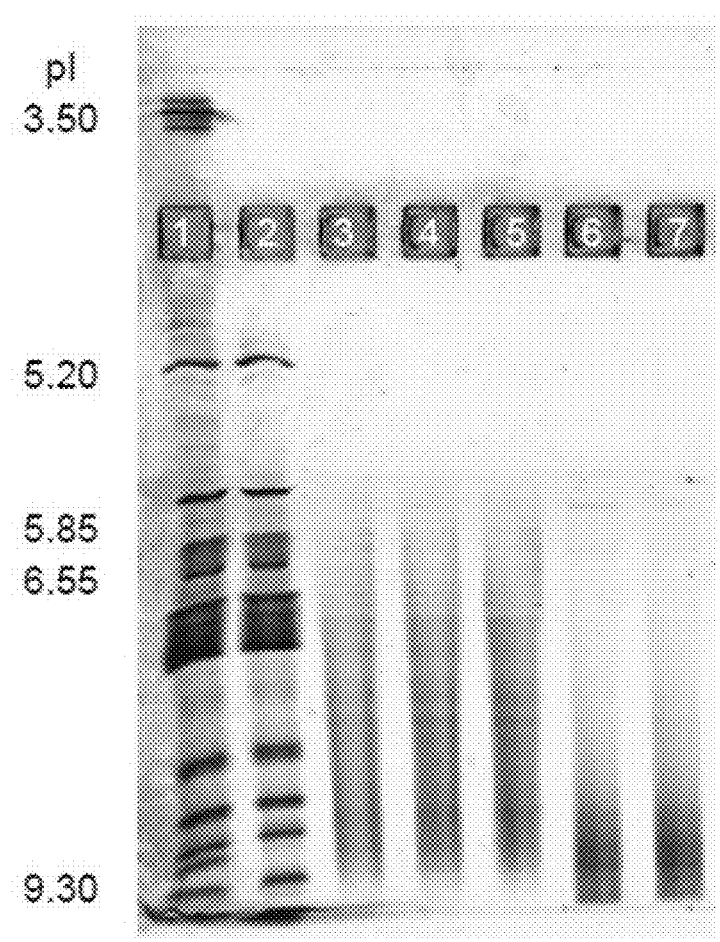
FIG. 20 shows the results of isoelectrical focusing analysis of commercial IVIG lots (lanes 3-5), IgG prepared from CM high salt wash fraction using CM Sepharose ff chromatography (lane 6), and IgG prepared from CM high salt wash fraction using CM Ceramic Hyper D4 chromatography (lane 6). Broad range and high range markers are shown in lanes 1 and 2, respectively.

The isoelectric focusing pattern of the high salt CM wash fraction preparations is different than that of commercial IVIG preparations. Isoelectric focusing analysis was performed for the FC CM Sepharose CHR435 and FC CM Hyper D CHR460 final compositions and compared to three lots of a commercial IVIG product. As shown in FIG. 20, the commercial IVIG lots (lanes 3-5) showed a pI range from 5.7 to 9.3. In contrast, the pI ranges of the final compositions produced from the high salt CM wash fractions (lane 6: FC CM Sepharose ff, lane 7: FC CM Ceramic Hyper D 4) were shifted to higher pI ranges. The IgG population in the high salt CM wash fraction preparations consisted mostly of proteins having pIs between pH 8.5 and 9.5. Only weak signals, between pI 8.5 and 7 and below a pI of 6.55, were visible on the gel.

The pI shift to higher values is explained, at least in part, by the production method employed. The starting IgG population in the high salt CM wash fraction is the portion of the total IgG content that does not elute from the cation exchange resin under conventional elution conditions. One explanation for stronger binding affinity to cation exchange resin is a higher pI value. Thus, it is not unexpected that this particular fraction contains IgG molecules having a higher average distribution of pI values.

Figures 21A, 21B:
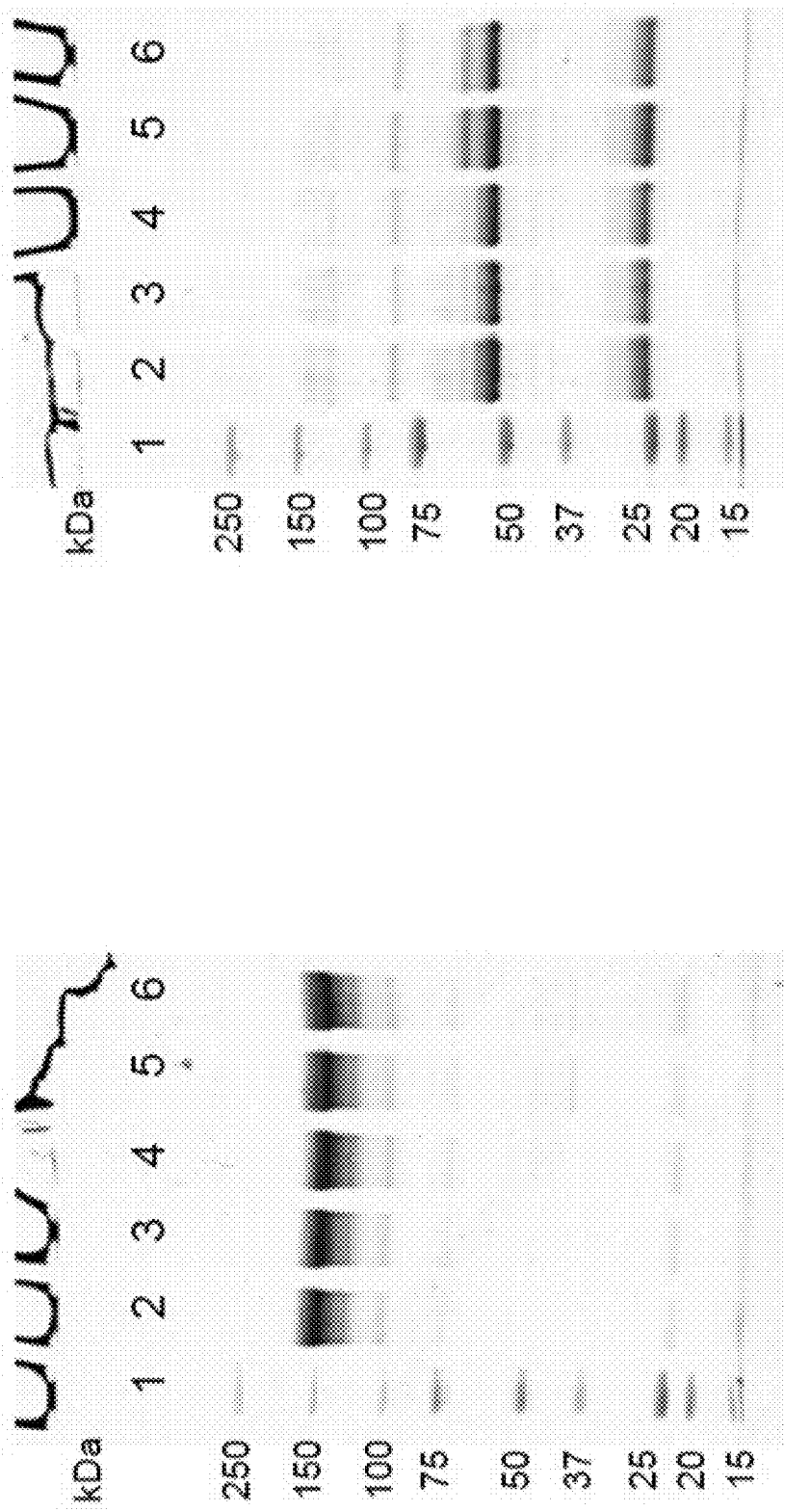
FIG. 21A-21B show the results of non-reducing (FIG. 21A) and reducing (FIG. 21B) SDS-PAGE analysis of commercial IVIG lots (lanes 2-4), IgG prepared from CM high salt wash fraction using CM Sepharose ff chromatography (lane 5), and IgG prepared from CM high salt wash fraction using CM Ceramic Hyper D4 chromatography (lane 6). Marker proteins are shown in lane 1.

SDS-PAGE analysis performed under reducing and non-reducing conditions were also performed for the two high salt CM wash fraction compositions and compared to the three lots of commercial IVIG. As shown in FIG. 21A there were no major differences in the non-reducing profile of the CM wash fraction preparations (lane 5: FC CM Sepharose ff, lane 6: FC CM Ceramic Hyper D 4) and commercial IVIG lots (lanes 2-4). In all lanes, a clear band at 150 kDa, corresponding to monomeric IgG (~150 kDa), was visible. However, a weakly staining band at 40 kDa was observed in the high salt CM wash fraction preparations, but not in the commercial IVIG preparations.

As shown in FIG. 21B, the reducing profiles of the high salt CM wash fraction preparations (lane 5: FC CM Sepharose ff; lane 6: FC CM Ceramic Hyper D 4) varied from the profiles of the commercial IVIG preparations by the presence of a more pronounced band at about 60 kDa. This band likely corresponds to the heavy chain of $IgG_3$, which is larger than the heavy chains of $IgG_1$, $IgG_2$, and $IgG_4$. As shown in Table 10, the $IgG_3$ content of the high salt CM wash fractions is highly enriched, as compared to the content in normal human plasma.

TABLE 10

IgG subclass distribution of the final IgG composition prepared from the 2M sodium chloride wash fraction formed in the method outlined in FIG. 1.

| | IgG subclasses | | | |
|---|---|---|---|---|
| | IgG1 [%] | IgG2 [%] | IgG3 [%] | IgG4 [%] |
| FC CM Sepharose ff | 60.9 | 14.8 | 23.9 | 0.5 |
| FC CM Ceramic Hyper D 4 | 58.1 | 15.7 | 25.7 | 0.5 |
| Normal Human Serum | 60.3-75.0 | 16.7-31.0 | 5.0-8.4 | 0.7-4.2 |

A human in vitro system was used to analyze potential modulatory effects of the IgG compositions prepared from the high salt CM wash fractions and a commercial IVIG composition on effector functions in antibody-dependent cellular cytotoxicity (ADCC) assays. Briefly, density gradient-purified human peripheral blood mononuclear cells (PBMC) from healthy human donors were incubated with culture medium, the IgG compositions prepared from the high sale CM wash fractions, of a commercial IVIG product, at equal protein concentrations. ADCC was determined by washing the PBMC with serum-free medium and adding the cells at a ratio of 20:1 to human SK-BR3 breast cancer cells opsonized with herceptin. The cytotoxic damage to SK-BR3 cells was determined by measuring LDH release. ADCC was calculated according the formula below. As shown in Table 11, the ADCC activities of the IGG compositions prepared from the high salt CM wash fractions were 70% to 100% greater than the commercial IVIG product.

$$ADCC = \frac{100(\text{Exp}_{Her10-300} - \text{Exp}_{Her0})}{(S_{max} - S_{spo})}$$

$\text{Exp}_{Her10-300}$, $\text{Exp}_{Her0}$—experimental LDH release in presence and absence of herceptin $S_{max}$—maximum LDH release $S_{spo}$—spontaneous LDH release.

TABLE 11

ADCC modulation by final IgG composition prepared from the 2M sodium chloride wash fraction formed in the method outlined in FIG. 1.

| | donor number | ADCC [%] ratio between IGIV reference lot and test sample |
|---|---|---|
| FC CM Sepharose ff | 4 | 199.9 ± 33.1 |
| FC CM Ceramic Hyper D 4 | 4 | 171.5 ± 9.0 |

For additional characterization, the IgG composition purified from the high salt CM wash fraction using CM Ceramic Hyper D resin was further separated into individual IgG subclasses using Capture Select IgG4 and Mab Select SuRe chromatographic resins. The results of the separation are shown in Table 12 and Table 13.

TABLE 12

Recovery of IgG subclass fractionation of final IgG composition prepared from the 2M sodium chloride wash fraction formed in the method outlined in FIG. 1.

| | IgG subclasses - recovery [%] | | | |
|---|---|---|---|---|
| | IgG1 | IgG2 | IgG3 | IgG4 |
| IgG1 FC | 85.1 | 7.4 | 1.4 | <10.6 |
| IgG2 FC | 8.4 | 88.1 | 9.8 | <0.66 |
| IgG3 FC | 0.02 | 0.06 | 76.1 | <0.54 |
| IgG4 FC | 0.09 | 1.1 | 0.16 | 87.6 |

TABLE 13

Purity of IgG subclass compositions seperated from final IgG composition prepared from the 2M sodium chloride wash fraction formed in the method outlined in FIG. 1.

| | IgG subclasses - purity [%] | | | |
|---|---|---|---|---|
| | IgG1 | IgG2 | IgG3 | IgG4 |
| IgG1 FC | 96.6 | 2.6 | 0.7 | <0.14 |
| IgG2 FC | 21.0 | 67.7 | 11.2 | <0.02 |
| IgG3 FC | 0.07 | 0.05 | 99.9 | <0.02 |
| IgG4 FC | 5.7 | 22.1 | 4.9 | 67.3 |

Titers of antibodies which bind specifically to SNA, autoantibodies, and brain disease-related antibody were determined for each of the IgG subclass preparations and compared against levels in a commercial IVIG preparation. The results of these analyses are presented in Table 14. Notably, anti-RAGE antibodies were found to be elevated for all subclass preparations, as compared to the commercial IVIG product. This enrichment was more than 10-fold in the IgG2 and IgG3 compositions, 91-fold in the IgG4 composition, and 156-fold in the IgG1 composition. Anti-α synuclein antibodies were enriched 7 to 32-fold, as compared to the commercial IVIG product, in the various subclass preparations. The various anti-β amyloid titers were elevated in the IgG1, IgG2, and IgG3 subclass preparations, but not in the IgG4 composition. In the IgG2 composition, anti-Aβ titers were enriched 42-fold to 70-fold. In the IgG1 composition, these titers were enriched between 58-fold and 114-fold. In the IgG3 composition, these titers were enriched between 108-fold and 160-fold.

TABLE 14

Characterization of antibody titers in IgG subclass compositions seperated from final IgG composition prepared from the 2M sodium chloride wash fraction formed in the method outlined in FIG. 1.

| | Unit | IgG1 FC | IgG2 FC | IgG3 FC | IgG4 FC | Mean/range Gammagard Liquid (GGL) |
|---|---|---|---|---|---|---|
| IgG-SNA | OD/mg | 3.0 | 2.2 | 1.7 | 5.3 | 2.2 |
| | % plasma | 92.7 | 67.7 | 51.3 | 142.9 | 65.2-94.8 |
| Anti-DNA IgG | ratio to GGL | 3.6 | 2.6 | 2.9 | 1.2 | — |
| Anti-tubulin IgG | μg/ml | 1.7 | 1.8 | 2.3 | 1.2 | 1.2 |
| | ratio to GGL | 1.4 | 1.5 | 1.9 | 1.0 | — |
| Anti-rHuPH20 IgG | μg/ml | 13.2 | 1.3 | 4.9 | 0.65 | — |
| Anti-PCP IgG | μg/ml | 480 | 367 | 32.6 | 3.3 | 920.8 |
| | ratio to GGL | 0.52 | 0.40 | 0.035 | 0.0036 | — |
| Anti-Hib IgG | μg/ml | 89.2 | >192 | 0.89 | 0.47 | 28.6 |
| | ratio to GGL | 3.1 | >6.7 | 0.031 | 0.016 | — |
| Anti-RAGE IgG | ratio to GGL | 155.7 | 11.1 | 13.9 | 90.9 | |
| Anti-α synuclein IgG | ratio to GGL | 29.0 | 16.3 | 32.6 | 7.3 | — |
| Anti-β amyloid 40 IgG | ratio to GGL | 88.8 | 55.2 | 129.7 | 0.58 | — |

TABLE 14-continued

Characterization of antibody titers in IgG subclass compositions seperated from final IgG composition prepared from the 2M sodium chloride wash fraction formed in the method outlined in FIG. 1.

| | Unit | IgG1 FC | IgG2 FC | IgG3 FC | IgG4 FC | Mean/range Gammagard Liquid (GGL) |
|---|---|---|---|---|---|---|
| Anti-β amyloid 42 IgG | ratio to GGL | 58.2 | 58.6 | 108.3 | 0.8 | — |
| Anti-β amyloid 40 oligomers IgG | ratio to GGL | 114.0 | 70.2 | 160.8 | 1.1 | — |
| Anti-β amyloid 40 fibrils IgG | ratio to GGL | 83.9 | 42 | 144.3 | 1.67 | — |

Example 10—Characterization of High Salt Wash Fractions Formed During Cation Exchange Enrichment of Plasma-Derived IgG To further characterize the protein composition of the high salt wash fraction formed during cation exchange enrichment of plasma-derived IgG, the wash fractions from three large-scale IgG preparations were recovered. The pH of the three fractions ranged from 8.5 to 8.8. As shown in Table 15, the average protein concentration of the fractions was 0.14% (1.4 g/L), a yield of approximately 0.071 grams of protein per liter of starting plasma. The average content of IgG in the fractions was 82.9% (g IgG/g total protein), as determined by nephelometry. The average IgA and IgM contents of fractions were 4.12% and 2.84% (g/g total protein), respectively, as determined by ELISA.

TABLE 15

Biochemical characterizations of CM high salt wash fractions from large-scale IgG purification.

| CM cleaning fraction | TPUV [%] | TPUV [g/l plasma] | IgG nephelometry [% of TP] | IgG nephelometry [g/l plasma] | IgA ELISA [% of TP] | IgM ELISA [% of TP] |
|---|---|---|---|---|---|---|
| LE12L369Z | 0.13 | 0.078 | n.d. | n.d. | 3.70 | 1.61 |
| LE12M177Z | 0.12 | 0.083 | 81.4 | 0.067 | 4.24 | 3.39 |
| LE12N036Z | 0.16 | 0.052 | 84.4 | 0.044 | 4.41 | 3.54 |
| Mean | 0.14 | 0.071 | 82.9 | 0.056 | 4.12 | 2.84 | n.d. = not determined

The fractions were then ultra/diafiltrated to reduce their conductivities and concentrate the protein, as described herein, and then sterile filtered. The molecular weight distribution of the fractions after filtration was then determined by high-performance liquid size exclusion chromatography (HP-SEC). As shown in Table 16, monomeric IgG, corresponding to the main peak centered at 160 kDa, constituted approximately 70% of the protein in the fractions. The relatively high average percentages of immunoglobulin dimer, about 20%, and oligomer, about 7%, are partially explained by the IgA and IgM contents of the fraction. IgA normally exists as an immunoglobulin dimer, while IgM is an immunoglobulin pentamer.

TABLE 16

Molecular weight distributions of CM high salt wash fractions from large-scale IgG purification.

| CM cleaning fraction | Molecular size distribution [%] | | | |
|---|---|---|---|---|
| concentrate sterile filtrate | >450 kDa | ~350 kDa | ~160 kDa | <110 kDa |
| LE12L369Z | 4.2 | 20.1 | 72.8 | 3.0 |
| LE12M177Z | 7.1 | 21.3 | 68.5 | 3.2 |
| LE12N036Z | 9.4 | 19.5 | 66.2 | 4.8 |
| Mean | 6.9 | 20.3 | 69.2 | 3.6 |

The distribution of IgG subclasses in one of the wash fractions was then determined by chromatographic separation using Capture Select IgG4 and Mab Select SuRe resins. As shown in Table 17, the content of $IgG_3$ subclass in the fraction (25%) was greatly enriched as compared to a typical content in normal human plasma (5.0-8.4%). The content of each of subclasses $IgG_1$, $IgG_2$, and $IgG_4$ was at the low end of a typical distribution in normal human plasma.

TABLE 17

Analysis of IgG subclass distribution in a CM high salt wash fraction from a large-scale IgG purification.

| CM cleaning fraction | IgG Subclasses | | | |
|---|---|---|---|---|
| concentrate sterile filtrate | IgG1 [%] | IgG2 [%] | IgG3 [%] | IgG4 [%] |
| LE12N036Z | 57.42 | 16.73 | 25.18 | 0.66 |

Figure 17A:
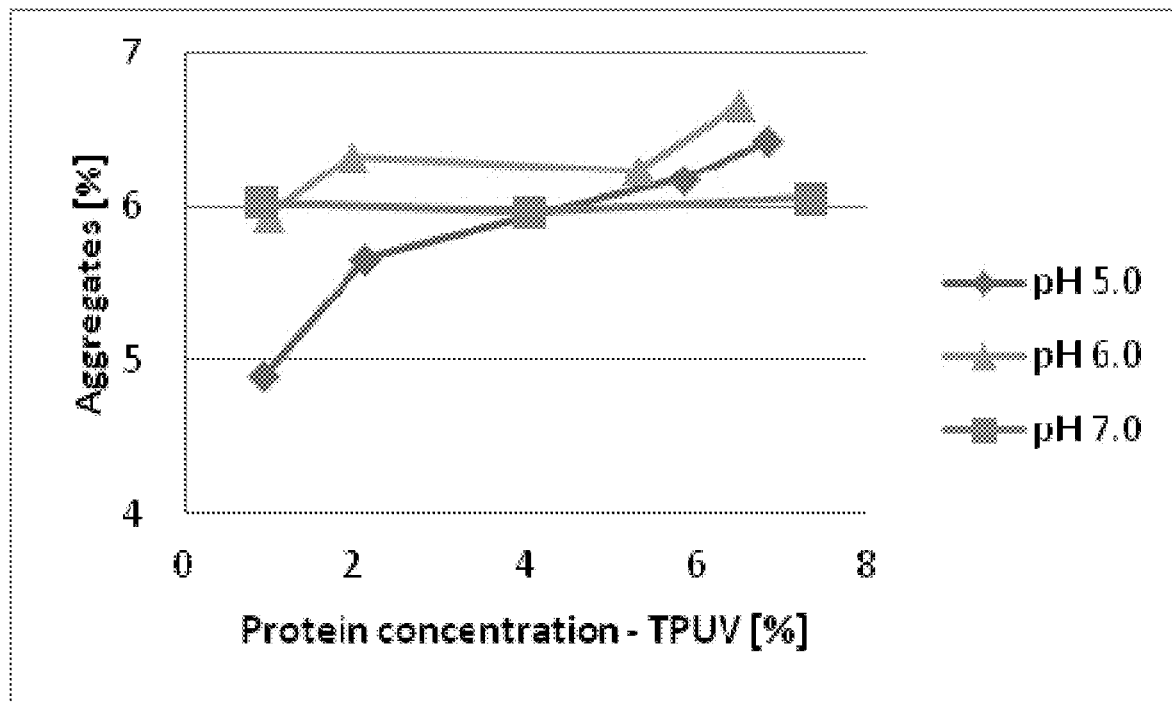
FIG. 17A illustrates a plot of protein aggregation as a function of protein concentration for samples of a CM high salt wash fraction ultra/diafiltered into buffer at pH 5.0, 6.0, and 7.0.
Figure 17B:
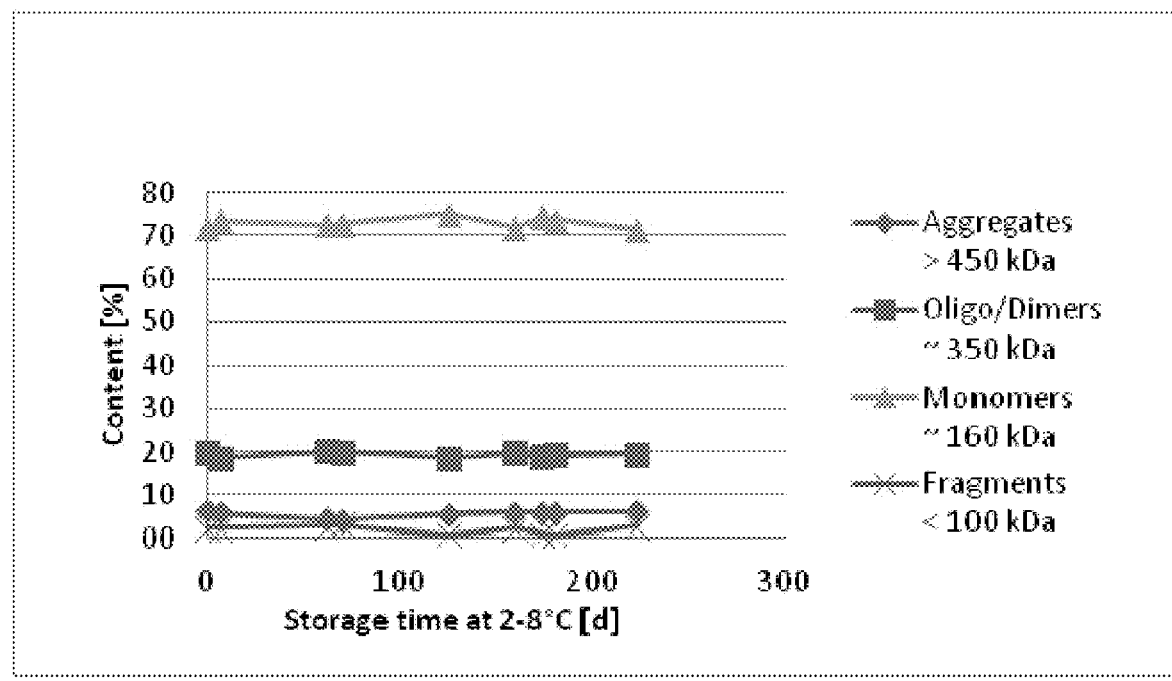
FIG. 17B illustrates the stability of a CM high salt wash fraction ultra/diafiltered into buffer at pH 7.0, 11.5 mS/cm, over a seven month incubation period.

Example 11—Ultra/Diafiltration of a High Salt Wash Fraction Formed During Cation Exchange Enrichment of Plasma-Derived IgG In order to load the high salt high wash fraction onto a subsequent cation exchange resin, the conductivity of fraction needs to be reduced. One means for accomplishing this is by ultra/diafiltration. To determine appropriate conditions for the ultra/diafiltration, samples of one of the high salt CM wash fraction described in example 10 were diafiltered into buffer at pH 5.0, 6.0 or 7.0, and then concentrated by ultrafiltration. The aggregate content of the samples was monitored during concentration. As seen in FIG. 17A, protein aggregation increased with increasing protein concentration, from 10 g/L to 80 g/L, when the fractions were diafiltered into buffer at pH 5.0 (♦) and pH 6.0 (▲). However, protein aggregation did not increase during ultra-filtration at pH 7.0 (■). To determine whether the fraction was stable over time at this pH, a sample diafiltered into buffer at pH 7.0, and conductivity of 11.5 mS/cm, was concentrated to 2% protein (20 g/L) and stored for seven months. The molecular size distribution of the sample was monitored during storage. As shown in FIG. 17B, there was no change in the molecular weight distribution profile over the course of the experiment, suggesting the sample is stable at pH 7.0.

Example 12—Sterile Filtration of an Ultra/Diafiltered High Salt Wash Fraction Formed During Cation Exchange Enrichment of Plasma-Derived IgG To determine the effects of protein concentration, pH, and conductivity on the recovery of IgG, IgA, and IgM during sterile filtration following ultra/diafiltration, a series of experiments was performed across various conditions. Briefly, samples of a high salt CM wash fraction were ultra/diafiltered to protein concentrations varying from 0.2% (2 g/L) to 1.5% (15 g/L), at a pH from 5.0 to 7.0, and conductivity from 1 mS/cm to 8 mS/cm. The samples were filtered through a SARTOBRAN® P (0.45/0.2 m) filter, and the IgG, IgA, and IgM contents of the filtrate were determined. The results of the experiments are shown in FIGS. 18A-18J.

Figure 18A:
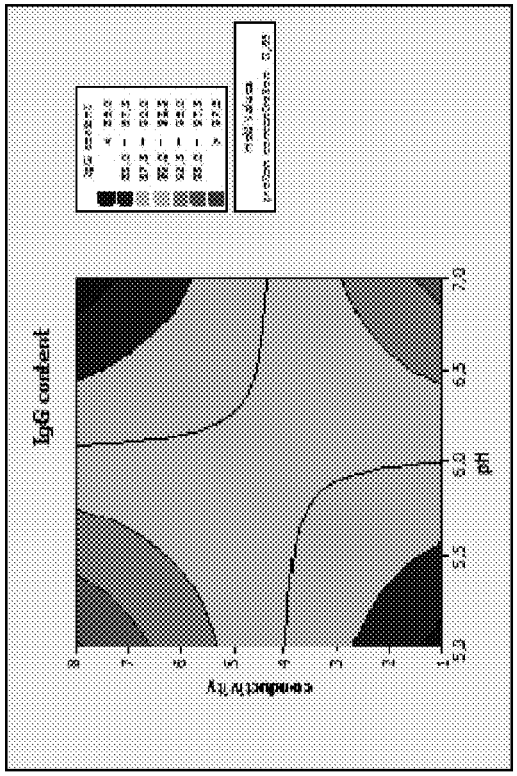
FIG. 18A-18I illustrate contour plots of IgG, IgA, and IgM recovery from high salt CM wash fractions after ultra/diafiltration and sterile filtration across ranges of pH 5-7, conductivity 1.0 mS/cm to 8.0 mS/cm, and protein concentration 0.2% (2 g/L) to 1.5% (15 g/L).
Figure 18B:
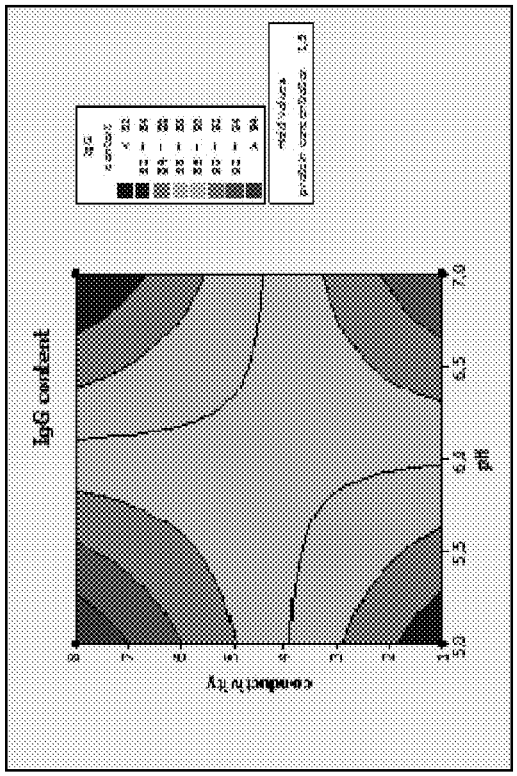
Figure 18C:
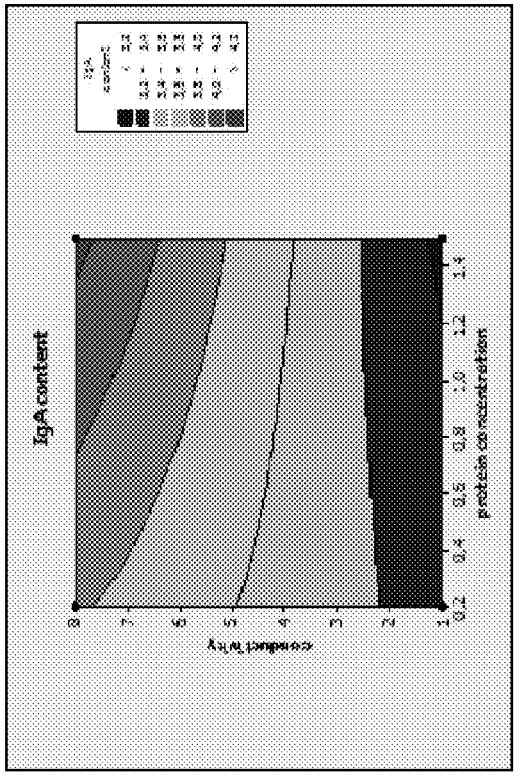
Figure 18D:
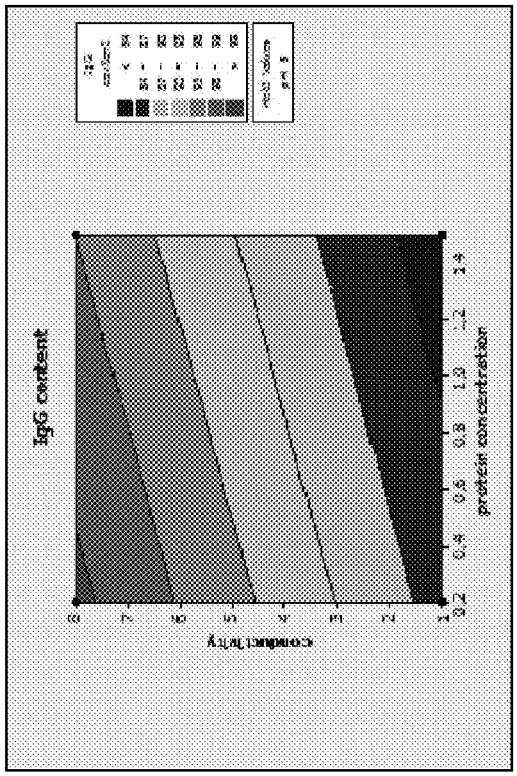

FIGS. 18A-18B show a contour plot of IgG content (as % total protein) recovered in the filtrate of samples concentrated to 1.5% (15 g/L) and 0.85% (8.5 g/L), respectively, at pH values ranging from 5.0 to 7.0 and conductivities from 1.0 mS/cm to 8.0 mS/cm. As shown in the these figures, maximum IgG content is found after filtration at pH/conductivity combinations of pH 5.0 and 8.0 mS/cm, as well as pH 7.0 and 1.0 mS/cm. Minimum IgG content is found after filtration at pH/conductivity combinations of pH 5.0 and 1.0 mS/cm, as well as pH 7.0 and 8.0 mS/cm. FIG. 18C shows a contour plot of IgG content (as % total protein) recovered in the filtrate of samples diafiltrated into buffer at pH 5, protein concentrations ranging from 0.2% (2 g/L) to 1.5% (15 g/L), and conductivity ranging from 1.0 mS/cm to 8.0 mS/cm. As shown in FIG. 18C, increasing IgG content was correlated with increasing conductivity at pH 5.0, but largely unaffected by total protein concentration. Similarly, IgA content showed a positive correlation with increasing conductivity at pH 5, but showed only a slight correlation with protein concentration at conductivities greater than 5.0 mS/cm (FIG. 18D).

Figure 18E:
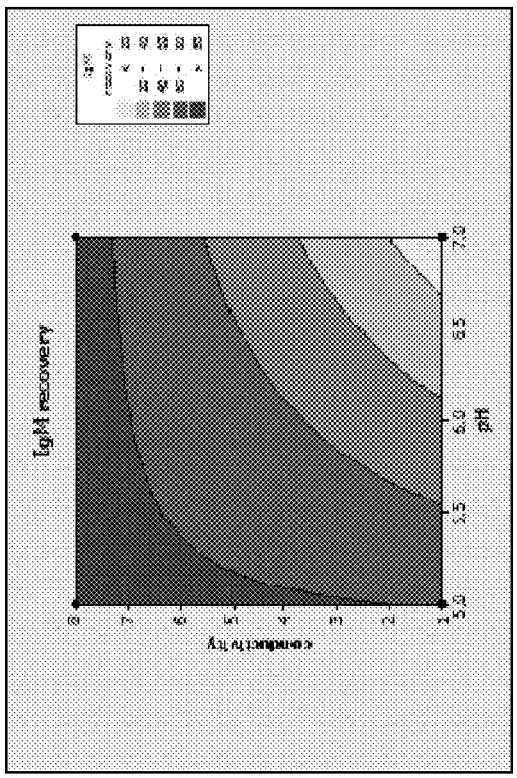
Figure 18F:
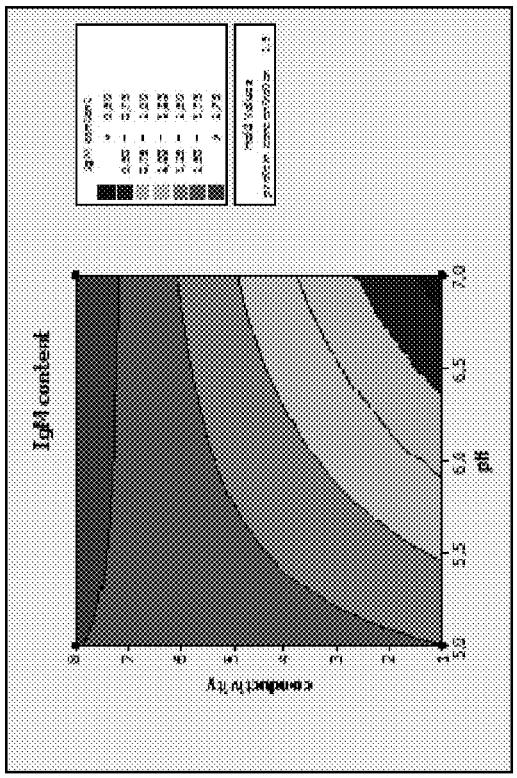
Figure 18G:
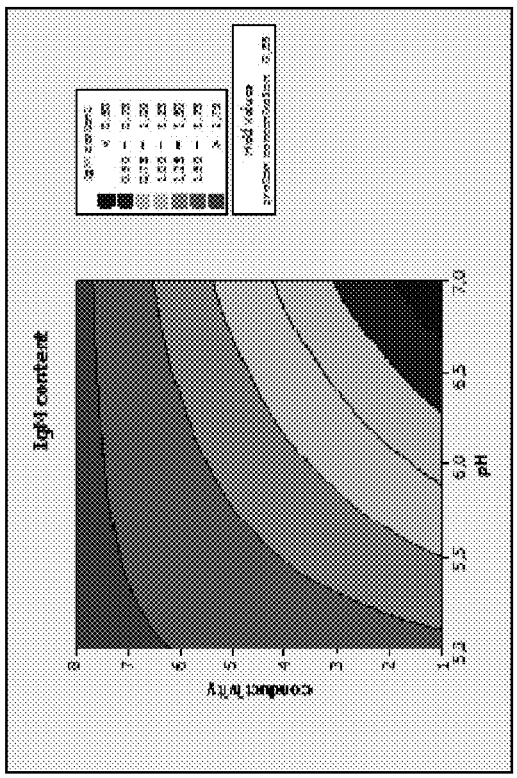
Figure 18H:
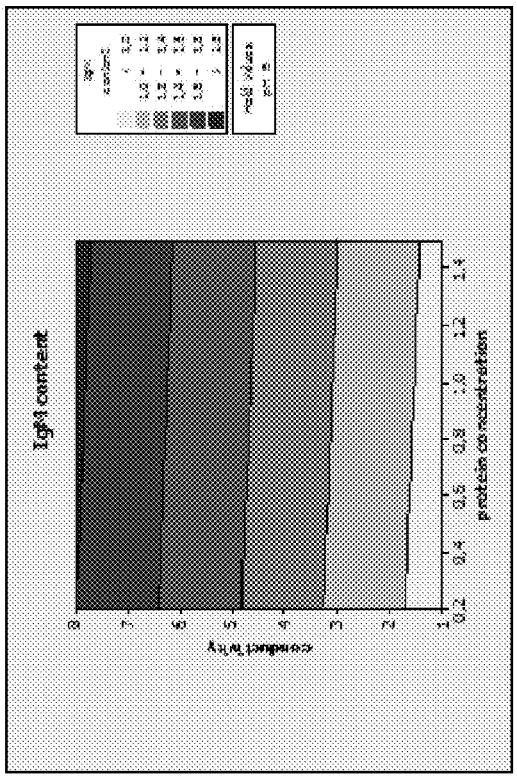
Figure 18J:
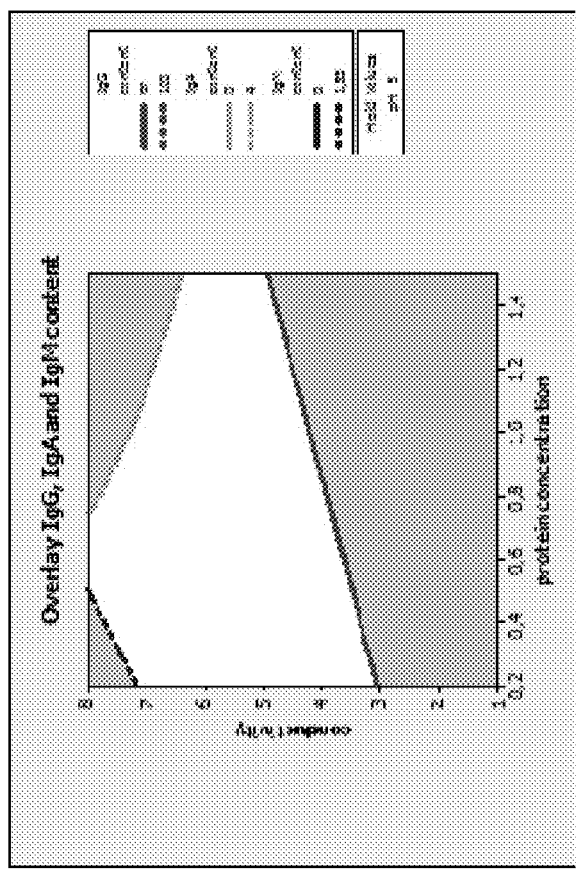
FIG. 18J illustrates an overlay of contour plots from IgG, IGA, and IgM recovery experiments conducted at pH 5.0.
Figure 18I:
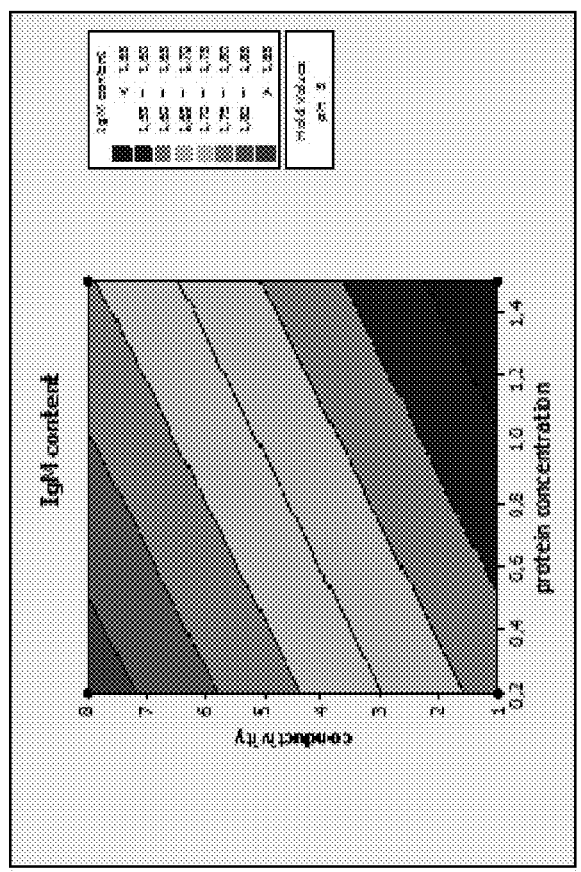

IgM recovery and content in the filtrate of samples ultra/diaflitrated to a final protein concentration of 1.5% (15 g/L) or 0.85% (8.5 g/L) were dependent upon both pH and conductivity. As shown in FIGS. 18E-18G, IgM recovery and content decreased with increasing pH and increased with increasing conductivity. As shown in FIG. 18H, IgM content in the filtrate was positively correlated with increasing conductivity, but unrelated to final protein concentration, at pH 6.0. However, the results presented in FIG. 18I show a positive correlation between IgM content in the filtrate and increasing conductivity, as well as a negative correlation between IgM content and total protein concentration at pH 5.0.

IgG, IgA, and IgM contour plots at pH 5.0 were overlayed to determine working conditions (at pH 5.0), which provide high IgG recovery in the filtrate and lower IgA and IgM recoveries. This working space is illustrated as the white area of FIG. 18A.

Figure 19:
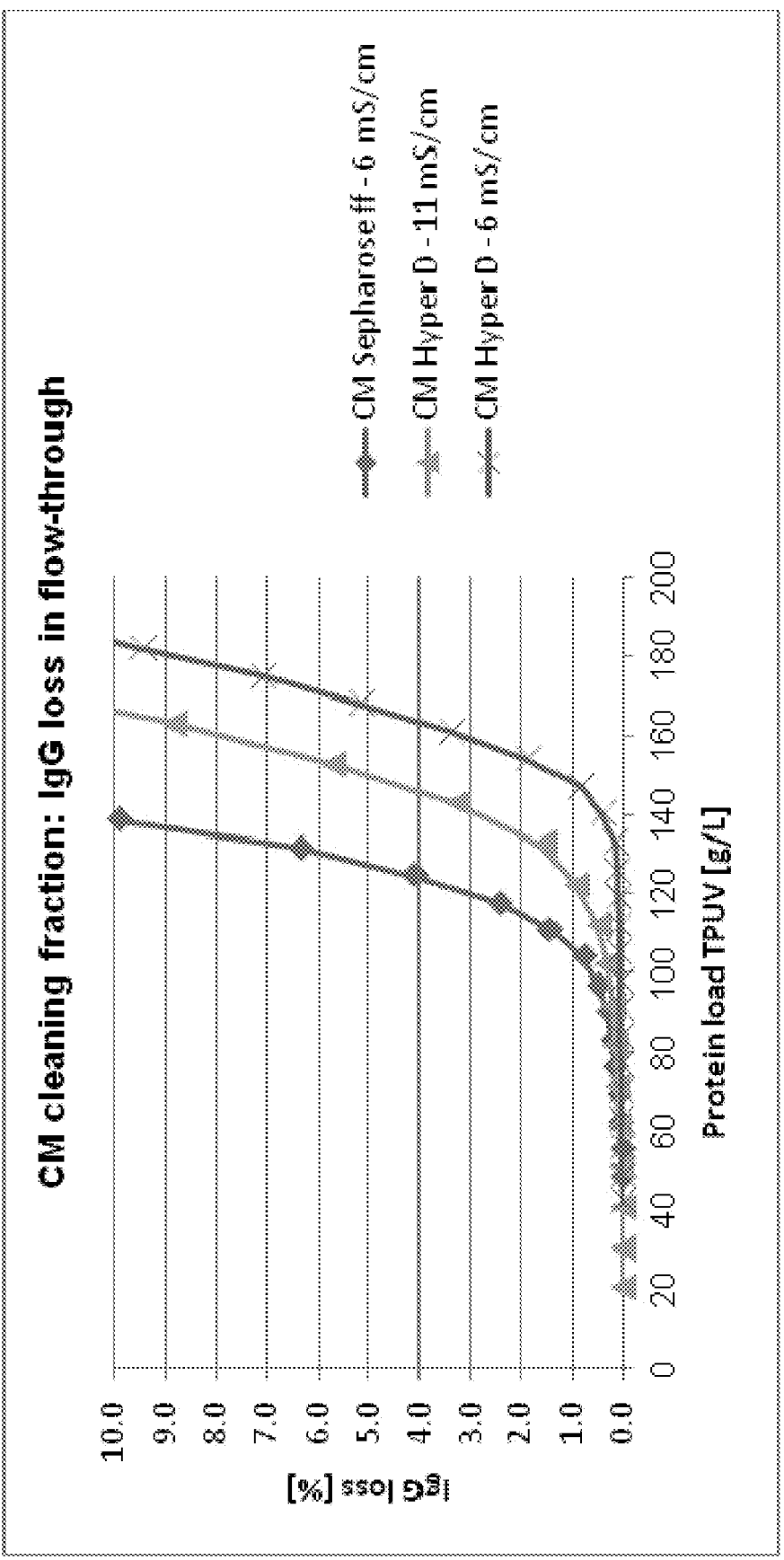
FIG. 19 illustrates IgG breakthrough curves for CM sepharose ff and CM ceramic hyper D cation exchange resins.

Example 13—Chromatographic Enrichment of IgG from Sterile Filtered High Salt Wash Fraction Formed During Cation Exchange Enrichment of Plasma-Derived IgG Portions of a high salt CM wash fraction were diafiltered into buffer at pH 5.2 and a conductivity of either 6 mS/cm or 11 mS/cm and then ultrafiltered to a final protein concentration of 0.7% (7 g/L) or 1.7% (17 g/L). Break through curves on CM Sepharose ff and CM Ceramic Hyper D using the ultra/diafiltered samples at different starting conductivities and concentrations were recorded to evaluate the loading capacities for concentrated CM cleaning fraction filtrate. For these experiments, columns with 31 mL resin volume were used. As shown in FIG. 19, the CM Ceramic Hyper D resin provided a higher loading capacity than did CM Sepharose ff resin, and reducing the conductivity of the load material from 11 mS/cm to 6 mS/cm further increased the loading capacity.

CM Sepharose ff and CM Ceramic Hyper D resins loaded with varying amounts of protein were then eluted and the recovery of IgG, IgA, and IgM characterized. As shown in Table 18, use of CM Sepharose ff resin provided a greater reduction in IgA and IgM content, however, use of CM Ceramic Hyper D resin provided a greater recovery of IgG content.

TABLE 18

Analysis of IgG subclass distribution in a CM high salt wash fraction from a large-scale IgG purification.

|  | Protein load [mg protein/ml resin] | Loading conductivity [mS/cm] | IgG step recovery [%] | IgA step recovery [%] | IgM step recovery [%] | MSD <110 kDa [%] |
|---|---|---|---|---|---|---|
| CM Sepharose ff | 105 | 6 | 91 | 85 | 38 | 2.54 |
| CM Sepharose ff | 150 | 6 | 76 | 56 | 19 | 3.02 |
| CM Ceramic Hyper D | 150 | 6 | 99 | 63 | 70 | 2.46 |
| CM Ceramic Hyper D | 90 | 11 | 103 | 78 | 85 | 1.80 |

CM eluates were then adjusted to a pH of 6.4 and a conductivity of ≥1 mS/cm, filtered through a SARTOBRAN® P (0.45/0.2 m) filter, and loaded onto an ANX Sepharose ff resin. The recovered flow-through was then ultra/diafiltered using a PES UF/DF membrane and subjected to another sterile filtrations to provide a bulk product. The content of small peptides (MSD<110 kDa) in the various steps was characterized for four samples, one of which was enriched using CM Sepharose ff resin (run 1) and three of which were enriched using CM Ceramic Hyper D resin (runs 2-4). As seen in Table 19, use of CM Ceramic Hyper D resin, but not CM Sepharose ff resin, reduced the content of smaller peptides in the composition

TABLE 19

Reduction of proteins <110 kDa during downstream process using CM Sepharose ff (run 1) and CM Ceramic Hyper D (run 2 to 4).

|  | MSD <110 kDa [%] | | | |
|---|---|---|---|---|
|  | Run 1 | Run 2 | Run 3 | Run 4 |
| CM cleaning fraction concentrate sterile filtrate | 2.95 | 2.31 | 2.24 | 2.78 |
| Sartobran filtrate 1 | 3.16 | 2.27 | 2.36 | 2.69 |
| CM eluate | 2.54 | 1.80 | 1.89 | 2.18 |
| Sartobran filtrate 2 | 2.56 | — | 0.52 | 0.38 |
| Bulk | 2.49 | 0.16 | 0.11 | 0.31 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An aqueous plasma-derived immunoglobulin G composition enriched in anti-amyloid β immunoglobulins, comprising:
    a content of at least 1% anti-amyloid β fibril immunoglobulin G;
    a content of at least 0.4% anti-amyloid β oligomer immunoglobulin G;
    a content of at least 0.2% anti-amyloid β monomer immunoglobulin G and a pharmaceutically acceptable stabilizing agent.

2. The plasma-derived immunoglobulin G (IgG) composition enriched in anti-amyloid β immunoglobulins of claim 1, further comprising:
    a titer of anti-RAGE immunoglobulin G that is at least 5-fold greater than the titer of anti-RAGE immunoglobulin G in an average pool of plasma from more than 1000 random plasma donors.

3. The plasma-derived immunoglobulin G (IgG) composition enriched in anti-amyloid β immunoglobulins of claim 1, further comprising:
    a titer of anti-α-synuclein immunoglobulin G that is at least 5-fold greater than the titer of anti-α-synuclein immunoglobulin G in an average pool of plasma from more than 1000 random plasma donors.

4. The plasma-derived immunoglobulin G (IgG) composition enriched in anti-amyloid β immunoglobulins of claim 1, comprising:
    a content of at least 2.5% anti-amyloid β fibril immunoglobulin G;
    a content of at least 1% anti-amyloid β oligomer immunoglobulin G; and
    a content of at least 0.5% anti-amyloid β monomer immunoglobulin G.

5. The plasma-derived immunoglobulin G (IgG) composition enriched in anti-amyloid β immunoglobulins of claim 4, further comprising:
    a titer of anti-RAGE immunoglobulin G that is at least 5-fold greater than the titer of anti-RAGE immunoglobulin G in an average pool of plasma from more than 1000 random plasma donors.

6. The plasma-derived immunoglobulin G (IgG) composition enriched in anti-amyloid β immunoglobulins of claim 4, further comprising:
    a titer of anti-α-synuclein immunoglobulin G that is at least 5-fold greater than the titer of anti-α-synuclein immunoglobulin G in an average pool of plasma from more than 1000 random plasma donors.

7. The plasma-derived immunoglobulin G (IgG) composition enriched in anti-amyloid β immunoglobulins of claim 1, comprising:
    a content of at least 5% anti-amyloid β fibril immunoglobulin G;
    a content of at least 2% anti-amyloid β oligomer immunoglobulin G; and
    a content of at least 1% anti-amyloid β monomer immunoglobulin G.

8. The plasma-derived immunoglobulin G (IgG) composition enriched in anti-amyloid β immunoglobulins of claim 7, further comprising:
    a titer of anti-RAGE immunoglobulin G that is at least 5-fold greater than the titer of anti-RAGE immunoglobulin G in an average pool of plasma from more than 1000 random plasma donors.

9. The plasma-derived immunoglobulin G (IgG) composition enriched in anti-amyloid β immunoglobulins of claim 7, further comprising:
    a titer of anti-α-synuclein immunoglobulin G that is at least 5-fold greater than the titer of anti-α-synuclein immunoglobulin G in an average pool of plasma from more than 1000 random plasma donors.

10. The plasma-derived immunoglobulin G (IgG) composition enriched in anti-amyloid β immunoglobulins of claim 1, wherein the pharmaceutically acceptable stabilizing agent is glycine.

11. A method for treating Alzheimer's disease comprising: administering a therapeutically effective amount of a plasma-derived immunoglobulin G composition enriched in anti-amyloid β immunoglobulins according to any one of claims 1-9 and 10.

* * * * *